US011104628B2

(12) United States Patent
Stoessel et al.

(10) Patent No.: US 11,104,628 B2
(45) Date of Patent: Aug. 31, 2021

(54) AROMATIC COMPOUNDS

(71) Applicant: Merck Patent GmbH, Darmstadt (DE)

(72) Inventors: Philipp Stoessel, Frankfurt am Main (DE); Christian Ehrenreich, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/499,478

(22) PCT Filed: Mar. 26, 2018

(86) PCT No.: PCT/EP2018/057591
§ 371 (c)(1),
(2) Date: Sep. 30, 2019

(87) PCT Pub. No.: WO2018/177981
PCT Pub. Date: Oct. 4, 2018

(65) Prior Publication Data
US 2020/0039903 A1 Feb. 6, 2020

(30) Foreign Application Priority Data

Mar. 29, 2017 (EP) .................................. 17163531

(51) Int. Cl.
| | | |
|---|---|---|
| C07C 25/18 | (2006.01) | |
| C07C 17/35 | (2006.01) | |
| C07C 25/22 | (2006.01) | |
| C07C 41/18 | (2006.01) | |
| C07C 43/225 | (2006.01) | |
| C07D 213/06 | (2006.01) | |
| C07D 213/127 | (2006.01) | |
| C07D 239/30 | (2006.01) | |
| C07D 401/14 | (2006.01) | |
| C07D 405/14 | (2006.01) | |
| C07D 471/04 | (2006.01) | |
| C07F 7/08 | (2006.01) | |

(52) U.S. Cl.
CPC .............. *C07C 25/18* (2013.01); *C07C 17/35* (2013.01); *C07C 25/22* (2013.01); *C07C 41/18* (2013.01); *C07C 43/225* (2013.01); *C07D 213/06* (2013.01); *C07D 213/127* (2013.01); *C07D 239/30* (2013.01); *C07D 401/14* (2013.01); *C07D 405/14* (2013.01); *C07D 471/04* (2013.01); *C07F 7/081* (2013.01); *C07F 7/083* (2013.01); *C07C 2602/08* (2017.05); *C07C 2602/10* (2017.05); *C07C 2603/18* (2017.05)

(58) Field of Classification Search
CPC ....... C07C 25/18; C07C 25/22; C07C 43/225; C07C 41/18; C07C 17/35; C07C 2602/10; C07C 2603/18; C07C 2602/08; H01L 51/0085; C07D 213/06; C07D 213/127; C07D 239/30; C07D 401/14; C07D 405/14; C07D 471/04; C07F 7/081; C07F 7/083

See application file for complete search history.

(56) References Cited

U.S. PATENT DOCUMENTS

| | | | | |
|---|---|---|---|---|
| 3,458,473 A | * | 7/1969 | Starnes, Jr. .............. | C08K 5/13 524/342 |
| 3,644,538 A | * | 2/1972 | Starnes .................... | C08L 23/02 568/720 |
| 9,708,351 B2 | * | 7/2017 | Alabugin ................. | C07C 1/325 |
| 2004/0259031 A1 | * | 12/2004 | Watanabe ............... | G11B 7/254 430/270.15 |
| 2017/0369455 A1 | | 12/2017 | Alles et al. | |
| 2018/0026209 A1 | * | 1/2018 | Stoessel ............... | C07F 15/0073 252/519.2 |
| 2018/0254416 A1 | * | 9/2018 | Stoessel ............... | C07D 213/68 |
| 2019/0157578 A1 | * | 5/2019 | Stoessel ............... | C07F 15/0033 |
| 2019/0161510 A1 | * | 5/2019 | Stoessel ............... | C07F 15/0033 |
| 2019/0241591 A1 | * | 8/2019 | Stoessel ............... | C07F 15/0033 |
| 2019/0252628 A1 | * | 8/2019 | Stoessel ............... | H01L 51/0085 |
| 2019/0280220 A1 | * | 9/2019 | Stoessel ............... | H01L 51/0085 |
| 2019/0315787 A1 | * | 10/2019 | Stoessel ............... | C07D 401/14 |

FOREIGN PATENT DOCUMENTS

| | | |
|---|---|---|
| WO | 2016097311 A1 | 6/2016 |
| WO | 2016124304 A1 | 8/2016 |

OTHER PUBLICATIONS

Pccompound-selected items 1-3, Create Date Sep. 18, 2005 to Sep. 25, 2014. PubChen Search Results provided.*
Y. Cho et al., 10 Beilstein Journal of Organic Chemistry, 956-968 (2014) (Year: 2014).*
CAS/CAPLUS Abstract and Indexed Compounds, P. Stoessel et al., WO 2016/124304 (2016) (Year: 2016).*
I. Stara et al., Science of Synthesis,1115-1146 (2010) (Year: 2010).*
International Search Report dated May 2, 2018 in International Patent Application No. PCT/EP2018/057591.
Johns et al., "Coordination Compounds of Tris (2-hydroxyphenyl)-s-triazine and Derivatives", https://pubs.acs.org/doi/pdf/10.1021/jo01049a058, 1962, pp. 592-594.
Shujiang et al., "An Efficient Improve for the Krohnke Reaction: One-pot Synthesis of 2,4,6-Triarylpyridines Using Raw Materials under Microwave Irradiation", Chemistry Letters, 2005, pp. 732-733, vol. 34, No. 5.
Xushun et al., "One-pot syntheiss of 2,4,6-triarylpyridines from [beta]—nitrostyrenes, substituted salicylic aldehydes and ammonium acetate" RSC Advances: An International Journal to Further the Chemical Sciences, 2016, pp. 95957-95964, vol. 6 No. 98.

(Continued)

*Primary Examiner* — Alexander R Pagano
(74) *Attorney, Agent, or Firm* — Faegre Drinker Biddle & Reath LLP

(57) ABSTRACT

The present invention relates to aromatic compounds suitable for preparation of asymmetric polydentate ligands. The present invention further describes a process for preparing asymmetric polydentate ligands and metal complexes comprising these ligands which are suitable for use as emitters in organic electroluminescent devices.

16 Claims, No Drawings

(56) References Cited

OTHER PUBLICATIONS

McInnes et al., "The high molecular weight polyphloroglucinols of the marine brown alga *Fucus vesiculosus* L. 1 H. and 13 C nuclear magnetic resonance spectroscopy", Canadian Journal of Chemistry, Database Reaxys (Online) Elsevier, 1985, pp. 304-313, vol. 63, No. 2.

Cai, C., et al., "New Tetraphosphorus Ligands for Highly Linear Selective Hydroformylation of Allyl and Vinyl Derivatives", Chemistry A European Journal, 2012, vol. 18, pp. 9992-9998.

* cited by examiner

AROMATIC COMPOUNDS

RELATED APPLICATIONS

This application is a national stage entry, filed pursuant to 35 U.S.C. § 371, of PCT/EP2018/057591, filed Mar. 26, 2018, which claims the benefit of European Patent Application No. 17163531.1, filed Mar. 29, 2017, which is incorporated herein by reference in its entirety.

The present invention relates to aromatic compounds suitable for preparation of asymmetric polydentate ligands. The present invention further describes a process for preparing asymmetric polydentate ligands and metal complexes comprising these ligands which are suitable for use as emitters in organic electroluminescent devices.

According to the prior art, triplet emitters used in phosphorescent organic electroluminescent devices (OLEDs) are iridium or else platinum complexes in particular, especially ortho-metallated complexes having aromatic ligands, where the ligands bind to the metal via a negatively charged carbon atom and an uncharged nitrogen atom or via a negatively charged carbon atom and an uncharged carbene carbon atom. Examples of such complexes are tris(phenylpyridyl)iridium(III) and derivatives thereof. The literature discloses a multitude of related ligands and iridium complexes, for example complexes with 1- or 3-phenylisoquinoline ligands, with 2-phenylquinolines or with phenylcarbenes.

More particularly, WO 2016/124304 A1 describes metal complexes having bridged ligands, where these generally contain three bidentate sub-ligands. The examples detailed in this publication include bridged ligands having different sub-ligands. However, relatively low yields are achieved in the preparation of the bridged ligands having different sub-ligands.

A problem addressed by the present invention is therefore that of providing a novel process for preparing polydentate ligands, which can be conducted with high yield and low costs. A further problem addressed by the present invention is that of providing a process for preparing metal complexes suitable as emitters for use in OLEDs. A particular problem addressed is that of providing emitters which exhibit improved properties in relation to efficiency, operating voltage and/or lifetime.

It has been found that, surprisingly, the use of aromatic compounds having all the features of Claim 1 in the preparation of polydentate ligands solves the abovementioned problems, and the complexes obtainable from the ligands are of very good suitability for use in an organic electroluminescent device.

The invention thus provides a compound of the following formula (I)

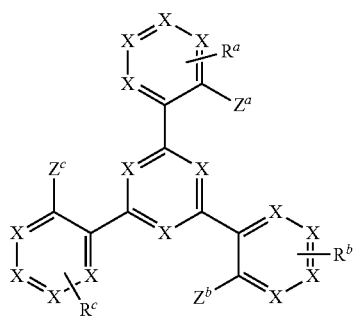

Formula (I)

where the symbols and indices used are as follows:
$Z^a$, $Z^b$, $Z^c$ is the same or different and is Cl, Br, I, B(OR)$_2$, OH, OSO$_2$R, Si(R)$_3$ or an alkoxy or thioalkoxy group having 1 to 20 carbon atoms, preferably Cl, Br, I, B(OR)$_2$, OH, OSO$_2$R, more preferably Cl, Br, I, B(OR)$_2$, especially preferably Cl, Br, I;

X is the same or different at each instance and is CR or N, preferably CR, or C if one $R^a$, $R^b$ or $R^c$ radical binds to X, with the proviso that not more than three X symbols per cycle are N;

R, $R^a$, $R^b$, $R^c$ is the same or different at each instance and is H, D, F, Cl, Br, I, N(R$^1$)$_2$, CN, NO$_2$, OH, COOH, C(=O)N(R$^1$)$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, where each alkyl, alkoxy, thioalkoxy, alkenyl or alkynyl group may be substituted by one or more R$^1$ radicals, where one or more nonadjacent CH$_2$ groups may be replaced by R$^1$C=CR$^1$, C≡C, Si(R$^1$)$_2$, C=O, NR$^1$, O, S or CONR$^1$, or an aromatic or heteroaromatic ring system which has 5 to 40 aromatic ring atoms and may be substituted in each case by one or more R$^1$ radicals, or an aryloxy or heteroaryloxy group which has 5 to 40 aromatic ring atoms and may be substituted by one or more R$^1$; at the same time, two R radicals together or one R radical together with one of the $R^a$, $R^b$, $R^c$ radicals may also form a ring system;

R$^1$ is the same or different at each instance and is H, D, F, Cl, Br, I, N(R$^2$)$_2$, CN, NO$_2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, where each alkyl, alkoxy, thioalkoxy, alkenyl or alkynyl group may be substituted by one or more R$^2$ radicals, where one or more nonadjacent CH$_2$ groups may be replaced by R$^2$C=CR$^2$, C≡C, Si(R$^2$)$_2$, C=O, NR$^2$, O, S or CONR$^2$, or an aromatic or heteroaromatic ring system which has 5 to 40 aromatic ring atoms and may be substituted in each case by one or more R$^2$ radicals, or an aryloxy or heteroaryloxy group which has 5 to 40 aromatic ring atoms and may be substituted by one or more R$^2$ radicals, or an aralkyl or heteroaralkyl group which has 5 to 40 aromatic ring atoms and may be substituted by one or more R$^2$ radicals, or a diarylamino group, diheteroarylamino group or arylheteroarylamino group which has 10 to 40 aromatic ring atoms and may be substituted by one or more R$^2$ radicals; at the same time, two or more R$^1$ radicals together may form a ring system;

R$^2$ is the same or different at each instance and is H, D, F or an aliphatic, aromatic and/or heteroaromatic organic radical, especially a hydrocarbyl radical, having 1 to 20 carbon atoms, in which one or more hydrogen atoms may also be replaced by F; at the same time, two or more R$^2$ substituents together may also form a ring system;

with the proviso that the compound of the formula (I) does not have C$_3$ symmetry.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

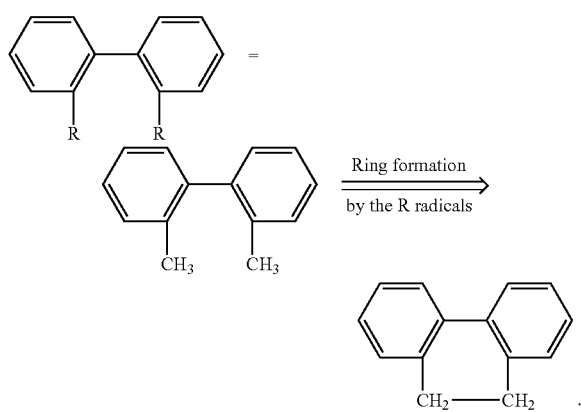

Ring formation of bicyclic, tricyclic and oligocyclic structures is likewise possible. In addition, however, the abovementioned wording shall also be understood to mean that, if one of the two radicals is hydrogen, the second radical binds to the position to which the hydrogen atom was bonded, forming a ring. This shall be illustrated by the following scheme:

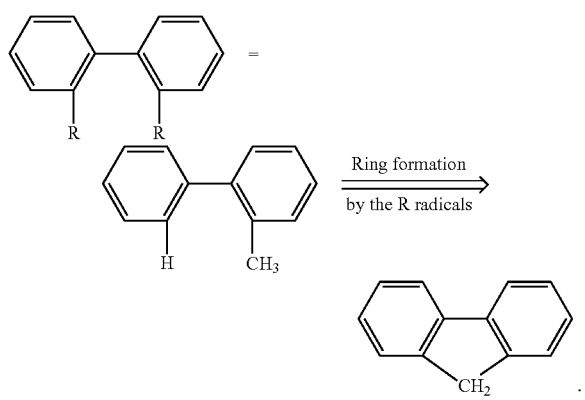

Entirely analogously, this shall also be understood to mean that, if both radicals are hydrogen atoms, in place of the two hydrogen atoms, a ring is formed via a single bond.

The formation of an aromatic ring system shall be illustrated by the following scheme:

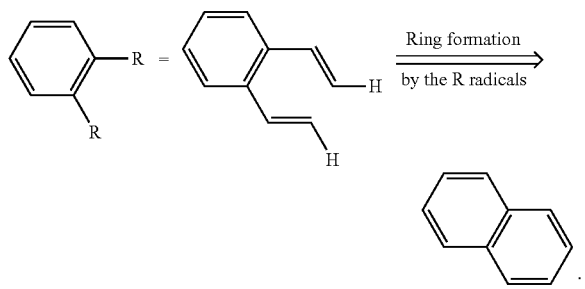

This kind of ring formation is possible in radicals bonded to carbon atoms directly bonded to one another, or in radicals bonded to further-removed carbon atoms. Preference is given to this kind of ring formation in radicals bonded to carbon atoms directly bonded to one another or to the same carbon atom.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc. In addition, in the context of the present invention, an aryl group shall be understood to mean a group in which two, three or more phenyl groups bonded directly to one another are bridged to one another via a $CR_2$ group, i.e., for example, a fluorene group, a spirobifluorene group or an indenofluorene group.

An aromatic ring system in the context of this invention contains 6 to 40 carbon atoms in the ring system. A heteroaromatic ring system in the context of this invention contains 1 to 40 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for a plurality of aryl or heteroaryl groups to be interrupted by a nonaromatic unit (preferably less than 10% of the atoms other than H), for example a carbon, nitrogen or oxygen atom or a carbonyl group. For example, systems such as triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be replaced by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl) cyclohex-1-yl, 1-(n-hexyl)cyclohex-1-yl, 1-(n-octyl) cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-40 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The inventive compounds of the formula (I) do not have $C_3$ symmetry, i.e. do not have a threefold axis of rotation, and preferably do not have $C_{3v}$ symmetry. Preferably, inventive compounds of the formula (I) have a symmetry of point group $C_s$ or $C_1$. These point groups are common knowledge and are described, for example, in Atkins, Child, & Phillips: Tables for Group Theory, Oxford University Press, 2006.

Accordingly, at least one of the three aromatic or heteroaromatic rings bonded to the central aromatic or heteroaromatic ring differs from at least one further ring among the three aromatic or heteroaromatic rings in the compound of formula (I). It may preferably be the case that the $Z^a$ group is not the same as the $Z^b$ or $Z^c$ group. In addition, the $R^a$ group may not be the same as the $R^b$ or $R^c$ group. It may further be the case that the $Z^a$ is not the same as the $Z^b$ group and the $Z^b$ group is not the same as the $Z^c$ group. If the $Z^a$ group is not the same as the $Z^b$ group, it may further be the case that the $R^a$ group is not the same as the $R^b$ or $R^c$ group.

In a further embodiment, the $Z^a$ group may be the same as the $Z^b$ group and the $Z^b$ group may be the same as the $Z^c$ group. In this embodiment, the $R^a$ group may not be the same as the $R^b$ group and the $R^b$ group may be the same as the $R^c$ group. In addition, if the $Z^a$ group is the same as the $Z^b$ group and the $Z^b$ group is the same as the $Z^c$ group, it may be the case that the $R^a$ group is not the same as the $R^b$ group and the $R^c$ group, and the $R^b$ group is not the same as the $R^c$ group.

In a preferred configuration, the compound may conform to the formula (II)

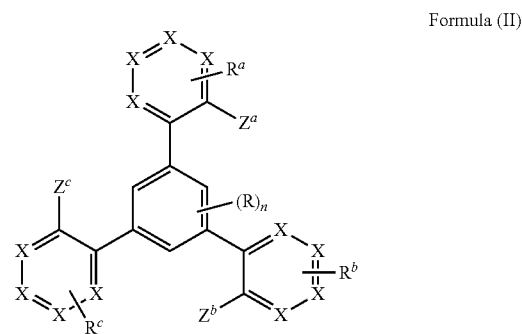

Formula (II)

where the symbols $Z^a$, $Z^b$, $Z^c$, R, $R^a$, $R^b$, $R^c$ and X used have the definitions given above, especially for formula (I), and n is 0, 1, 2 or 3, preferably 0 or 1.

Preferably, the compounds of the invention may conform to the formula (III)

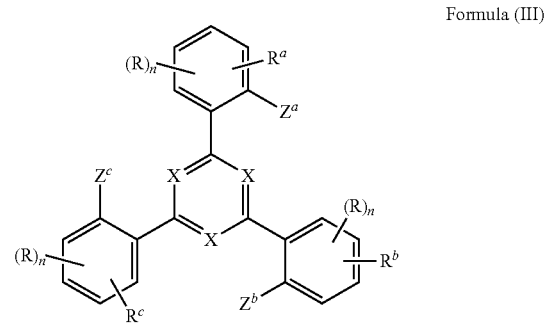

Formula (III)

where the symbols $Z^a$, $Z^b$, $Z^c$, R, $R^a$, $R^b$, $R^c$ and X used have the definitions given above, especially for formula (I), and n is the same or different at each instance and is 0, 1, 2 or 3, preferably 0 or 1.

Preferably, not more than two X groups in the formulae (I), (II) and (III) per ring are N. More preferably, the structure of the formula (I) or preferred embodiments thereof comprises not more than two nitrogen atoms, more preferably not more than one nitrogen atom and especially preferably no nitrogen atom. Furthermore, preference is given to compounds which are characterized in that, in formulae (I), (II) and (III), at least two X per ring and preferably all X are CR, where preferably at most 3, more preferably at most 2 and especially preferably at most 1 of the CR groups that X represents are not the CH group. More preferably, the structure of the formulae (I), (II) and (III) comprises not more than two R radicals that are not H, more preferably not more than one and especially none.

It may further be the case that the compound conforms to the formula (IV)

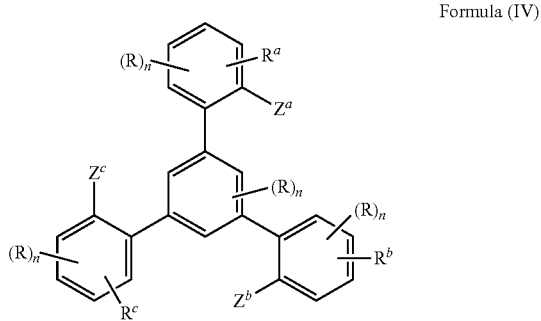

Formula (IV)

where the symbols $Z^a$, $Z^b$, $Z^c$, R, $R^a$, $R^b$ and $R^c$ used have the definitions given above, especially for formula (I), and n is the same or different at each instance and is 0, 1, 2 or 3, preferably 0 or 1.

It may preferably be the case that the sum total of the indices n is not more than 4, preferably not more than 2, more preferably not more than 1 and especially preferably 0.

The $Z^a$, $Z^b$, $Z^c$ group is the same or different and is Cl, Br, I, $B(OR)_2$, OH, $OSO_2R$, $Si(R)_3$ or an alkoxy or thioalkoxy group having 1 to 20, preferably having 1 to 10 and especially preferably having 1, 2, 3 or 4 carbon atoms, preferably Cl, Br, I, $B(OR)_2$, OH, $OSO_2R$, more preferably Cl, Br, I, $B(OR)_2$, especially preferably Cl, Br, I. More preferably, at least one of the $Z^a$, $Z^b$, $Z^c$ groups is Br and at least one further $Z^a$, $Z^b$, $Z^c$ group is $C_1$. In a further embodiment, at least one of the $Z^a$, $Z^b$, $Z^c$ groups is I and at least one further $Z^a$, $Z^b$, $Z^c$ group is Br. It may preferably be the case that two of the $Z^a$, $Z^b$, $Z^c$ groups are Br and the third of the $Z^a$, $Z^b$, $Z^c$ groups is Cl.

The substituents R shown in the $B(OR)_2$, $OSO_2R$, $Si(R)_3$ groups of the $Z^a$, $Z^b$, $Z^c$ radicals are preferably selected from a straight-chain alkyl group having 1 to 10, preferably having 1, 2, 3 or 4, carbon atoms, or an alkenyl group having 2 to 10, preferably having 2, 3 or 4, carbon atoms, or a branched or cyclic alkyl group having 3 to 10, preferably having 3, 4 or 5, carbon atoms.

When two R radicals or $R^1$ together with $R^2$ or together with one of the $R^a$ or $R^b$ or $R^c$ radicals form a ring system, it may be mono- or polycyclic, aliphatic, heteroaliphatic, aromatic or heteroaromatic. In this case, the radicals which together form a ring system may be adjacent, meaning that these radicals are bonded to the same carbon atom or to carbon atoms directly bonded to one another, or they may be further removed from one another.

When X is CR or when the aromatic and/or heteroaromatic groups are substituted by substituents R, $R^a$, $R^b$, $R^c$, these R, $R^a$, $R^b$, $R^c$ radicals are the same or different at each instance and are preferably selected from the group consisting of H, D, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may be substituted in each case by one or more $R^1$ radicals, or an aromatic or heteroaromatic ring system which has 5 to 30 aromatic ring atoms and may be substituted in each case by one or more $R^1$ radicals; at the same time, two adjacent R radicals together or R together with $R^1$ may also form a ring system.

More preferably, these substituents R, $R^a$, $R^b$, $R^c$ are selected from the group consisting of H, D, a straight-chain alkyl group having 1 to 8 carbon atoms, preferably having 1, 2, 3 or 4 carbon atoms, or a branched or cyclic alkyl group having 3 to 8 carbon atoms, preferably having 3, 4, 5 or 6 carbon atoms, or an alkenyl group having 2 to 8 carbon atoms, preferably having 2, 3 or 4 carbon atoms, each of which may be substituted by one or more $R^1$ radicals, but is preferably unsubstituted, or an aromatic or heteroaromatic ring system which has 5 to 24 aromatic ring atoms, preferably 6 to 18 aromatic ring atoms, more preferably 6 to 13 aromatic ring atoms, and may be substituted in each case by one or more nonaromatic $R^1$ radicals, but is preferably unsubstituted; at the same time, it is optionally possible for two R substituents, preferably bonded to adjacent carbon atoms, or one substituent R together with one of the substituents $R^a$, $R^b$, $R^c$, to form a monocyclic or polycyclic aliphatic ring system which may be substituted by one or more $R^1$ radicals, but is preferably unsubstituted.

Most preferably, the substituents R, $R^a$, $R^b$, $R^c$ are selected from the group consisting of H and an aromatic or heteroaromatic ring system which has 6 to 18 aromatic ring atoms, preferably 6 to 13 aromatic ring atoms, and may be substituted in each case by one or more nonaromatic $R^1$ radicals, but is preferably unsubstituted. Examples of suitable substituents R, $R^a$, $R^b$, $R^c$ are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^1$ radicals, but are preferably unsubstituted.

It may further be the case that at least one of the $R^a$, $R^b$, $R^c$ groups is selected from a straight-chain alkyl, alkoxy or thioalkoxy group having 1 to 20 carbon atoms, preferably 1 to 10 carbon atoms, or an alkenyl or alkynyl group having 2 to 20 carbon atoms, preferably 2 to 10 carbon atoms, or a branched or cyclic alkyl, alkoxy or thioalkoxy group having 3 to 20 carbon atoms, preferably 3 to 10 carbon atoms, where the alkyl, alkoxy, thioalkoxy, alkenyl or alkynyl group in each case may be substituted by one or more $R^1$ radicals, or an aromatic or heteroaromatic ring system which has 5 to 40 aromatic ring atoms, preferably 6 to 24 aromatic ring atoms, and may be substituted in each case by one or more $R^1$ radicals, or an aryloxy or heteroaryloxy group having 5 to 40 aromatic ring atoms.

It may preferably be the case that not more than one of the R groups per ring and preferably none of the R groups is F, Cl, Br, I, $B(OR^1)_2$, OH, $OSO_2R^1$, $Si(R^1)_3$ or an alkoxy or thioalkoxy group having 1 to 20 carbon atoms. More preferably, not more than one of the R groups per ring and preferably none of the R groups is F, Cl, Br, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$ or an alkoxy or thioalkoxy group having 1 to 20 carbon atoms. Corresponding preferences are also applicable to the $R^1$ groups that are bonded to R, where the $R^1$ radicals mentioned should be replaced here by $R^2$.

It may further be the case that not more than one of the $R^a$, $R^b$, $R^c$ groups and preferably none of the $R^a$, $R^b$, $R^c$ groups is F, Cl, Br, I, $B(OR^1)_2$, OH, $OSO_2R^1$, $Si(R^1)_3$ or an alkoxy or thioalkoxy group having 1 to 20 carbon atoms. More preferably, not more than one of the $R^a$, $R^b$, $R^c$ groups and preferably none of the $R^a$, $R^b$, $R^c$ groups is F, Cl, Br, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$ or an alkoxy or thioalkoxy group having 1 to 20 carbon atoms. Corresponding preferences are also applicable to the $R^1$ groups that are bonded to $R^a$, $R^b$ or $R^c$, where the $R^1$ radicals mentioned should be replaced here by $R^2$.

Preferred $R^1$ radicals bonded to R, $R^a$, $R^b$, $R^c$ are the same or different at each instance and are H, D, a straight-chain alkyl group having 1 to 10 carbon atoms or an alkenyl group having 2 to 10 carbon atoms or a branched or cyclic alkyl group having 3 to 10 carbon atoms, where the alkyl group may be substituted in each case by one or more $R^2$ radicals, or an aromatic or heteroaromatic ring system which has 5 to 24 aromatic ring atoms and may be substituted in each case by one or more $R^2$ radicals; at the same time, two or more adjacent $R^1$ radicals together may form a mono- or polycyclic aliphatic ring system. Particularly preferred $R^1$ radicals bonded to R, $R^a$, $R^b$, $R^c$ are the same or different at each instance and are H, F, CN, a straight-chain alkyl group having 1 to 5 carbon atoms or a branched or cyclic alkyl group having 3 to 5 carbon atoms, each of which may be substituted by one or more $R^2$ radicals, or an aromatic or heteroaromatic ring system which has 5 to 13 aromatic ring atoms and may be substituted in each case by one or more $R^2$ radicals; at the same time, two or more adjacent $R^1$ radicals together may form a mono- or polycyclic aliphatic ring system.

Preferred $R^2$ radicals are the same or different at each instance and are H, D or an aliphatic hydrocarbyl radical having 1 to 5 carbon atoms or an aromatic hydrocarbyl radical having 6 to 12 carbon atoms; at the same time, two or more $R^2$ substituents together may also form a mono- or polycyclic aliphatic ring system.

The inventive compounds of the formula (I) and the preferred embodiments detailed above can be prepared by conventional methods from known reactants that are in many cases commercially available.

For example, aromatic or heteroaromatic acetophenone derivatives can be condensed as detailed, for example, in the publication JP 2000-169400.

In the synthesis scheme which follows, the compounds are shown with a small number of substituents to simplify the structures. This does not rule out the presence of any desired further substituents in the processes.

An illustrative implementation is given by Scheme 1 below, without any intention that this should impose a restriction.

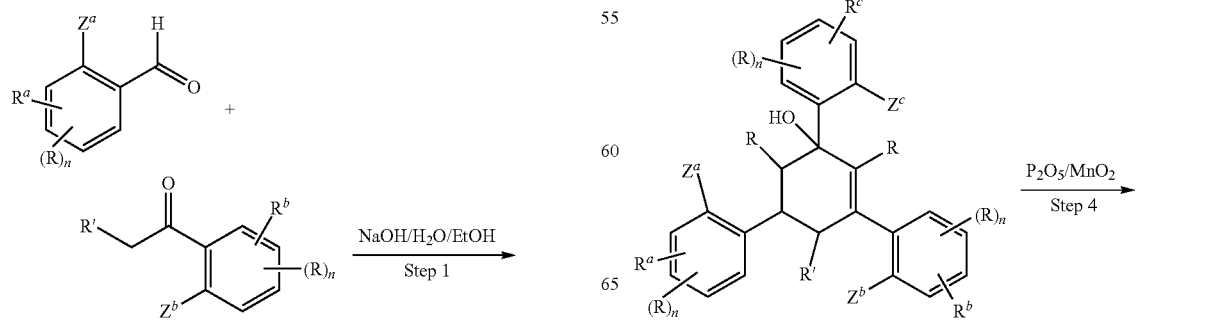

Scheme 1

-continued

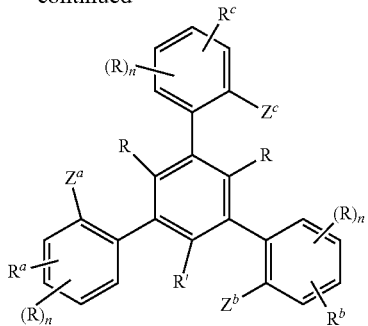

The definition of the symbols used in Scheme 1 corresponds essentially to that as defined for formula (I).

The process shown for synthesis of the compounds of the invention should be understood by way of example. The person skilled in the art will be able to develop alternative synthesis routes within the scope of his common knowledge in the art.

The principles of the preparation processes detailed above are known in principle from the literature for similar compounds and can be adapted easily by the person skilled in the art to the preparation of the compounds of the invention. Further information can be found in the examples.

The compounds of the invention are especially appropriate for preparation of polydentate ligands, preferably tripodal hexadentate ligands. These polydentate ligands, preferably tripodal hexadentate ligands, preferably comprise a bridge derived from the compounds of the invention, and sub-ligands that can coordinate to a metal atom, preferably to iridium. These ligands can preferably serve to produce metal complexes, especially rhodium complexes, which can be used as emitters in phosphorescent organic electroluminescent devices.

Therefore, the present invention further provides a process for preparing a bridged ligand, in which a compound of the invention is reacted in a first step with a first reactive ligand in a coupling reaction and the product obtained is reacted in a second step with a second reactive ligand in a coupling reaction, where the first and second reactive ligands are different, such that a bridge is formed between a sub-ligand derived from the first reactive ligand and a sub-ligand derived from the second reactive ligand.

The first reactive ligand differs from the second reactive ligand. The difference is visible in the sub-ligands present in the bridged ligand after the reaction. Thus, a difference in the reactive group of the reactive ligands is insufficient to count as a difference between these ligands.

As a result of the use of different reactive ligands, preferably different reactive bidentate ligands, asymmetric bridged ligands are obtained.

The bridged ligands obtainable in accordance with the invention do not have $C_3$ symmetry, and preferably do not have $C_{3v}$ symmetry. Preferably, the bridged ligands obtainable have a symmetry of point group $C_s$ or $C_1$. These point groups are common knowledge and are described, for example, in Atkins, Child, & Phillips: Tables for Group Theory, Oxford University Press, 2006.

In one configuration of the process of the invention, it may be the case that the second step is followed by performance of a third step, wherein the product obtained after the second step is reacted with a further reactive ligand in a coupling reaction, where the first, second and third reactive ligands are different. In this context, the difference is detectable in the sub-ligands of the bridged ligand.

Preferably, the reactive ligands have two potential coordination sites, and so they can be regarded as bidentate ligands. Preferably at least one of the reactive ligands is a bidentate ligand, more preferably at least two of the reactive ligands are bidentate ligands, and most preferably all three of the reactive ligands are bidentate ligands.

In a preferred environment of the invention, two of the reactive bidentate ligands chosen are the same and the third reactive bidentate ligand differs from the first two bidentate ligands.

The atoms of the bidentate ligands that coordinate to a metal here may be the same or different at each instance and may be selected from C, N, P, O, S and/or B, more preferably C, N and/or O and most preferably C and/or N. The bidentate ligands preferably have one carbon atom and one nitrogen atom or two carbon atoms or two nitrogen atoms or two oxygen atoms or one oxygen atom and one nitrogen atom as atoms that can coordinate to a metal. In this case, the coordinating atoms of each of the ligands may be the same, or they may be different. Preferably at least one of the bidentate sub-ligands has, more preferably all the bidentate sub-ligands have, one carbon atom and one nitrogen atom or two carbon atoms as coordinating atoms, especially one carbon atom and one nitrogen atom. More preferably at least two of the bidentate ligands and most preferably all three bidentate ligands have one carbon atom and one nitrogen atom or two carbon atoms as coordinating atoms, especially one carbon atom and one nitrogen atom.

It is further preferable when the metallacycle which can be formed from the metal and the bidentate ligand is a five-membered ring, which is preferable particularly when the coordinating atoms are C and N, C and C, N and N, or N and O. When the coordinating atoms are O, a six-membered metallacyclic ring may also be preferred. This is shown schematically hereinafter:

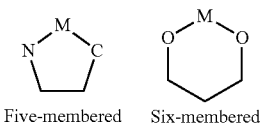

Five-membered    Six-membered where N is a coordinating nitrogen atom, C is a coordinating carbon atom and O represents coordinating oxygen atoms, and the carbon atoms shown are atoms of the bidentate ligand.

In a preferred embodiment of the invention, at least one of the reactive bidentate ligands, more preferably at least two of the reactive bidentate ligands, most preferably all three reactive bidentate ligands, are the same or different at each instance and are selected from the structures of the following formulae (L-1), (L-2) and (L-3):

Formula (L-1)

Formula (L-2)

Formula (L-3)

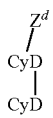

where the symbols used are as follows:

CyC is the same or different at each instance and is a substituted or unsubstituted aryl or heteroaryl group which has 5 to 14 aromatic ring atoms and can coordinate in each case to a metal via a carbon atom and which is bonded in each case to CyD via a covalent bond; the optional substituents here are preferably selected from R, where R has the definitions given above, especially for formula (I);

CyD is the same or different at each instance and is a substituted or unsubstituted heteroaryl group which has 5 to 14 aromatic ring atoms and can coordinate to a metal via a nitrogen atom or via a carbene carbon atom and which is bonded to CyC via a covalent bond; the optional substituents here are preferably selected from R, where R has the definitions given above, especially for formula (I);

$Z^d$ is a reactive group, preferably Cl, Br, I, B(OR)$_2$, OH, OSO$_2$R or an alkoxy or thioalkoxy group having 1 to 20 carbon atoms, preferably Cl, Br, I, B(OR)$_2$, OH, OSO$_2$R, more preferably Cl, Br, I, B(OR)$_2$, especially preferably Cl, Br, I, where R has the definitions given above, especially for formula (I).

At the same time, the CyD group in the reactive ligands of the formulae (L-1) and (L-2) can preferably coordinate via an uncharged nitrogen atom or via a carbene carbon atom. Further preferably, one of the two CyD groups in the ligand of the formula (L-3) can coordinate via an uncharged nitrogen atom and the other of the two CyD groups via an anionic nitrogen atom. Further preferably, CyC in the ligands of the formulae (L-1) and (L-2) can coordinate via anionic carbon atoms.

When two or more of the substituents, especially two or more R radicals, together form a ring system, it is possible for a ring system to be formed from substituents bonded to directly adjacent carbon atoms. In addition, it is also possible that the substituents on CyC and CyD in the formulae (L-1) and (L-2) or the substituents on the two CyD groups in formula (L-3) together form a ring, as a result of which CyC and CyD or the two CyD groups or the two CyC groups may also together form a single fused aryl or heteroaryl group as bidentate ligand.

In a preferred embodiment of the present invention, CyC is an aryl or heteroaryl group having 6 to 13 aromatic ring atoms, more preferably having 6 to 10 aromatic ring atoms, most preferably having 6 aromatic ring atoms, which coordinates to the metal via a carbon atom, which may be substituted by one or more R radicals and which is bonded to CyD via a covalent bond.

Preferred embodiments of the CyC group are the structures of the following formulae (CyC-1) to (CyC-20):

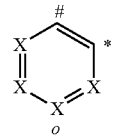 (CyC-1)

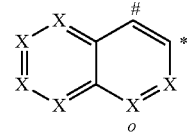 (CyC-2)

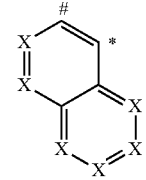 (CyC-3)

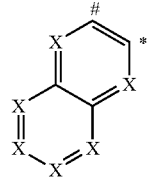 (CyC-4)

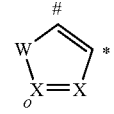 (CyC-5)

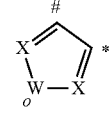 (CyC-6)

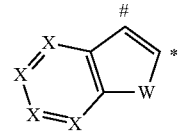 (CyC-7)

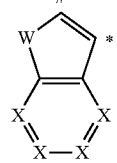 (CyC-8)

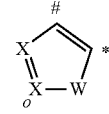 (CyC-9)

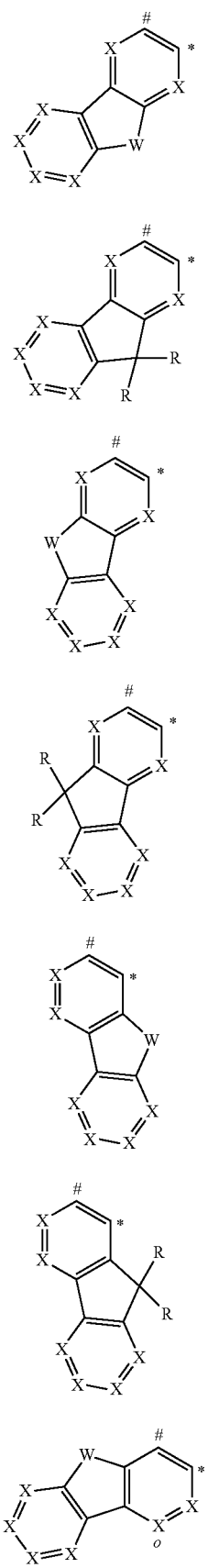
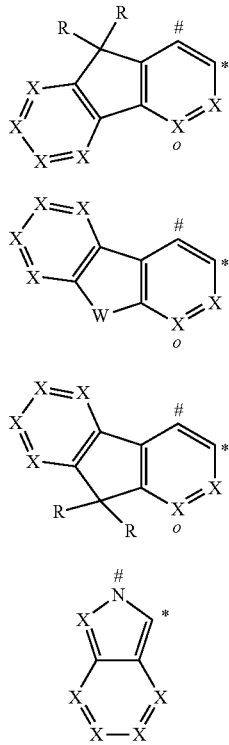

where CyC binds in each case to the position in CyD indicated by # and R has the definitions given above and the further symbols used are as follows:

X is the same or different at each instance and is CR or N, where preferably not more than two X symbols per cycle are N;

W is NR, O or S;

where the ligands may be bonded via the CyC group by a bridge, where the bond to the bridge can preferably be via the position marked "o", where the position marked "o" represents a carbon atom if it is a bridgehead site and the ligands can be coordinated to a metal atom, in which case the ligand coordinates to the metal at the position identified by *. When the CyC group is to be bonded to the bridge of the formula (I), the bond is preferably via the position marked "o" in the formulae depicted above, and so the symbol X marked "o" in that case is preferably C. The above-depicted structures which do not contain any symbol X marked "o" are preferably not bonded directly to the bridge of the formula (I), since such a bond to the bridge is not advantageous for steric reasons.

By way of clarification, it should be stated that preferred reactive ligands that can be reacted with the compounds of the invention contain at least one group of the above-detailed formulae CyC and/or CyD. It may preferably be the case here that the reactive ligand is joined to an inventive compound of formula (I) via one of these groups. This linkage site is generally represented herein by the symbol °. Before the reaction, there is preferably a reactive group at this site, which is generally represented herein by $Z^d$. On the other hand, a reactive ligand preferably comprises exactly one reactive group which is reacted with an inventive compound of formula (I). Therefore, above and hereinafter, the possible linkage site for the bond to a bridge which is detailed for the CyC and CyD groups is described by the symbol °.

Preferably, a total of not more than two symbols X in CyC are N, more preferably not more than one symbol X in CyC is N, and especially preferably all symbols X are CR, with the proviso that, when CyC is bonded to a bridge, one symbol X is C and the bridge is bonded to this carbon atom.

Particularly preferred CyC groups are the groups of the following formulae (CyC-1a) to (CyC-20a):

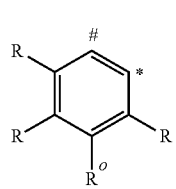
(CyC-1a)

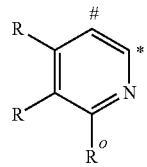
(CyC-1b)

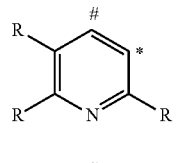
(CyC-1c)

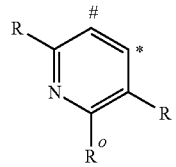
(CyC-1d)

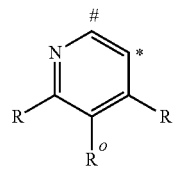
(CyC-1e)

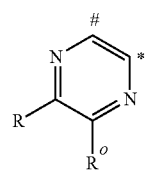
(CyC-1f)

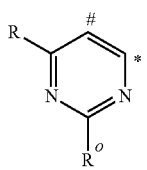
(CyC-1g)

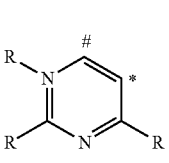
(CyC-1h)

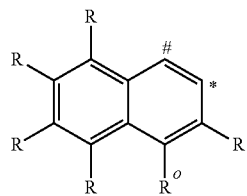
(CyC-2a)

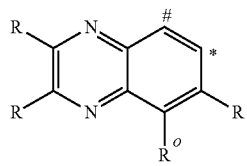
(CyC-2b)

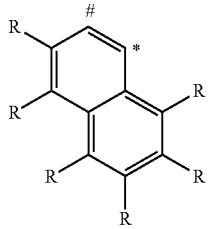
(CyC-3a)

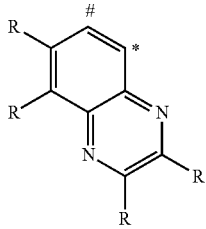
(CyC-3b)

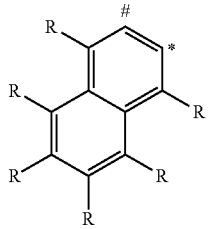
(CyC-4a)

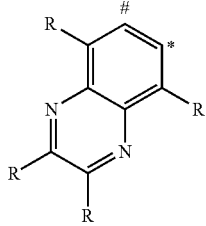
(CyC-4b)

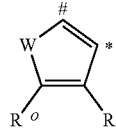
(CyC-5a)

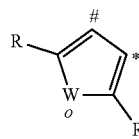 (CyC-6a)
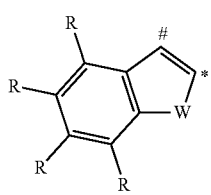 (CyC-7a)
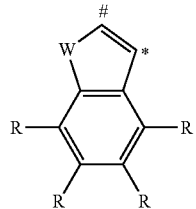 (CyC-8a)
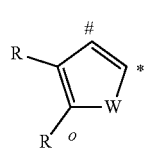 (CyC-9a)
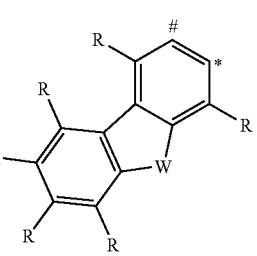 (CyC-10a)
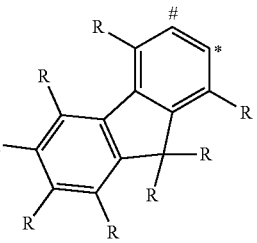 (CyC-11a)
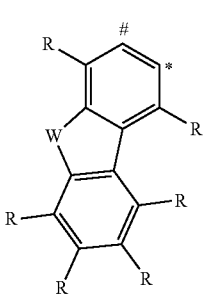 (CyC-12a)
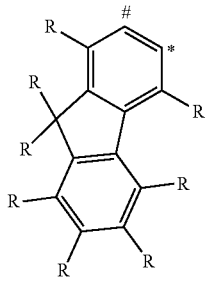 (CyC-13a)
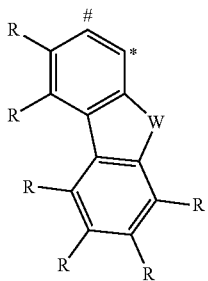 (CyC-14a)
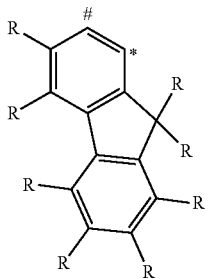 (CyC-15a)
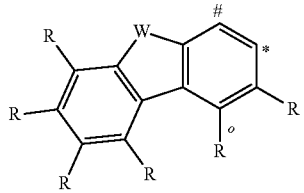 (CyC-16a)
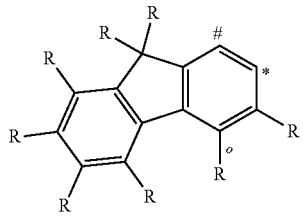 (CyC-17a)
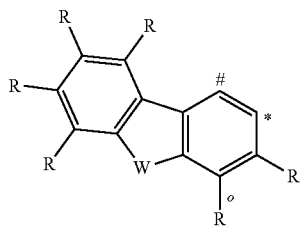 (CyC-18a)

-continued

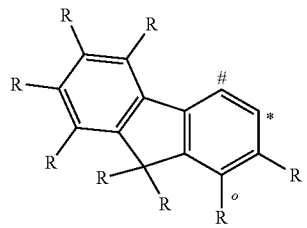
(CyC-19a)

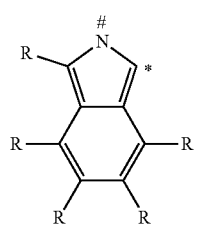
(CyC-20a)

where the symbols have the definitions given above and, when the bridge is bonded to CyC, one R radical is absent and the bridge is bonded to the corresponding carbon atom. When a CyC group is bonded to a bridge, the bond is preferably via the position marked "o" in the formulae depicted above, and so the R radical in this position in that case is preferably absent. The above-depicted structures which do not contain any carbon atom marked "o" are preferably not bonded directly to a bridge.

Preferred groups among the (CyC-1) to (CyC-19) groups are the (CyC-1), (CyC-3), (CyC-8), (CyC-10), (CyC-12), (CyC-13) and (CyC-16) groups, and particular preference is given to the (CyC-1a), (CyC-3a), (CyC-8a), (CyC-10a), (CyC-12a), (CyC-13a) and (CyC-16a) groups.

In a further preferred embodiment of the invention, CyD is a heteroaryl group having 5 to 13 aromatic ring atoms, more preferably having 6 to 10 aromatic ring atoms, which coordinates to the metal via an uncharged nitrogen atom or via a carbene carbon atom and which may be substituted by one or more R radicals and which is bonded via a covalent bond to CyC.

Preferred embodiments of the CyD group are the structures of the following formulae (CyD-1) to (CyD-14):

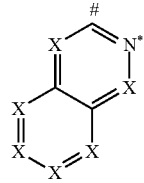
(CyD-1)

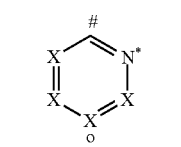
(CyD-2)

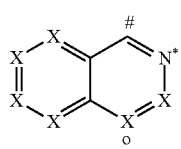
(CyD-3)

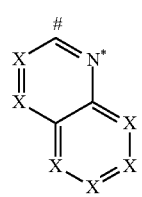
(CyD-4)

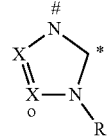
(CyD-5)

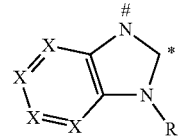
(CyD-6)

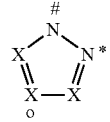
(CyD-7)

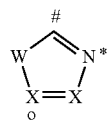
(CyD-8)

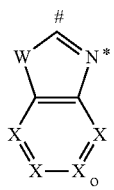
(CyD-9)

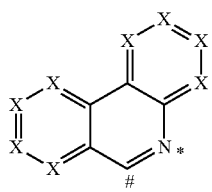
(CyD-10)

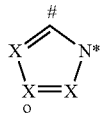
(CyD-11)

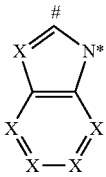
(CyD-12)

(CyD-13)

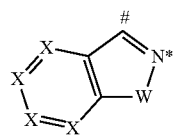

(CyD-14)

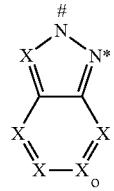

where the CyD group binds to CyC in each case at the position identified by #, where X, W and R have the definitions given above and where the ligands may be bonded by a bridge via the CyD group, where the bond to the bridge of the formula (I) is preferably via the position marked "o", where the position marked "o" represents a carbon atom if it represents a bridgehead site and the ligands may be coordinated to a metal atom, in which case the ligand coordinates to the metal at the position identified by *. When the CyD group is bonded to the bridge of the formula (I), the bond is preferably via the position marked by "o" in the formulae depicted above, and so the symbol X marked by "o" in that case is preferably C. The above-depicted structures which do not contain any symbol X marked "o" are preferably not bonded directly to the bridge of the formula (I), since such a bond to the bridge is not advantageous for steric reasons.

In this case, the (CyD-1) to (CyD-4), (CyD-7) to (CyD-10), (CyD-13) and (CyD-14) groups can coordinate to the metal via an uncharged nitrogen atom, the (CyD-5) and (CyD-6) groups via a carbene carbon atom and the (CyD-11) and (CyD-12) groups via an anionic nitrogen atom.

Preferably, a total of not more than two symbols X in CyD are N, more preferably not more than one symbol X in CyD is N, and especially preferably all symbols X are CR, with the proviso that, when CyD is bonded to a bridge, one symbol X is C and the bridge is bonded to this carbon atom.

Particularly preferred CyD groups are the groups of the following formulae (CyD-1a) to (CyD-14b):

(CyD-1a)

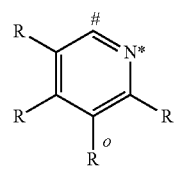

(CyD-2a)

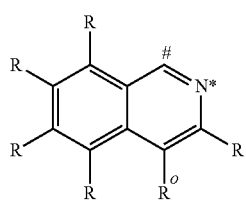

(CyD-3a)

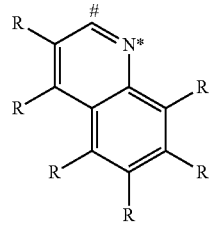

(CyD-3b)

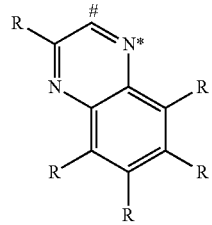

(CyD-4a)

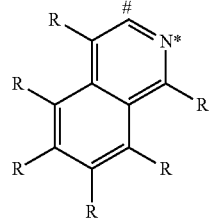

(CyD-5a)

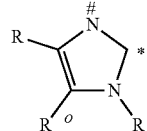

(CyD-6a)

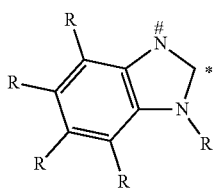

(CyD-7a)

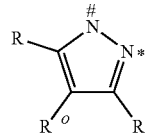

(CyD-8a)

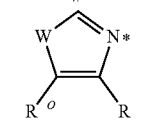

(CyD-9a)

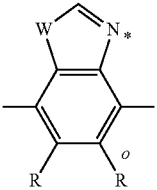

-continued (CyD-10a)
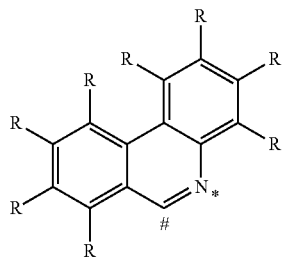

(CyD-11a)
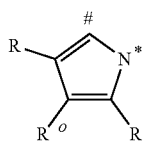

(CyD-11b)
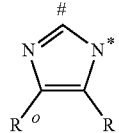

(CyD-11c)
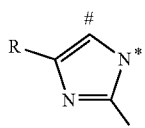

(CyD-11d)
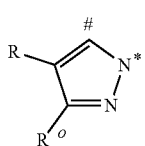

(CyD-12a)
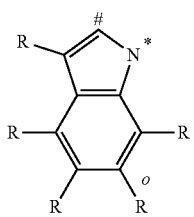

(CyD-12b)
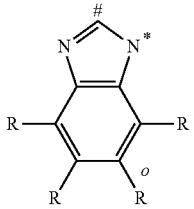

(CyD-13a)
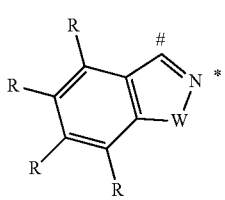

-continued (CyD-14a)
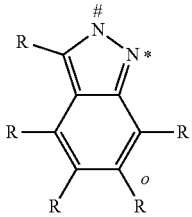

(CyD-14b)
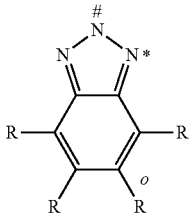

where the symbols used have the definitions given above and, when the bridge is bonded to CyD, one R radical is absent and the bridge is bonded to the corresponding carbon atom. When the CyD group is bonded to a bridge, the bond is preferably via the position marked "o" in the formulae depicted above, and so the R radical in this position in that case is preferably absent. The above-depicted structures which do not contain any carbon atom marked "o" are preferably not bonded directly to a bridge.

Preferred groups among the (CyD-1) to (CyD-10) groups are the (CyD-1), (CyD-2), (CyD-3), (CyD-4), (CyD-5) and (CyD-6) groups, especially (CyD-1), (CyD-2) and (CyD-3), and particular preference is given to the (CyD-1a), (CyD-2a), (CyD-3a), (CyD-4a), (CyD-5a) and (CyD-6a) groups, especially (CyD-1a), (CyD-2a) and (CyD-3a).

In a preferred embodiment of the present invention, CyC is an aryl or heteroaryl group having 6 to 13 aromatic ring atoms, and at the same time CyD is a heteroaryl group having 5 to 13 aromatic ring atoms. More preferably, CyC is an aryl or heteroaryl group having 6 to 10 aromatic ring atoms, and at the same time CyD is a heteroaryl group having 5 to 10 aromatic ring atoms. Most preferably, CyC is an aryl or heteroaryl group having 6 aromatic ring atoms, and CyD is a heteroaryl group having 6 to 10 aromatic ring atoms. At the same time, CyC and CyD may be substituted by one or more R radicals.

The abovementioned preferred groups (CyC-1) to (CyC-20) and (CyD-1) to (CyD-14) may be combined with one another as desired in the ligands of the formulae (L-1) and (L-2). In this case, at least one of the CyC or CyD groups has a suitable attachment site to a bridge, where suitable attachment sites in the abovementioned formula are identified by "o". At this point, prior to the reaction with an inventive compound of formula (I), there is preferably a reactive group which is generally represented herein by $Z^d$. It is especially preferable when the CyC and CyD groups mentioned as particularly preferred above, i.e. the groups of the formulae (CyC-1a) to (CyC-20a) and the groups of the formulae (CyD1-a) to (CyD-14b), are combined with one another.

It is very particularly preferable when one of the (CyC-1), (CyC-3), (CyC-8), (CyC-10), (CyC-12), (CyC-13) and (CyC-16) groups and especially the (CyC-1a), (CyC-3a), (CyC-8a), (CyC-10a), (CyC-12a), (CyC-13a) and (CyC-16a) groups is combined with one of the (CyD-1), (CyD-2) and (CyD-3) groups and especially with one of the (CyD-1a), (CyD-2a) and (CyD-3a) groups.

Preferred reactive bidentate ligands (L-1) are the structures of the following formulae (L-1-1) and (L-1-2), and preferred ligands (L-2) are the structures of the following formulae (L-2-1) to (L-2-3):

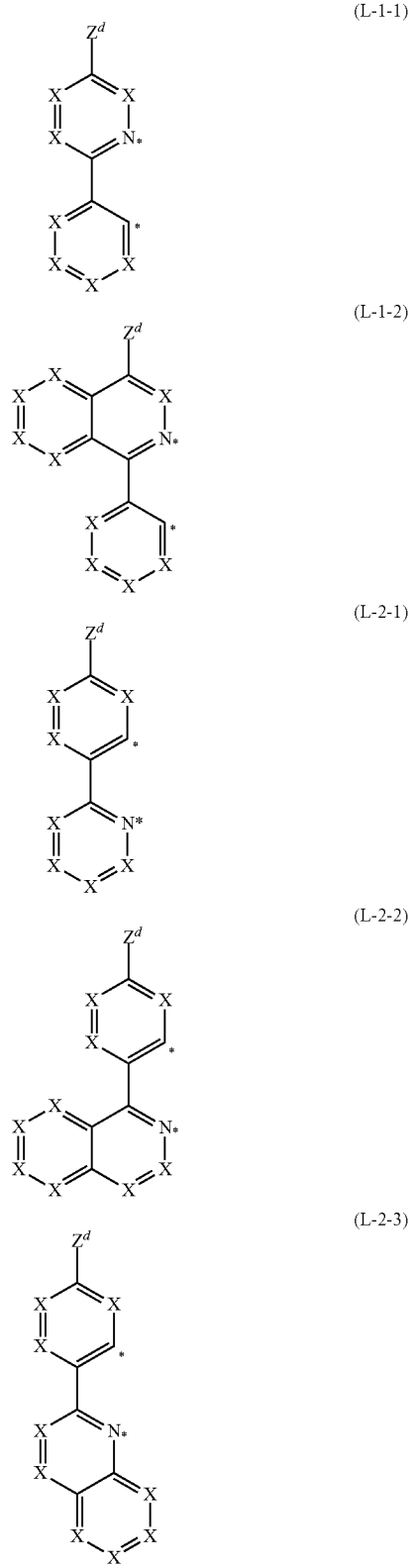

where the symbols used have the definitions given above and the ligands can be coordinated to a metal atom, in which case the ligand coordinates to the metal at the position identified by *.

Particularly preferred ligands (L-1) are the structures of the following formulae (L-1-1a) and (L-1-2b), and particularly preferred ligands (L-2) are the structures of the following formulae (L-2-1a) to (L-2-3a):

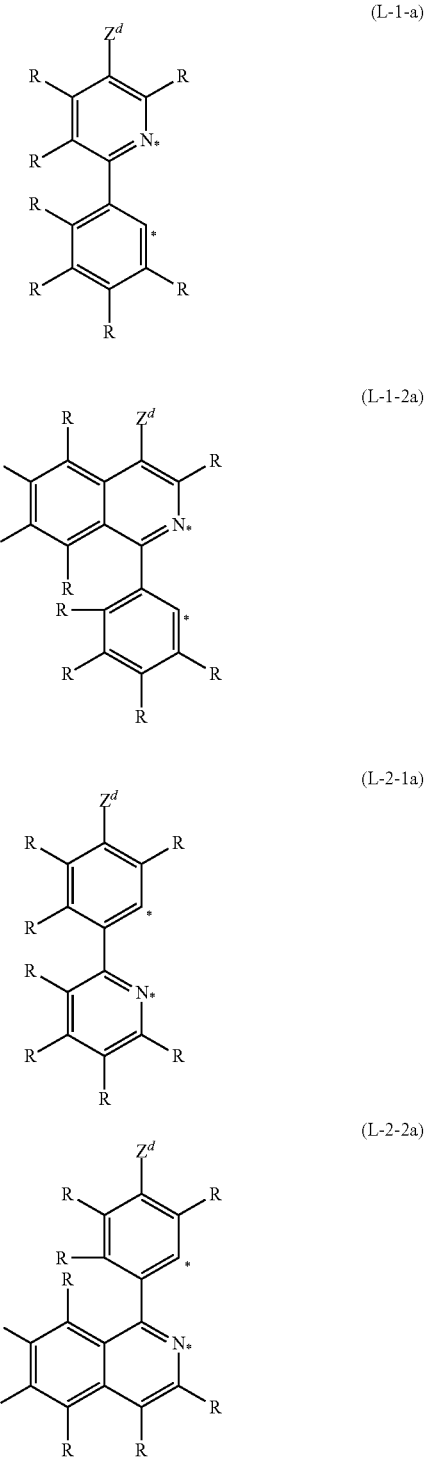

-continued

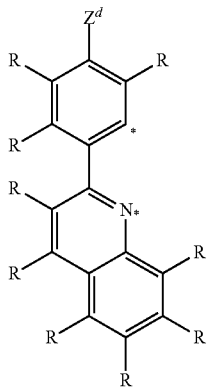
(L-2-3a)

where the symbols used have the definitions given above and the ligands can be coordinated to a metal atom, in which case the ligand coordinates to the metal at the position identified by *.

The abovementioned preferred CyD groups can likewise be combined with one another as desired in the ligands of the formula (L-3), it being preferable to combine an uncharged CyD group, i.e. a (CyD-1) to (CyD-10), (CyD-13) or (CyD-14) group, with an anionic CyD group, i.e. a (CyD-11) or (CyD-12) group.

When two R radicals, one of them bonded to CyC and the other to CyD in the formulae (L-1) and (L-2) or one of them bonded to one CyD group and the other to the other CyD group in formula (L-3), form an aromatic ring system with one another, this may result in bridged ligands and, for example, also in ligands which constitute a single larger heteroaryl group overall, for example benzo[h]quinoline, etc. The ring formation between the substituents on CyC and CyD in the formulae (L-1) and (L-2) or between the substituents on the two CyD groups in formula (L-3) is preferably via a group according to one of the following formulae (RB-1) to (RB-10):

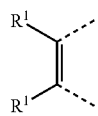
Formula (RB-1)

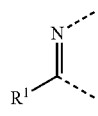
Formula (RB-2)

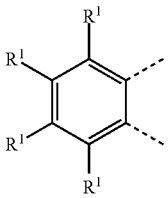
Formula (RB-3)

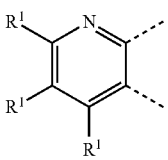
Formula (RB-4)

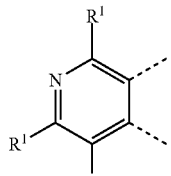
Formula (RB-5)

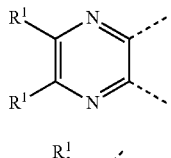
Formula (RB-6)

Formula (RB-7)

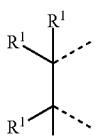
Formula (RB-8)

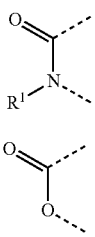
Formula (RB-9)

Formula (RB-10)

where $R^1$ has the definitions given above and the dotted bonds signify the bonds to CyC or CyD. At the same time, the unsymmetric groups among those mentioned above may be incorporated in each of the two options; for example, in the group of the formula (RB-10), the oxygen atom may bind to the CyC group and the carbonyl group to the CyD group, or the oxygen atom may bind to the CyD group and the carbonyl group to the CyC group.

At the same time, the group of the formula (RB-7) is preferred particularly when this results in ring formation to give a six-membered ring, as shown below, for example, by the formulae (L-23) and (L-24).

Preferred reactive ligands which arise through ring formation between two R radicals in the different cycles are the structures of the formulae (L-4) to (L-31) shown below:

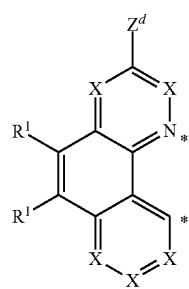
(L-4)

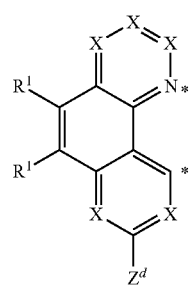 (L-5)
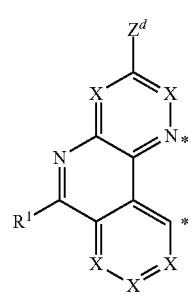 (L-6)
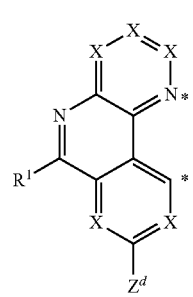 (L-7)
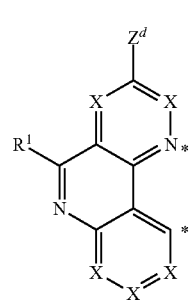 (L-8)
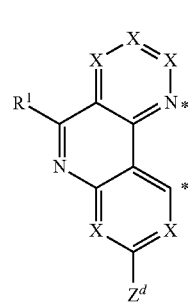 (L-9)
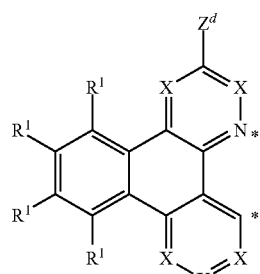 (L-10)
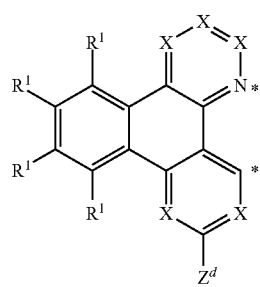 (L-11)
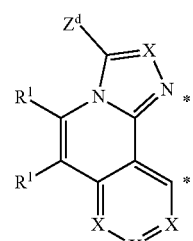 (L-12)
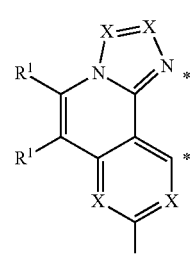 (L-13)
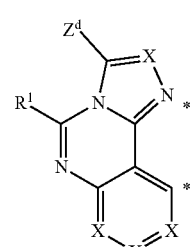 (L-14)
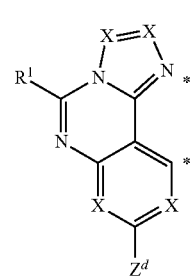 (L-15)

(L-16)
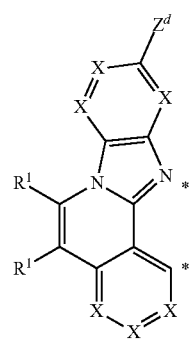
(L-17)
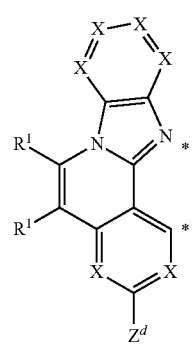
(L-18)
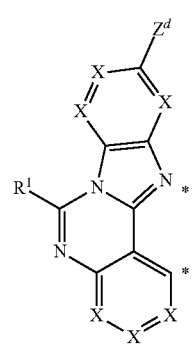
(L-19)
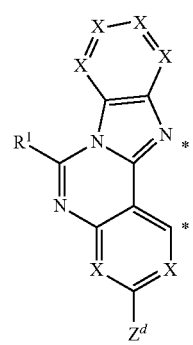
(L-20)
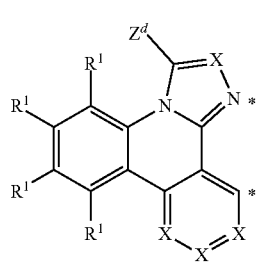
(L-21)
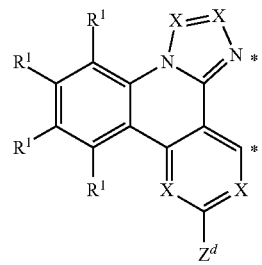
(L-22)
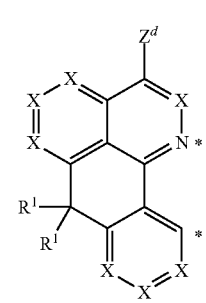
(L-23)
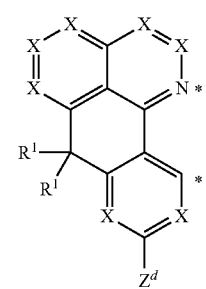
(L-24)
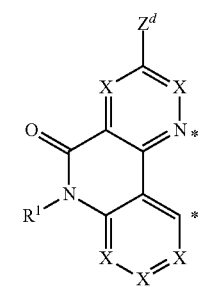
(L-25)
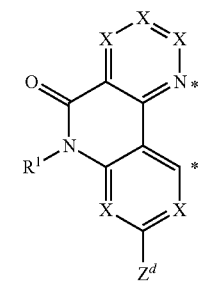

(L-26) 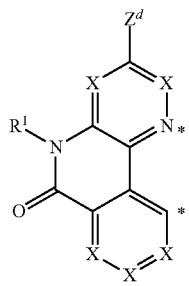

(L-27) 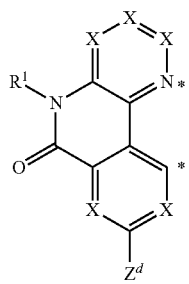

(L-28) 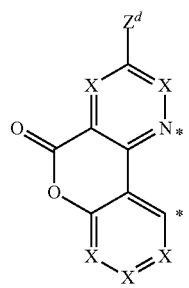

(L-29) 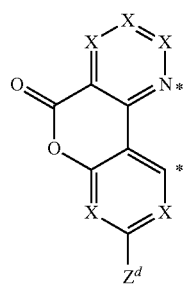

(L30) 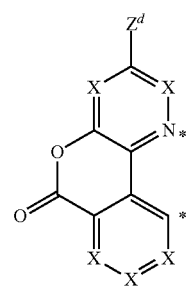

(L-31) 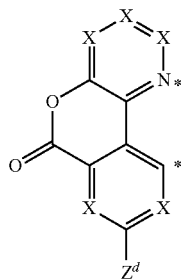

where the symbols used have the definitions given above and the ligands can be coordinated to a metal atom, in which case the ligand coordinates to the metal at the position identified by *.

In a preferred embodiment of the ligands of the formulae (L-4) to (L-31), a total of one symbol X is N and the other symbols X are CR, or all symbols X are CR.

In a further embodiment of the invention, it is preferable if, in the groups (CyC-1) to (CyC-20) or (CyD-1) to (CyD-14) or in the ligands (L-4) to (L-31), one of the atoms X is N when an R group bonded as a substituent adjacent to this nitrogen atom is not hydrogen or deuterium. This applies analogously to the preferred structures (CyC-1a) to (CyC-20a) or (CyD-1a) to (CyD-14b) in which a substituent bonded adjacent to a non-coordinating nitrogen atom is preferably an R group which is not hydrogen or deuterium. This substituent R is preferably a group selected from $CF_3$, $OCF_3$, alkyl or alkoxy groups having 1 to 10 carbon atoms, especially branched or cyclic alkyl or alkoxy groups having 3 to 10 carbon atoms, a dialkylamino group having 2 to 10 carbon atoms, aromatic or heteroaromatic ring systems or aralkyl or heteroaralkyl groups. These groups are sterically demanding groups. Further preferably, this R radical may also form a cycle with an adjacent R radical.

A further suitable reactive bidentate ligand is the ligand of the following formula (L-32) or (L-33)

(L-32) 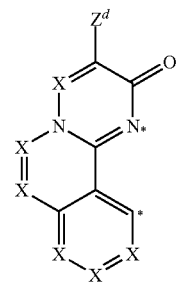

(L-33) 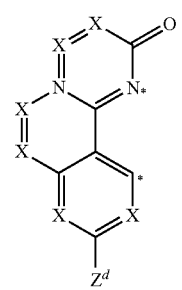

where X and $Z^d$ have the definitions given above, with the proviso that not more than one symbol X per cycle is N, and ligands can be coordinated to a metal atom, where the ligand coordinates to the metal at the position identified by *.

When two R radicals bonded to adjacent carbon atoms in the ligands (L-32) and (L-33) form an aromatic cycle with one another, this cycle together with the two adjacent carbon atoms is preferably a structure of the following formula (RB-11):

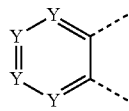

Formula (RB-11)

where the dotted bonds symbolize the linkage of this group within the ligand and Y is the same or different at each instance and is $CR^1$ or N and preferably not more than one symbol Y is N.

In a preferred embodiment of the ligand (L-32) or (L-33), not more than one group of the formula (BR-11) is present. The ligands are thus preferably ligands of the following formulae (L-34) to (L-39):

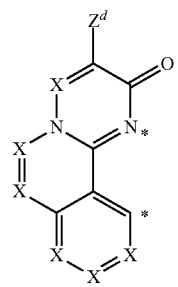
(L-34)

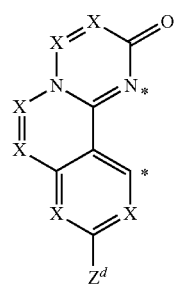
(L-35)

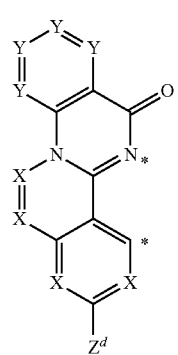
(L-36)

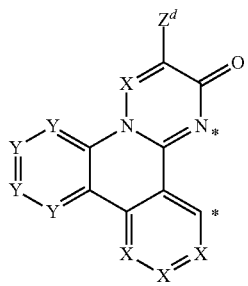
(L-37)

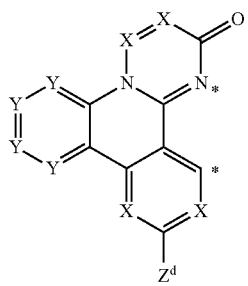
(L-38)

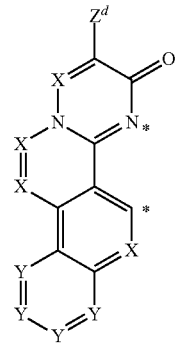
(L-39)

where X is the same or different at each instance and is CR or N, but the R radicals do not form an aromatic or heteroaromatic ring system with one another and the further symbols have the definitions given above, with the proviso that not more than one symbol X per cycle is N, and the ligands can be coordinated to a metal atom, in which case the ligand coordinates to the metal at the position identified by *.

In a preferred embodiment of the invention, in the ligand of the formulae (L-32) to (L-39), a total of 0, 1 or 2 of the symbols X and, if present, Y are N. More preferably, a total of 0 or 1 of the symbols X and, if present, Y are N.

In a preferred embodiment of the invention, the X group in the ortho position to the coordination to the metal is CR. In this radical, R bonded in the ortho position to the coordination to the metal is preferably selected from the group consisting of H, D, F and methyl.

In a further embodiment of the invention, it is preferable, if one of the atoms X or, if present, Y is N, when a substituent bonded adjacent to this nitrogen atom is an R group which is not hydrogen or deuterium. This substituent R is preferably a group selected from $CF_3$, $OCF_3$, alkyl or alkoxy groups having 1 to 10 carbon atoms, especially branched or cyclic alkyl or alkoxy groups having 3 to 10 carbon atoms, a dialkylamino group having 2 to 10 carbon atoms, aromatic or heteroaromatic ring systems or aralkyl or heteroaralkyl groups. These groups are sterically demanding groups. Further preferably, this R radical may also form a cycle with an adjacent R radical.

Further suitable reactive bidentate ligands are the structures of the following formulae (L-40) to (L-44):

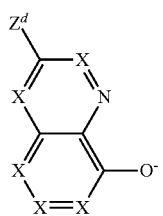
(L-40)

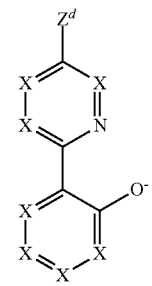
(L-41)

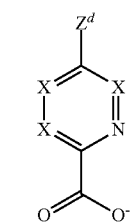
(L-42)

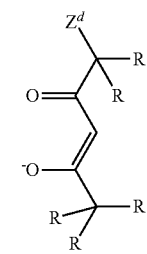
(L-43)

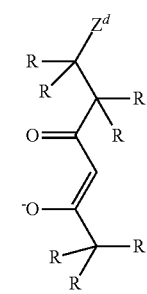
(L-44)

where the ligands (L-40) to (L-42) can each coordinate to a metal via the nitrogen atom explicitly shown and the negatively charged oxygen atom, and the ligands (L-43) and (L-44) via the two oxygen atoms, X and $Z^d$ have the definitions given above.

The above-recited preferred embodiments of X are also preferred for the ligands of the formulae (L-40) to (L-42).

Preferred ligands of the formulae (L-40) to (L-42) are therefore the ligands of the following formulae (L-40a) to (L-42a):

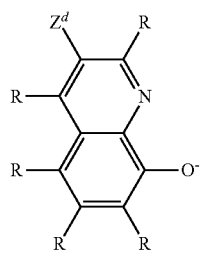
(L-40a)

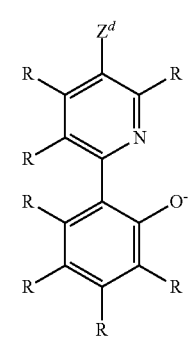
(L-41a)

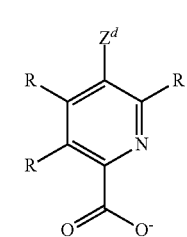
(L-42a)

where the symbols used have the definitions given above.

More preferably, in these formulae, R is hydrogen, and so the structures are those of the following formulae (L-40b) to (L-41 b):

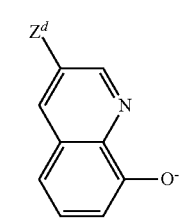
(L-40b)

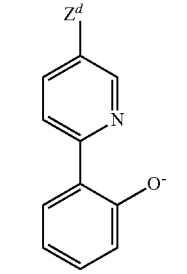
(L-41b)

-continued

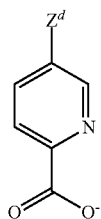

(L-42b)

where the symbols used have the definitions given above.

Preference is given to converting an inventive compound of the formula (I) having not more than one of the structures of the formulae (L-40) to (L-44), such that two of the reactive ligands with which an inventive compound of the formula (I) is preferably reacted in order to obtain preferred polydentate ligands differ from the structures of the formulae (L-40) to (L-44).

The preferences detailed above for the structure (I) with regard to the R, $R^1$ and $R^2$ radicals are also correspondingly applicable to the bidentate sub-ligands or ligands or the preferred embodiments thereof detailed above.

The preparation of bridged ligands using inventive compounds of formula (I) and reactive ligands, preferably reactive bidentate ligands of the above-detailed formulae (L-1) to (L-42), is preferably effected by coupling reactions.

Coupling reactions suitable for this purpose are common knowledge, the necessary conditions for this purpose being known to the person skilled in the art, and detailed specifications in the examples give support to the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

The process for preparing the polypodal ligands from the inventive compounds of the formula (I) is shown schematically below in Scheme 2.

Scheme 2a shows the synthesis of a polypodal ligand having two identical sub-ligands L1 and L2 and a further sub-ligand L3 different from the first two sub-ligands, and Scheme 2b shows the synthesis of a polypodal ligand having three different sub-ligands L1, L2 and L3.

Scheme 2 a)

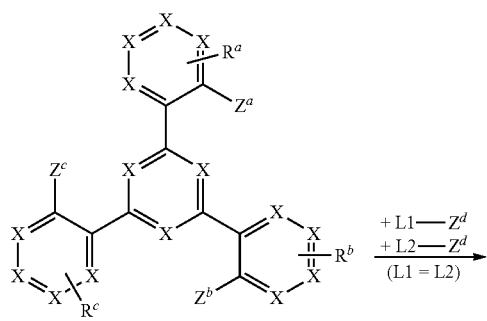

-continued

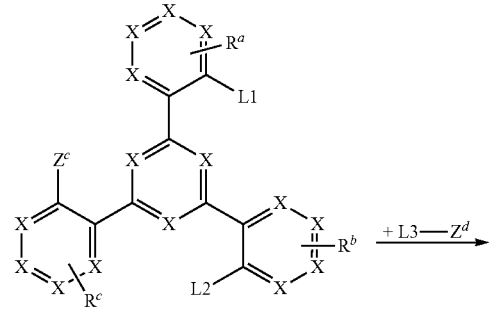

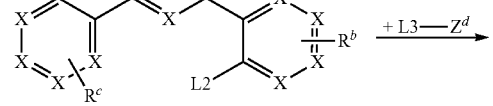

b)

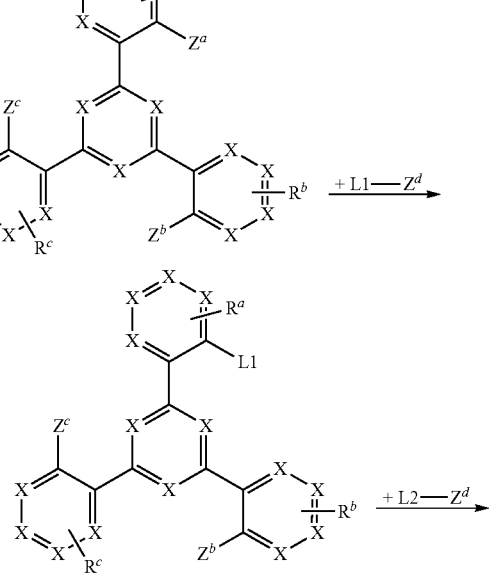

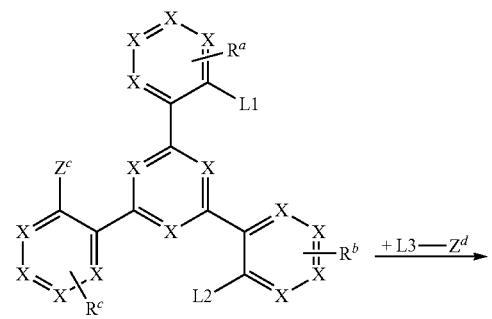

-continued

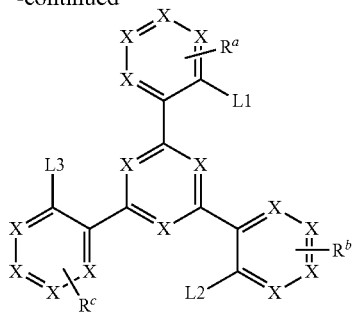

It is possible by these processes, if necessary followed by purification, for example recrystallization or sublimation, to obtain the above-detailed inventive compounds of the formula (I) and the bridged ligands obtainable therefrom in high purity, preferably more than 99% (determined by means of $^1$H NMR and/or HPLC).

The bridged ligands obtainable in accordance with the invention may also be rendered soluble by suitable substitution, for example by comparatively long alkyl groups (about 4 to 20 carbon atoms), especially branched alkyl groups, or optionally substituted aryl groups, for example xylyl, mesityl or branched terphenyl or quaterphenyl groups. The use of fused-on aliphatic groups in particular also leads to a distinct improvement in the solubility of the bridged ligands and of the metal complexes obtainable therefrom. Such compounds are then soluble in sufficient concentration at room temperature in standard organic solvents, for example toluene or xylene, to be able to process the complexes from solution. These soluble compounds are of particularly good suitability for processing from solution, for example by printing methods.

There follows a description of preferred metal complexes which can be prepared with the hexadentate ligands obtainable in accordance with the invention. As described above, these are organometallic complexes. An organometallic complex in the context of the present invention is a complex having at least one metal-carbon bond to the ligand. In a preferred embodiment, the metal complex is uncharged, i.e. electrically neutral.

The bond of the ligand to the metal may either be a coordinate bond or a covalent bond, or the covalent fraction of the bond may vary according to the ligand. When it is said in the present application that the ligand coordinates or binds to the metal, this refers in the context of the present application to any kind of bond of the ligand to the metal, irrespective of the covalent component of the bond.

In a preferred embodiment, the metal is iridium. It may be the case here that the metal is Ir(III) and a metal complex has three bidentate sub-ligands L1, L2 and L3, where two of the bidentate sub-ligands coordinate to the iridium via one carbon atom and one nitrogen atom in each case or via two carbon atoms, and the third of the bidentate sub-ligands coordinates to the iridium via one carbon atom and one nitrogen atom or via two carbon atoms or via two nitrogen atoms, where preferably the third of the bidentate ligands coordinates to the iridium via one carbon atom and one nitrogen atom or via two carbon atoms.

The structure of the hexadentate tripodal ligands can be shown in schematic form by the following formula (Lig):

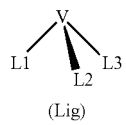

(Lig)

where V represents the bridge of the formula (I) after reaction with the ligands, i.e. the compounds of the formula (I) that no longer contain the $Z^a$, $Z^b$ and $Z^c$ groups, and L1, L2 and L3 are the same or different at each instance and are each bidentate sub-ligands, preferably mono bidentate sub-ligands. "Bidentate" means that the particular ligand in the complex M(Lig) coordinates or binds to the iridium via two coordination sites. "Tripodal" means that the ligand has three sub-ligands L1, L2 and L3 that are bonded to the bridge V. Since the ligand has three bidentate sub-ligands, the overall result is a hexadentate ligand, i.e. a ligand which coordinates or binds to the iridium via six coordination sites. The expression "bidentate sub-ligand" in the context of this application means that this unit would be a bidentate ligand if the bridge were absent. However, as a result of the formal abstraction of a hydrogen atom in this bidentate ligand and the attachment to the bridge, it is not a separate ligand but a portion of the hexadentate ligand which thus arises, and so the term "sub-ligand" is used therefor.

The iridium complex M(Lig) formed with this ligand of the formula (Lig) can thus be represented schematically by the following formula:

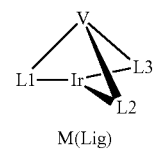

M(Lig)

where V, L1, L2 and L3 have the same definitions as described above.

The metal complexes can be prepared by various processes. Iridium complexes can be obtained by reaction of the corresponding free ligands with metal alkoxides of the formula (Ir-1), with metal ketoketonates of the formula (Ir-2), with metal halides of the formula (Ir-3) or with metal carboxylates of the formula (Ir-4)

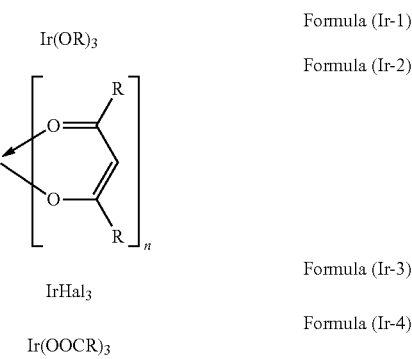

where R has the definitions given above, Hal=F, Cl, Br or I and the iridium reactants may also take the form of the corresponding hydrates. R here is preferably an alkyl group having 1 to 4 carbon atoms.

It is likewise possible to use iridium compounds bearing both alkoxide and/or halide and/or hydroxyl and ketoketonate radicals. These compounds may also be charged. Corresponding iridium compounds of particular suitability as reactants are disclosed in WO 2004/085449. Particularly suitable are [IrCl$_2$(acac)$_2$]$^-$, for example Na[IrCl$_2$(acac)$_2$], metal complexes with acetylacetonate derivatives as ligand, for example Ir(acac)$_3$ or tris(2,2,6,6-tetramethylheptane-3,5-dionato)iridium, and IrCl$_3$.xH$_2$O where x is typically a number from 2 to 4.

The synthesis of complexes is preferably conducted as described in WO 2002/060910 and in WO 2004/085449. In this case, the synthesis can, for example, also be activated by thermal or photochemical means and/or by microwave radiation. In addition, the synthesis can also be conducted in an autoclave at elevated pressure and/or elevated temperature.

The reactions can be conducted without addition of solvents or melting aids in a melt of the corresponding ligands to be o-metallated. It is optionally possible to add solvents or melting aids. Suitable solvents are protic or aprotic solvents such as aliphatic and/or aromatic alcohols (methanol, ethanol, isopropanol, t-butanol, etc.), oligo- and polyalcohols (ethylene glycol, propane-1,2-diol, glycerol, etc.), alcohol ethers (ethoxyethanol, diethylene glycol, triethylene glycol, polyethylene glycol, etc.), ethers (di- and triethylene glycol dimethyl ether, diphenyl ether, etc.), aromatic, heteroaromatic and/or aliphatic hydrocarbons (toluene, xylene, mesitylene, chlorobenzene, pyridine, lutidine, quinoline, isoquinoline, tridecane, hexadecane, etc.), amides (DMF, DMAC, etc.), lactams (NMP), sulphoxides (DMSO) or sulfones (dimethyl sulfone, sulfolane, etc.). Suitable melting aids are compounds that are in solid form at room temperature but melt when the reaction mixture is heated and dissolve the reactants, so as to form a homogeneous melt. Particularly suitable are biphenyl, m-terphenyl, triphenyls, R- or S-binaphthol or else the corresponding racemate, 1,2-, 1,3- or 1,4-bisphenoxybenzene, triphenylphosphine oxide, 18-crown-6, phenol, 1-naphthol, hydroquinone, etc. Particular preference is given here to the use of hydroquinone.

For the processing of the metal complexes obtainable in accordance with the invention from the liquid phase, for example by spin-coating or by printing methods, formulations of the metal complexes of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The metal complexes obtainable in accordance with the invention can be used in the form of a composition with at least one further functional material. Functional materials are generally the organic or inorganic materials introduced between the anode and cathode. Preferably, the functional material is selected from the group consisting of fluorescent emitters, phosphorescent emitters, host materials, electron transport materials, electron injection materials, hole conductor materials, hole injection materials, electron blocker materials, hole blocker materials, wide band gap materials and n-dopants.

The above-described metal complex obtainable in accordance with the invention or the preferred embodiments detailed above can be used in the electronic device as active component or as oxygen sensitizers or in photocatalysis. In this case, the metal complex can preferably be used as a phosphorescent emitter.

An electronic device is understood to mean any device comprising anode, cathode and at least one layer, said layer comprising at least one organic or organometallic compound. The electronic device thus comprises anode, cathode and at least one layer containing at least one metal complex obtainable in accordance with the invention. Preferred electronic devices are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), the latter being understood to mean both purely organic solar cells and dye-sensitized solar cells, organic optical detectors, organic photoreceptors, organic field-quench devices (O-FQDs), light-emitting electrochemical cells (LECs), oxygen sensors and organic laser diodes (O-lasers), comprising at least one metal complex of the invention in at least one layer. Particular preference is given to organic electroluminescent devices. Active components are generally the organic or inorganic materials introduced between the anode and cathode, for example charge injection, charge transport or charge blocker materials, but especially emission materials and matrix materials. The metal complexes obtainable in accordance with the invention exhibit particularly good properties as emission material in organic electroluminescent devices. In addition, the compounds can be used for production of singlet oxygen or in photocatalysis. Especially when the metal is ruthenium, preference is given to use as a photosensitizer in a dye-sensitized solar cell ("Grätzel cell").

The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as MoO$_3$ or WO$_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce. White-emitting organic electroluminescent devices may be used for lighting applications or else with colour filters for full-colour displays.

Preferably, the metal complex obtainable in accordance with the invention is used as emitting compound in one or more emitting layers. When the metal complex obtainable in accordance with the invention is used as emitting compound in an emitting layer, it is preferably used in combination with one or more matrix materials. The mixture of the metal complex and the matrix material contains between 0.1% and 99% by weight, preferably between 1% and 90% by weight, more preferably between 3% and 40% by weight and especially between 5% and 25% by weight of the metal complex, based on the overall mixture of emitter and matrix material. Correspondingly, the mixture contains between 99.9% and 1% by weight, preferably between 99% and 10% by weight, more preferably between 97% and 60% by weight and especially between 95% and 75% by weight of the matrix material, based on the overall mixture of emitter and matrix material.

The matrix material used may generally be any materials which are known for the purpose according to the prior art. The triplet level of the matrix material is preferably higher than the triplet level of the emitter. Suitable matrix materials are ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015 or WO 2015/169412, or bridged carbazole derivatives, for example according to US 2009/0136779, WO 2010/050778, WO 2011/042107 or WO 2011/088877. It may also be preferable to use multiple different matrix materials as a mixture, especially at least one electron-conducting matrix material and at least one hole-conducting matrix material, for example a triazine derivative in combination with a triarylamine derivative or a carbazole derivative. Preference is likewise given to the use of a mixture of a charge-transporting matrix material and an electrically inert matrix material having no significant involvement, if any, in the charge transport, as described, for example, in WO 2010/108579. Preference is likewise given to the use of two electron-transporting matrix materials, for example triazine derivatives and lactam derivatives, as described, for example, in WO 2014/094964.

It is further preferable to use a mixture of two or more triplet emitters together with a matrix. In this case, the triplet emitter having the shorter-wave emission spectrum serves as co-matrix for the triplet emitter having the longer-wave emission spectrum. For example, it is possible to use the metal complexes obtainable in accordance with the invention as co-matrix for longer-wave-emitting triplet emitters, for example for green- or red-emitting triplet emitters. In this case, it may also be preferable when both the shorter-wave- and the longer-wave-emitting metal complexes are a compound obtainable in accordance with the invention.

The metal complexes obtainable in accordance with the invention can also be used in other functions in the electronic device, for example as hole transport material in a hole injection or transport layer, as charge generation material, as electron blocker material, as hole blocker material or as electron transport material, for example in an electron transport layer, according to the choice of metal and the exact structure of the ligand. When the metal complex obtainable in accordance with the invention is an aluminium complex, it is preferably used in an electron transport layer. It is likewise possible to use the metal complexes obtainable in accordance with the invention as matrix material for other phosphorescent metal complexes in an emitting layer.

Materials used in the further layers may generally be any as used for the layers according to the prior art.

The organic electroluminescent device can be produced by various processes. More particularly, one or more layers may be coated by a sublimation process, or one or more layers may be coated by the OVPD (organic vapour phase deposition) process or with the aid of carrier gas sublimation, or one or more layers may be produced from solution, for example by spin-coating, or by any printing process, for example screenprinting, flexographic printing, offset printing, nozzle printing, LITI (light-induced thermal imaging, thermal transfer printing) or inkjet printing. The organic electroluminescent device can likewise also be produced as a hybrid system by applying one or more layers from solution and applying one or more other layers by vapour deposition. For example, it is possible to apply an emitting layer comprising a metal complex obtainable in accordance with the invention and a matrix material from solution, and to apply a hole blocker layer and/or an electron transport layer thereto by vapour deposition under reduced pressure. These methods are known in general terms to the person skilled in the art, who is able to apply them without difficulty to organic electroluminescent devices or the preferred embodiments detailed above.

The compounds of the invention and the ligands, metal complexes and electronic devices obtainable therefrom, especially organic electroluminescent devices, are notable for one or more of the following surprising advantages over the prior art:

1. The compounds of the invention enables simple and inexpensive preparation of asymmetric ligands. These ligands are obtained here in high yields and in high purity.
2. The ligands and metal complexes obtainable in accordance with the invention can be synthesized from the compounds of the invention in very high yield and very high purity with exceptionally short reaction times and at comparatively low reaction temperatures.

3. The ligands obtainable in accordance with the invention have excellent processability. For example, these ligands have higher solubility than comparable ligands having higher symmetry. In addition, the ligands obtainable in accordance with the invention have better sublimability than comparable ligands having higher symmetry. Improved access to the ligands obtainable in accordance with the invention is a distinct technical advantage.

4. The metal complexes obtainable in accordance with the invention have very good processability from solution and excellent solubility in many organic solvents. In addition, the metal complexes obtainable in accordance with the invention exhibit very good sublimability. Improved access to the metal complexes obtainable in accordance with the invention is a distinct technical advantage.

The invention is illustrated in more detail by the examples which follow, without any intention of restricting it thereby. The person skilled in the art will be able to use the details given, without exercising inventive skill, to prepare further compounds of the invention and use them for synthesis of ligands and metal complexes, and will thus be able to execute the invention over the entire scope claimed.

EXAMPLES

The syntheses which follow, unless stated otherwise, are conducted under a protective gas atmosphere in dried solvents. The solvents and reagents can be purchased, for example, from Sigma-ALDRICH or ABCR. The respective figures in square brackets or the numbers quoted for individual compounds relate to the CAS numbers of the compounds known from the literature.

Synthesis of the Synthons S and of the Inventive Compounds P

Step 1

Example S1

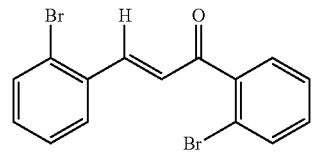 [SMILES: O=C(/C=C/c1ccccc1Br)c1ccccc1Br]

To a well-stirred solution, cooled to 15° C., of 5.0 g (125 mmol) of NaOH in a mixture of 50 ml of water and 30 ml of ethanol are added 19.8 g (100 mmol) of 2'-bromoacetophenone [2142-69-0] and then 18.5 g (100 mmol) of 2-bromobenzaldehyde [6030-33-7]. The reaction mixture is allowed to warm up to room temperature and stirred for a further 24 h. The reaction mixture is then cooled down to about −10° C. in an ice/salt bath, and a viscous yellow oil separates out. The supernatant solvent is decanted off, the oil is taken up in 300 ml of dichloromethane (DCM), and the organic phase is washed three times with 100 ml each time of water and once with 100 ml of saturated sodium chloride solution and then dried over magnesium sulfate. After the solvent has been removed under reduced pressure, a viscous oil is obtained, which crystallizes when left to stand. Yield: 34.8 g (95 mmol), 95%; purity: about 97% by $^1$H NMR.

In an analogous manner, it is possible to prepare the following compounds:

| Ex. | Reactants | Product / Solvent added to the reaction | Yield |
|---|---|---|---|
| S2 | 26260-02-6<br>2142-69-0 | | 95% |
| S3 | 135-02-4<br>2142-69-0 | | 95% |
| S4 | 17887-55-7<br>2142-69-0 | | 90% |

-continued
| Ex. | Reactants | Product Solvent added to the reaction | Yield |
|---|---|---|---|
| S5 | 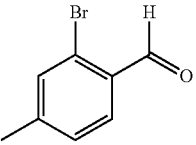 824-54-4 2142-69-0 | 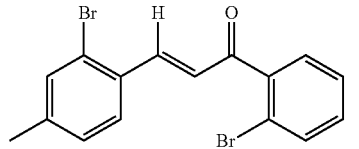 [SMILES: Cc1ccc(/C=C/C(=O)c2ccccc2Br)c(Br)c1] | 96% |
| S6 | 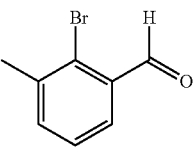 109179-31-9 2142-69-0 | 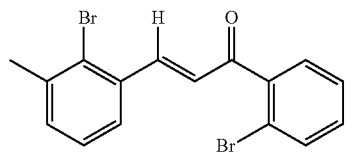 [SMILES: Cc1cccc(/C=C/C(=O)c2ccccc2Br)c1Br] | 95% |
| S7 | 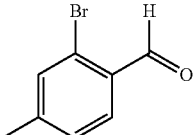 1450812-17-5 2142-69-0 | 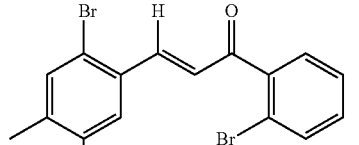 | 93% |
| S8 | 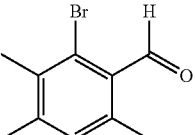 88174-34-9 2142-69-0 | 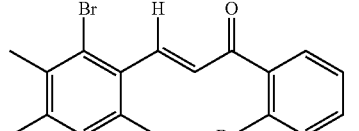 | 83% |
| S9 | 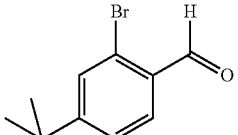 246139-77-5 2142-69-0 | 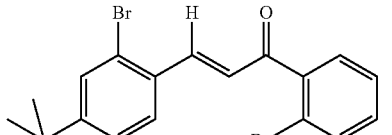 | 94% |
| S10 | 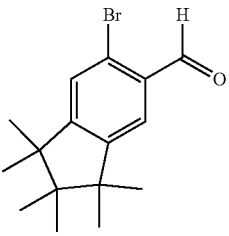 1562418-68-1 2142-69-0 | 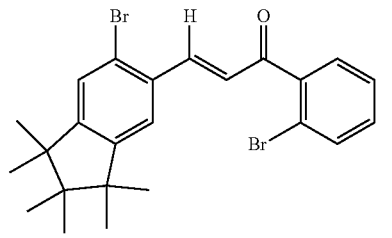 Addition of 30 ml of THF | 92% |

-continued
| Ex. | Reactants | Product Solvent added to the reaction | Yield |
|---|---|---|---|
| S11 | 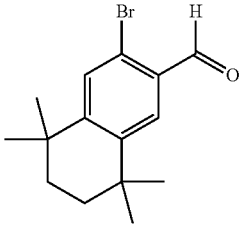<br>410528-63-1<br>2142-69-0 | 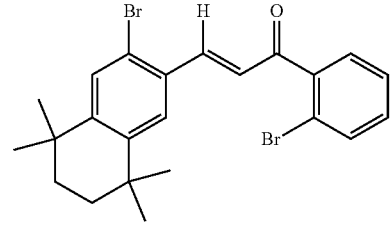<br>Addition of 30 ml of THF | 95% |
| S12 | 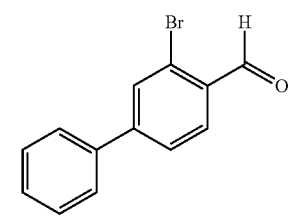<br>1237125-81-3<br>2142-69-0 | 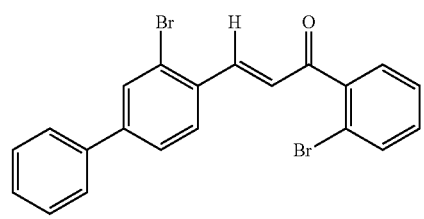 [SMILES: O=C(/C=C/c1ccc(-c2ccccc2)cc1Br)c1ccccc1Br] | 97% |
| S13 | 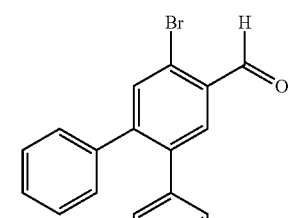<br>1620010-52-7<br>2142-69-0 | 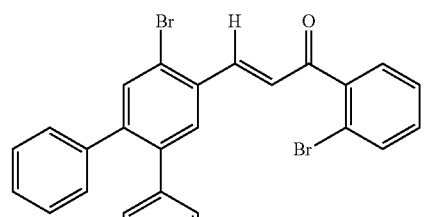<br>Addition of 30 ml of THF | 95% |
| S14 | 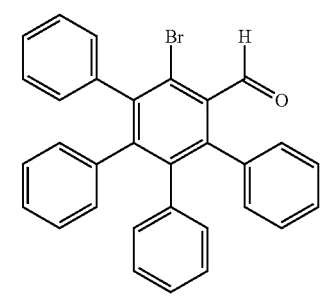<br>1620010-72-1<br>2142-69-0 | 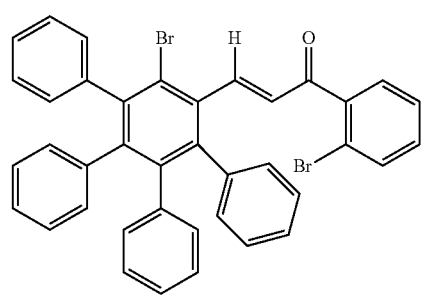<br>Addition of 30 ml of THF | 78% |
| S15 | 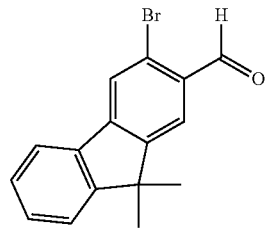<br>1205547-17-6<br>2142-69-0 | 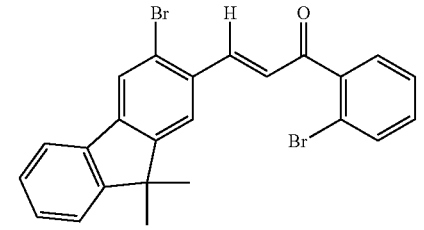 [SMILES: CC1(C)c2ccccc2-c2cc(Br)c(/C=C/C(=O)c3ccccc3Br)cc21] | 93% |

-continued
| Ex. | Reactants | Product Solvent added to the reaction | Yield |
|---|---|---|---|
| S16 | 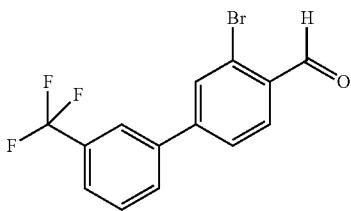 1237080-18-0 2142-69-0 | 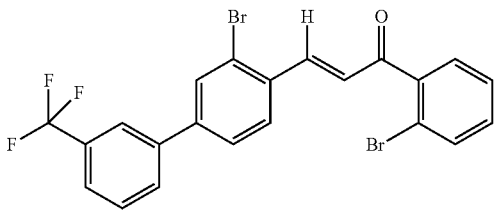 Addition of 30 ml of THF | 90% |
| S17 | 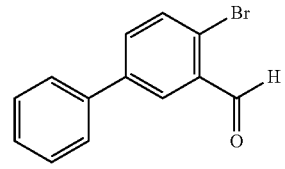 1237107-66-2 2142-69-0 | 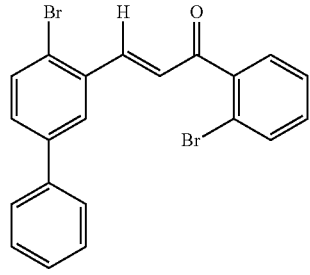 [SMILES: O=C(/C=C/c1cc(-c2ccccc2)ccc1Br)c1ccccc1Br] | 89% |
| S18 | 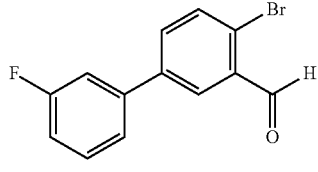 18994461-77-8 2142-69-0 | 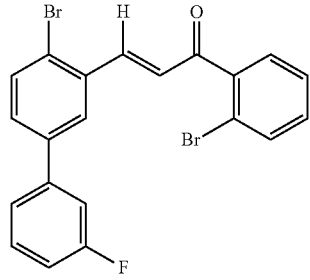 [SMILES: O=C(/C=C/c1cc(-c2cccc(F)c2)ccc1Br)c1ccccc1Br] | 94% |
| S19 | 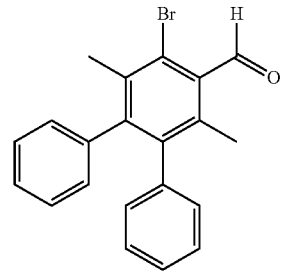 1620010-77-6 2142-69-0 | 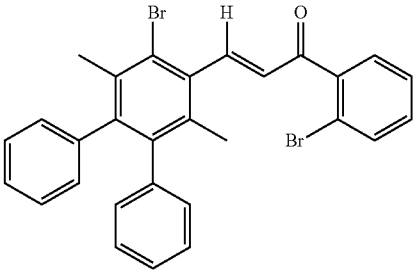 [SMILES: Cc1c(Br)c(/C=C/C(=O)c2ccccc2Br)c(C)c(-c2ccccc2)c1-c1ccccc1] | 81% |
| S20 | 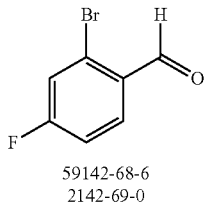 59142-68-6 2142-69-0 | 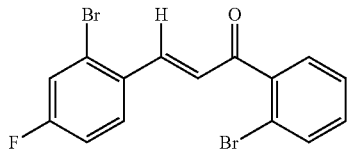 [SMILES: O=C(/C=C/c1ccc(F)cc1Br)c1ccccc1Br] | 98% |

-continued
| Ex. | Reactants | Product Solvent added to the reaction | Yield |
|---|---|---|---|
| S21 | 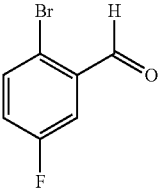 94569-84-3 2142-69-0 | 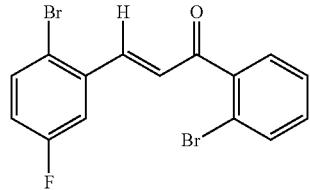 [SMILES: O=C(/C=C/c1cc(F)ccc1Br)c1ccccc1Br] | 96% |
| S22 | 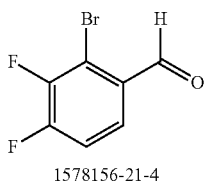 1578156-21-4 2142-69-0 | 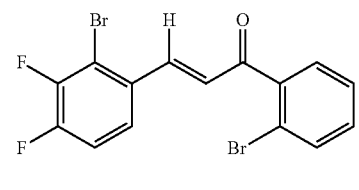 [SMILES: O=C(/C=C/c1ccc(F)c(F)c1Br)c1ccccc1Br] | 93% |
| S23 | 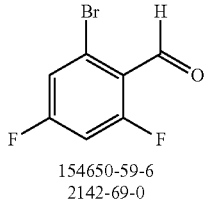 154650-59-6 2142-69-0 | 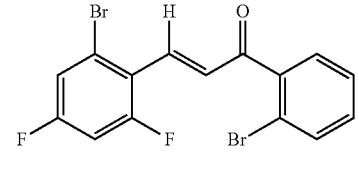 [SMILES: O=C(/C=C/c1c(F)cc(F)cc1Br)c1ccccc1Br] | 86% |
| S24 | 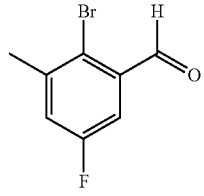 1799977-88-0 2142-69-0 | 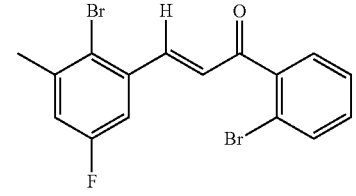 [SMILES: Cc1cc(F)cc(/C=C/C(=O)c2ccccc2Br)c1Br] | 95% |
| S25 | 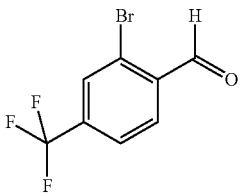 85118-24-7 2142-69-0 | 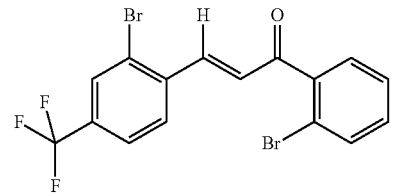 [SMILES: O=C(/C=C/c1ccc(C(F)(F)F)cc1Br)c1ccccc1Br] | 95% |
| S26 | 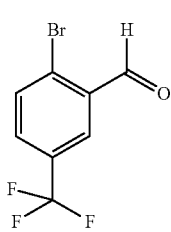 102684-91-3 2142-69-0 | 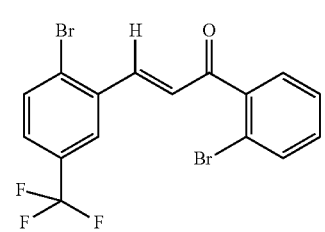 [SMILES: O=C(/C=C/c1cc(C(F)(F)F)ccc1Br)c1ccccc1Br] | 90% |

-continued
| Ex. | Reactants | Product / Solvent added to the reaction | Yield |
|---|---|---|---|
| S27 | 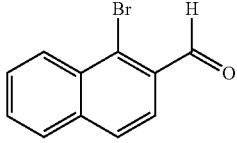<br>3378-82-3<br>2142-69-0 | 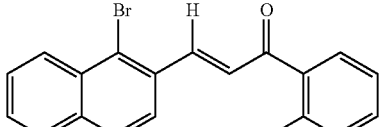<br>Addition of 30 ml of THF | 92% |
| S28 | 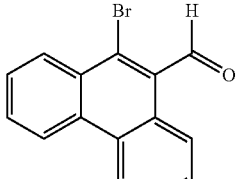<br>52979-72-3<br>2142-69-0 | 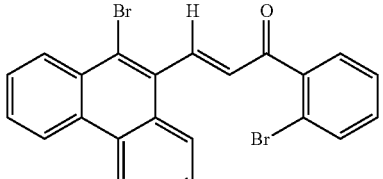<br>Addition of 30 ml of THF | 88% |
| S29 | 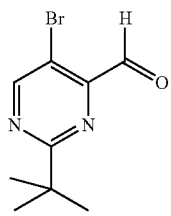<br>1780196-87-3<br>2142-69-0 | 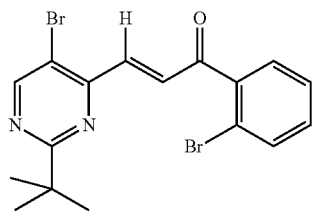 [SMILES: CC(C)(C)c1ncc(Br)c(/C=C/C(=O)c2ccccc2Br)n1] | 98% |
| S30 | 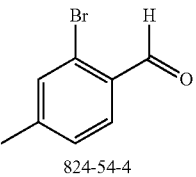<br>824-54-4<br>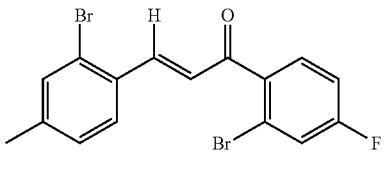 [SMILES: Cc1ccc(/C=C/C(=O)c2ccc(F)cc2Br)c(Br)c1]<br>1006-39-9 | 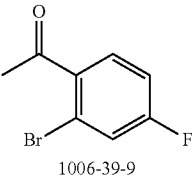 | 96% |
| S31 | 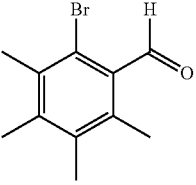<br>88174-34-9<br>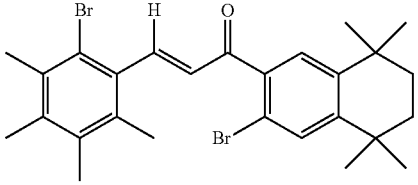<br>27452-18-2 | 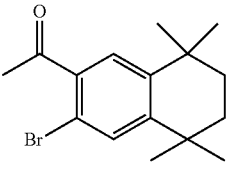<br>Addition of 30 ml of THF | 94% |

| Ex. | Reactants | Product Solvent added to the reaction | Yield |
|---|---|---|---|
| S32 | 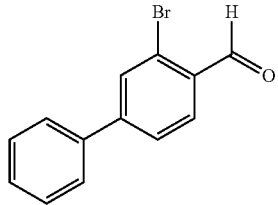<br>1237125-81-3<br>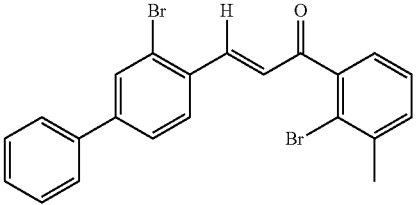 [SMILES: Cc1cccc(C(=O)/C=C/c2ccc(-c3ccccc3)cc2Br)c1Br]<br>944268-58-0 | 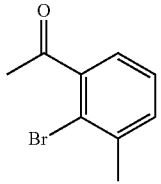 | 90% |
| S33 | 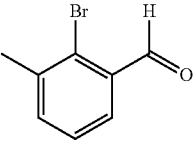<br>109179-31-9<br>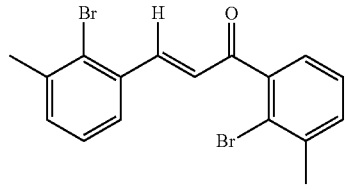 [SMILES: Cc1cccc(/C=C/C(=O)c2cccc(C)c2Br)c1Br]<br>944268-58-0 | 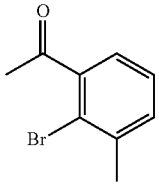 | 95% |
| S34 | 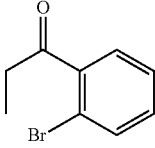<br>62403-86-5<br>6030-33-7 | 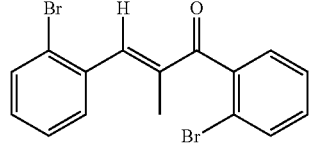 [SMILES: C/C(=C\c1ccccc1Br)C(=O)c1ccccc1Br] | 76% |
| S35 | 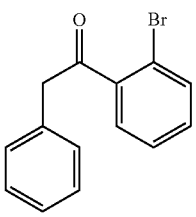<br>36081-66-0<br>6030-33-7 | 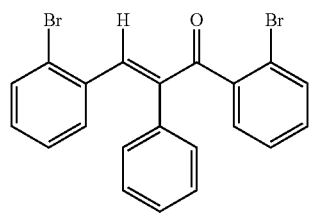 [SMILES: O=C(/C(=C/c1ccccc1Br)c1ccccc1)c1ccccc1Br] | 91% |

| Ex. | Reactants | Product Solvent added to the reaction | Yield |
|---|---|---|---|
| S36 | 1406530-21-9<br>6030-33-7 | Addition of 30 ml of THF | 88% |
| S37 | 1406530-21-9<br>6030-33-7<br><br>88174-34-9 | Addition of 30 ml of THF | 67% |

Step 2

Example S100

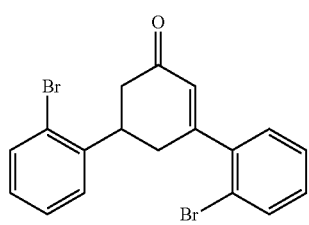 [SMILES: O=C1C=C(c2ccccc2Br)CC(c2ccccc2Br)C1]

To a solution of 36.6 g (100 mmol) of S1 in 100 ml of acetone are added 5.7 g (105 mmol) of sodium methoxide, and the mixture is stirred at 50° C. for 2 h. After the acetone has been removed under reduced pressure, the residue is taken up in 300 ml of ethyl acetate, washed twice with 100 ml each time of water and once with 100 ml of saturated sodium chloride solution, and dried over magnesium sulfate. After the solvent has been removed under reduced pressure, a viscous oil is obtained. Yield: 39.4 g (97 mmol), 97%; purity: about 97% by $^1$H NMR.

In an analogous manner, it is possible to prepare the following compounds:

| Ex. | Reactants | Products | Yield |
|---|---|---|---|
| S101 | S2 | (structure) | 95% |
| S102 | S3 | (structure) | 96% |
| S103 | S4 | (structure) | 90% |
| S104 | S5 | (structure) | 94% |
| S105 | S6 | (structure) | 95% |
| S106 | S7 | (structure) | 95% |
| S107 | S8 | (structure) | 92% |

-continued
| Ex. | Reactants | Products | Yield |
|---|---|---|---|
| S108 | S9 | 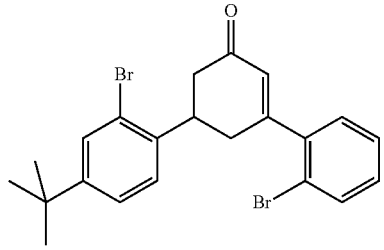 [SMILES: CC(C)(C)c1ccc(C2CC(=O)C=C(c3ccccc3Br)C2)c(Br)c1] | 97% |
| S109 | S10 | 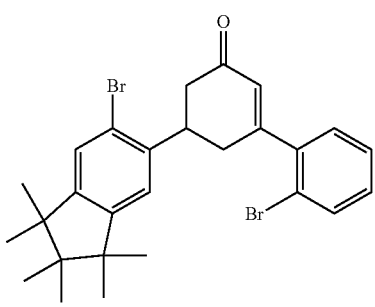 [SMILES: CC1(C)c2cc(Br)c(C3CC(=O)C=C(c4ccccc4Br)C3)cc2C(C)(C)C1(C)C] | 94% |
| S110 | S11 | 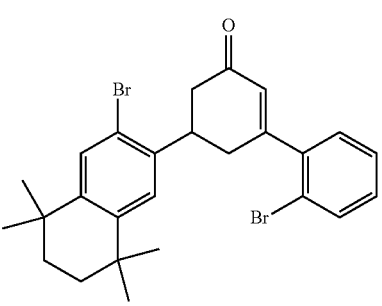 [SMILES: CC1(C)CCC(C)(C)c2cc(C3CC(=O)C=C(c4ccccc4Br)C3)c(Br)cc21] | 95% |
| S111 | S12 | 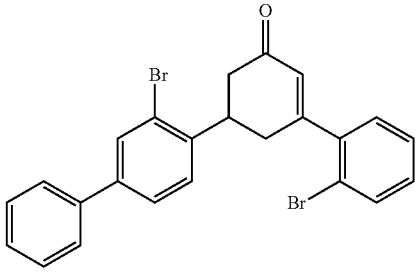 [SMILES: O=C1C=C(c2ccccc2Br)CC(c2ccc(-c3ccccc3)cc2Br)C1] | 95% |
| S112 | S13 | 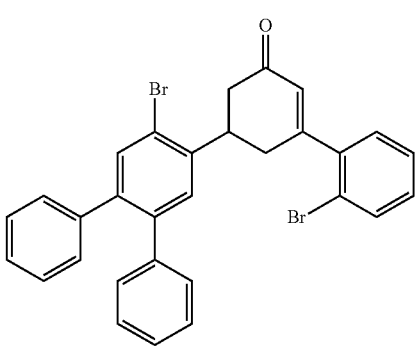 [SMILES: O=C1C=C(c2ccccc2Br)CC(c2cc(-c3ccccc3)c(-c3ccccc3)cc2Br)C1] | 96% |

-continued

| Ex. | Reactants | Products | Yield |
|---|---|---|---|
| S113 | S14 | | 89% |
| S114 | S15 | | 92% |
| S115 | S16 | | 95% |
| S116 | S17 | | 93% |
| S117 | S18 | | 94% |

-continued
| Ex. | Reactants | Products | Yield |
|---|---|---|---|
| S118 | S19 | 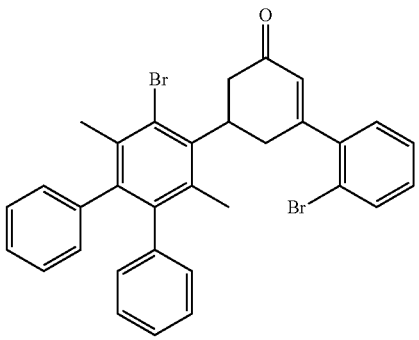 [SMILES: Cc1c(Br)c(C2CC(=O)C=C(c3ccccc3Br)C2)c(C)c(-c2ccccc2)c1-c1ccccc1] | 96% |
| S119 | S20 | 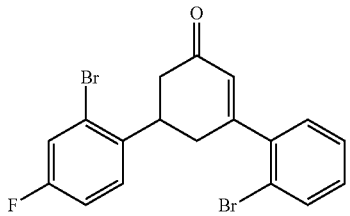 | 95% |
| S120 | S21 | 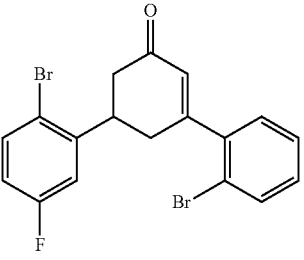 [SMILES: O=C1C=C(c2ccccc2Br)CC(c2cc(F)ccc2Br)C1] | 95% |
| S121 | S22 | 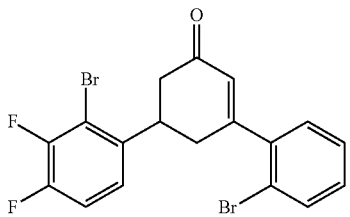 [SMILES: O=C1C=C(c2ccccc2Br)CC(c2ccc(F)c(F)c2Br)C1] | 94% |
| S122 | S23 | 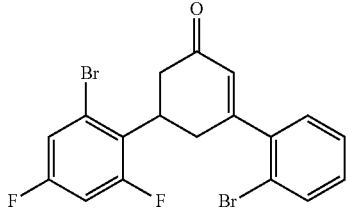 [SMILES: O=C1C=C(c2ccccc2Br)CC(c2c(F)cc(F)cc2Br)C1] | 95% |
| S123 | S24 | 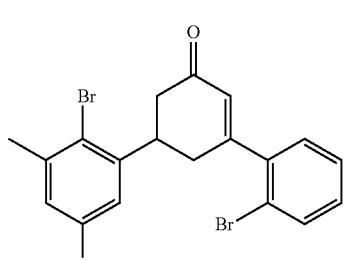 | 96% |

-continued

| Ex. | Reactants | Products | Yield |
|---|---|---|---|
| S124 | S25 | | 93% |
| S125 | S26 | | 96% |
| S126 | S27 | | 89% |
| S127 | S28 | | 84% |
| S128 | S29 | | 90% |
| S129 | S30 | | 95% |

-continued

| Ex. | Reactants | Products | Yield |
|---|---|---|---|
| S130 | S31 | | 97% |
| S131 | S32 | | 95% |
| S132 | S33 | | 93% |
| S133 | S34 | | 89% |
| S134 | S35 | | 77% |

-continued
| Ex. | Reactants | Products | Yield |
|---|---|---|---|
| S135 | S36 | 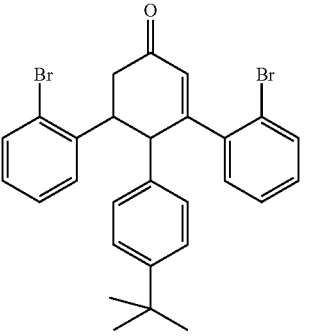 [SMILES: CC(C)(C)c1ccc(C2C(c3ccccc3Br)=CC(=O)CC2c2ccccc2Br)cc1] | 73% |
| S136 | S37 | 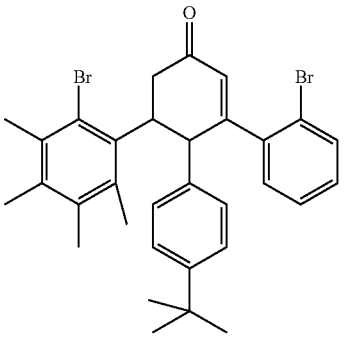 [SMILES: Cc1c(C)c(C)c(C2CC(=O)C=C(c3ccccc3Br)C2c2ccc(C(C)(C)C)cc2)c(Br)c1C] | 67% |
| S137 | S8<br>[ethyl ketone structure]<br>96-22-0<br>as solvent and reagent rather than acetone<br>70° C./8 h | 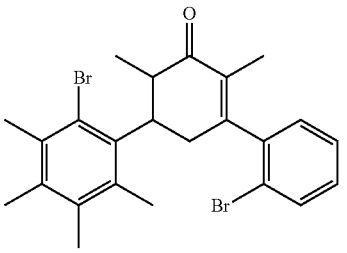 [SMILES: CC1=C(c2ccccc2Br)CC(c2c(C)c(C)c(C)c(C)c2Br)C(C)C1=O] | 73% |
| S138 | S8<br>[dibenzyl ketone structure]<br>102-04-5<br>as solvent and reagent rather than acetone<br>70° C./8 h | 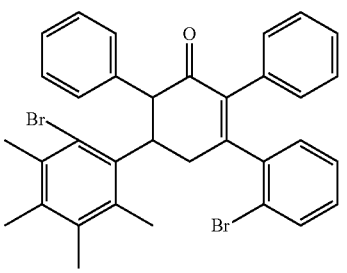 [SMILES: Cc1c(C)c(C)c(C2CC(c3ccccc3Br)=C(c3ccccc3)C(=O)C2c2ccccc2)c(Br)c1C] | 84% |

| Ex. | Reactants | Products | Yield |
|---|---|---|---|
| S139 | S34 1384579-51-4 200 mmol in 100 ml of THF 65° C./16 h | Chromatography on silica gel n-heptane/EA 4:1 vv | 57% |

Step 3

Example S200

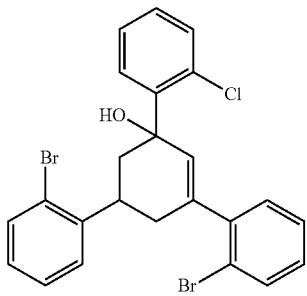 [SMILES: OC1(c2ccccc2Cl)C=C(c2ccccc2Br)CC(c2ccccc2Br)C1]

19.2 g (100 mmol) of 1-bromo-2-chlorobenzene and 2.4 g (100 mmol) of magnesium turnings, with activation of the magnesium turnings with a small grain of iodine, are used to prepare a 1 molar ethereal 2-chlorophenylmagnesium bromide solution. After the Grignard solution has been cooled to 5° C., a solution of 50 mmol of S100 in 150 ml of toluene is added dropwise thereto. The mixture is stirred for a further 3 h and then the reaction mixture is poured onto 500 g of ice. The organic phase is removed, and the aqueous phase is acidified with conc. HCl and extracted once with 100 ml of toluene. The combined organic phases are dried over magnesium sulfate, then the solvent is removed under reduced pressure and the oily residue is digested with n-heptane. The precipitated solids are filtered off with suction, washed with 30 ml of cold n-heptane and dried under reduced pressure. Yield: 14.0 g (27 mmol), 54%; purity: about 90-95% by $^1$H NMR.

In an analogous manner, it is possible to prepare the following compounds:

| Ex. | Reactants | Products | Yield |
|---|---|---|---|
| S201 | S101 |  | 48% |

-continued
| Ex. | Reactants | Products | Yield |
|---|---|---|---|
| S202 | S102 | 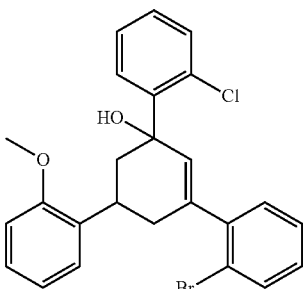 | 63% |
| S203 | S103 | 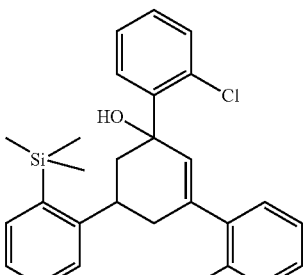 | 67% |
| S204 | S104 | 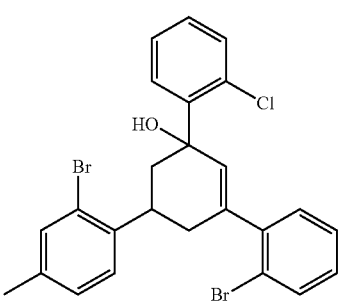 [SMILES: Cc1ccc(C2CC(c3ccccc3Br)=CC(O)(c3ccccc3Cl)C2)c(Br)c1] | 56% |
| S205 | S105 | 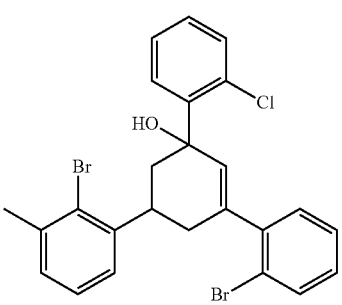 [SMILES: Cc1cccc(C2CC(c3ccccc3Br)=CC(O)(c3ccccc3Cl)C2)c1Br] | 58% |
| S206 | S106 | 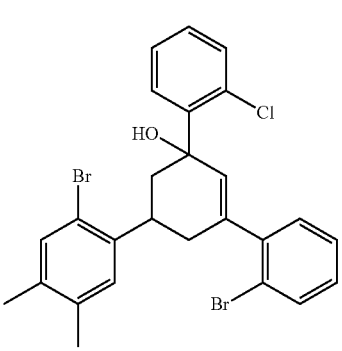 [SMILES: Cc1cc(Br)c(C2CC(c3ccccc3Br)=CC(O)(c3ccccc3Cl)C2)cc1C] | 55% |

-continued
| Ex. | Reactants | Products | Yield |
|---|---|---|---|
| S207 | S107 | 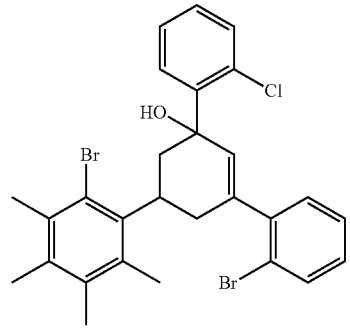 [SMILES: Cc1c(C)c(C)c(C2CC(c3ccccc3Br)=CC(O)(c3ccccc3Cl)C2)c(Br)c1C] | 57% |
| S208 | S108 | 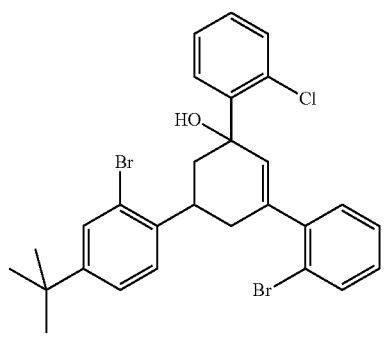 [SMILES: CC(C)(C)c1ccc(C2CC(c3ccccc3Br)=CC(O)(c3ccccc3Cl)C2)c(Br)c1] | 60% |
| S209 | S109 | 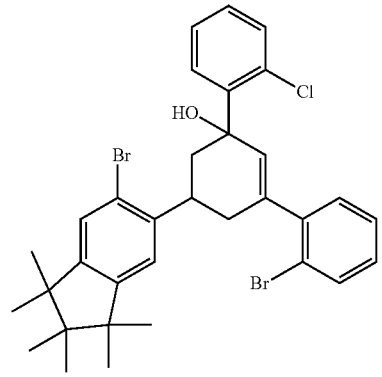 [SMILES: CC1(C)c2cc(Br)c(C3CC(c4ccccc4Br)=CC(O)(c4ccccc4Cl)C3)cc2C(C)(C)C1(C)C] | 63% |
| S210 | S110 | 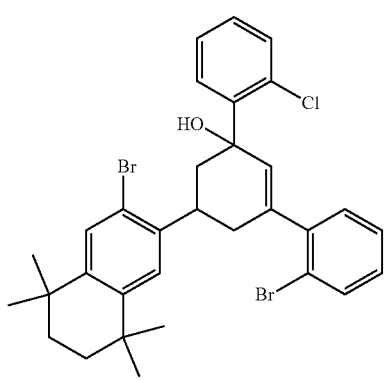 [SMILES: CC1(C)CCC(C)(C)c2cc(C3CC(c4ccccc4Br)=CC(O)(c4ccccc4Cl)C3)c(Br)cc21] | 60% |

-continued
| Ex. | Reactants | Products | Yield |
|---|---|---|---|
| S211 | S111 | 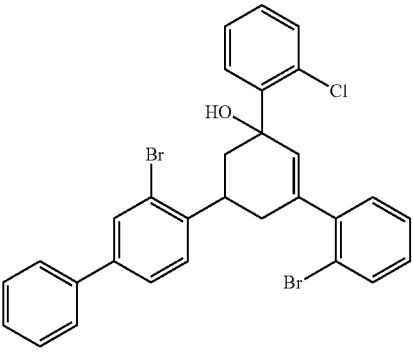 [SMILES: OC1(c2ccccc2Cl)C=C(c2ccccc2Br)CC(c2ccc(-c3ccccc3)cc2Br)C1] | 64% |
| S212 | S112 | 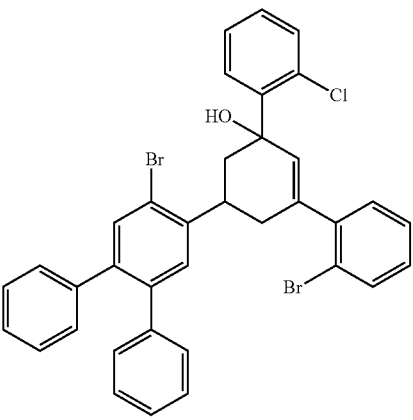 [SMILES: OC1(c2ccccc2Cl)C=C(c2ccccc2Br)CC(c2cc(-c3ccccc3)c(-c3ccccc3)cc2Br)C1] | 62% |
| S213 | S113 | 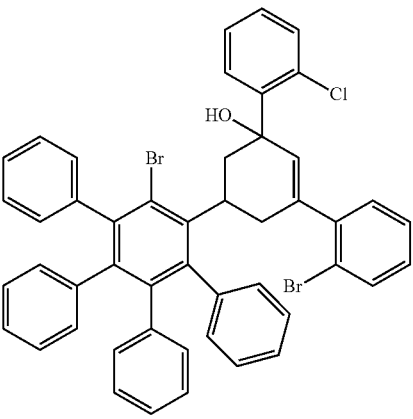 [SMILES: OC1(c2ccccc2Cl)C=C(c2ccccc2Br)CC(c2c(Br)c(-c3ccccc3)c(-c3ccccc3)c(-c3ccccc3)c2-c2ccccc2)C1] | 59% |
| S214 | S114 | 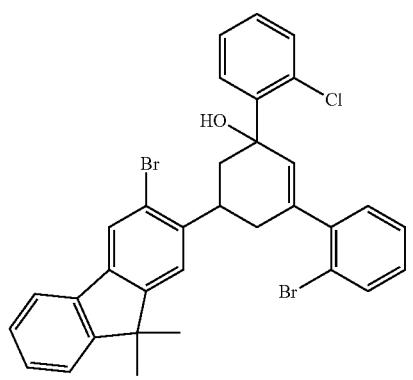 [SMILES: CC1(C)c2ccccc2-c2cc(Br)c(C3CC(c4ccccc4Br)=CC(O)(c4ccccc4Cl)C3)cc21] | 60% |

-continued
| Ex. | Reactants | Products | Yield |
|---|---|---|---|
| S215 | S115 | 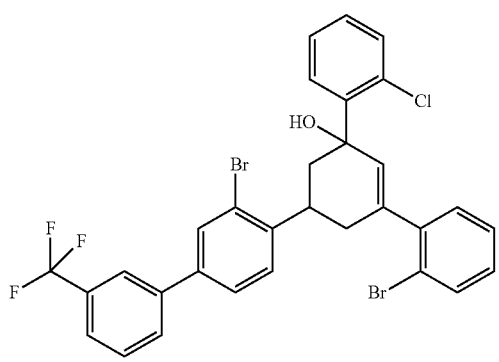 [SMILES: OC1(c2ccccc2Cl)C=C(c2ccccc2Br)CC(c2ccc(-c3cccc(C(F)(F)F)c3)cc2Br)C1] | 58% |
| S216 | S116 | 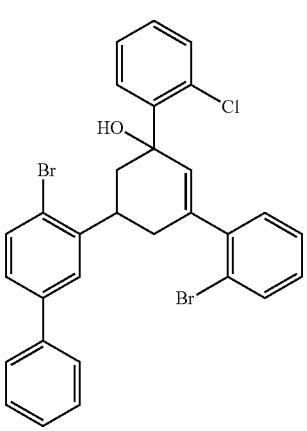 [SMILES: OC1(c2ccccc2Cl)C=C(c2ccccc2Br)CC(c2cc(-c3ccccc3)ccc2Br)C1] | 55% |
| S217 | S117 | 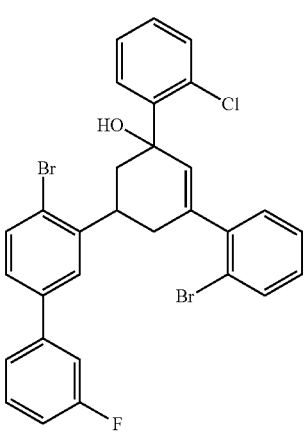 [SMILES: OC1(c2ccccc2Cl)C=C(c2ccccc2Br)CC(c2cc(-c3cccc(F)c3)ccc2Br)C1] | 57% |

-continued

| Ex. | Reactants | Products | Yield |
|---|---|---|---|
| S218 | S118 | | 62% |
| S219 | S119 | | 60% |
| S220 | S120 | | 53% |
| S221 | S121 | | 48% |

| Ex. | Reactants | Products | Yield |
|---|---|---|---|
| S222 | S122 | 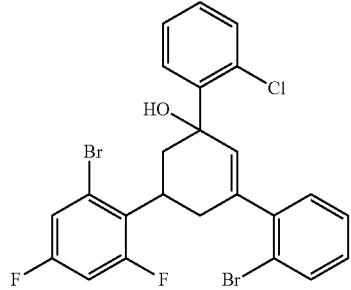 [SMILES: OC1(c2ccccc2Cl)C=C(c2ccccc2Br)CC(c2c(F)cc(F)cc2Br)C1] | 52% |
| S223 | S123 | 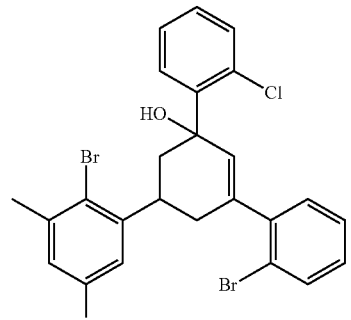 | 55% |
| S224 | S124 | 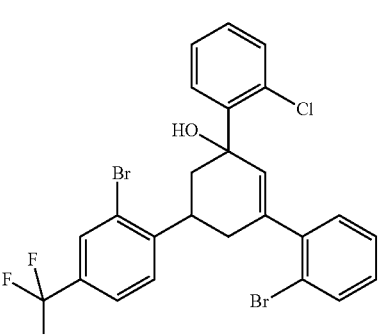 | 57% |
| S225 | S125 | 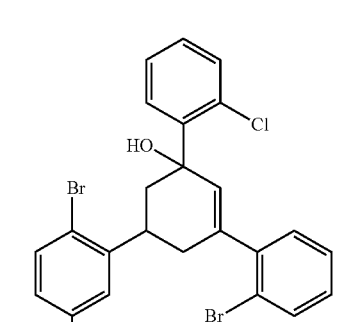 | 56% |

-continued

| Ex. | Reactants | Products | Yield |
|---|---|---|---|
| S226 | S126 | | 60% |
| S227 | S127 | | 60% |
| S228 | S128 | | 39% |
| S229 | S129 | | 56% |

-continued
| Ex. | Reactants | Products | Yield |
|---|---|---|---|
| S230 | S130 | 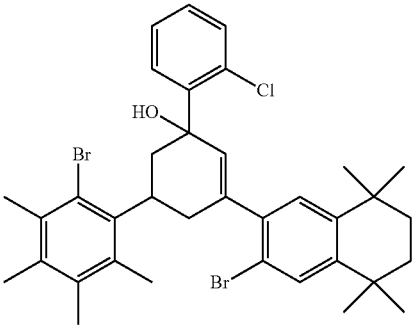 [SMILES: Cc1c(C)c(C)c(C2CC(c3cc4c(cc3Br)C(C)(C)CCC4(C)C)=CC(O)(c3ccccc3Cl)C2)c(Br)c1C] | 58% |
| S231 | S131 | 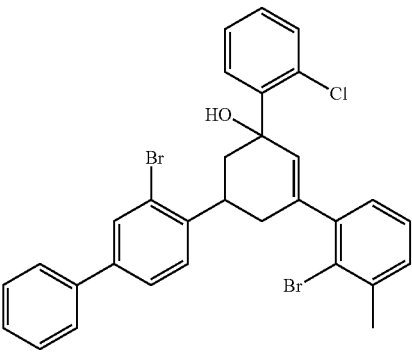 [SMILES: Cc1cccc(C2=CC(O)(c3ccccc3Cl)CC(c3ccc(-c4ccccc4)cc3Br)C2)c1Br] | 60% |
| S232 | S132 | 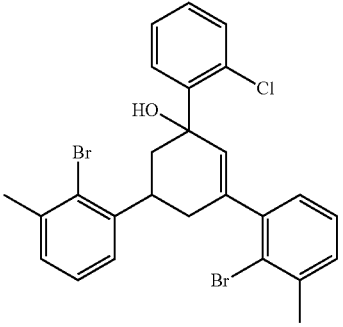 [SMILES: Cc1cccc(C2=CC(O)(c3ccccc3Cl)CC(c3cccc(C)c3Br)C2)c1Br] | 63% |
| S233 | S133 | 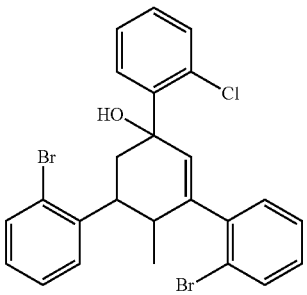 [SMILES: CC1C(c2ccccc2Br)=CC(O)(c2ccccc2Cl)CC1c1ccccc1Br] | 47% |

| Ex. | Reactants | Products | Yield |
|---|---|---|---|
| S234 | S134 | (structure) | 43% |
| S235 | S135 | (structure) | 49% |
| S236 | S136 | (structure) | 50% |
| S237 | S137 | (structure) | 33% |

-continued
| Ex. | Reactants | Products | Yield |
|---|---|---|---|
| S238 | S138 | 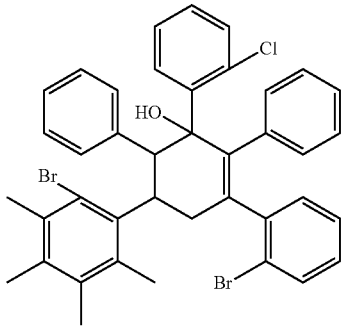 [SMILES: Cc1c(C)c(C)c(C2CC(c3ccccc3Br)=C(c3ccccc3)C(O)(c3ccccc3Cl)C2c2ccccc2)c(Br)c1C] | 28% |
| S239 | S139 | 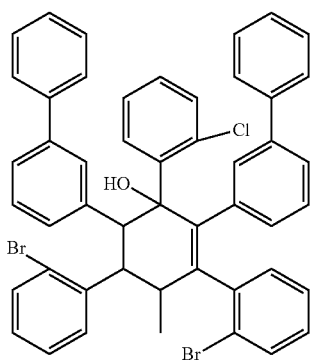 [SMILES: CC1C(c2ccccc2Br)=C(c2cccc(-c3ccccc3)c2)C(O)(c2ccccc2Cl)C(c2cccc(-c3ccccc3)c2)C1c1ccccc1Br] | 19% |
| S240 | S107<br>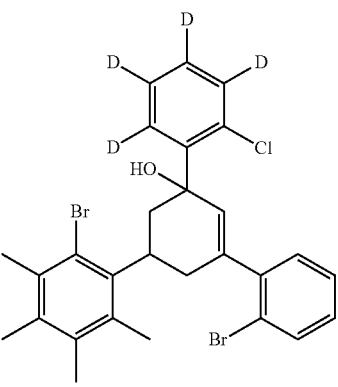<br>1219795-51-3 | | 63% |
| S241 | S107<br>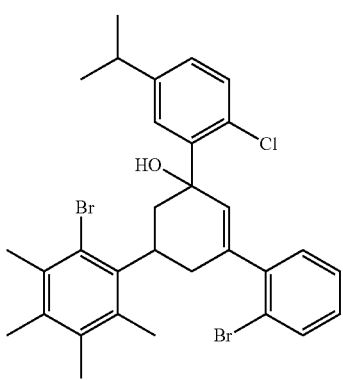<br>90350-25-7 | | 60% |

-continued

| Ex. | Reactants | Products | Yield |
|---|---|---|---|
| S242 | S132<br>1890709-49-5 | | 59% |
| S243 | S130<br>1890709-49-5 | | 54% |

Step 4

Example P1

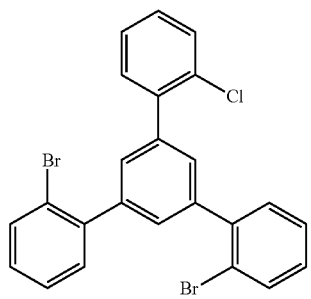

A solution of 10.4 g (20 mmol) of S200 and 500 mg of p-toluenesulfonic acid in 200 ml of chlorobenzene is heated on a water separator for 2 h, removing the water formed. The reaction mixture is cooled down to room temperature, 8.7 g (100 mmol) of manganese(IV) oxide and 100 g of glass beads (diameter 3 mm) are added, and the mixture is heated again on a water separator with good stirring for 4 h. After being cooled down to about 60° C., the reaction mixture is filtered through Celite, the Celite is washed through with 100 ml of chlorobenzene, and the filtrate is concentrated to dryness under reduced pressure. The residue is chromatographed on silica gel (n-heptane:EA, 9:1 vv) and finally recrystallized from methanol. Yield: 7.0 g (14 mmol), 70%; purity: 99% by $^1$H NMR.

Rather than manganese(IV) oxide, it is also possible to use 25 mmol of DDQ (variant B).

In an analogous manner, it is possible to prepare the following compounds:

| Ex. | Reactants | Products | Yield |
|---|---|---|---|
| P2 | S201 | | 66% |

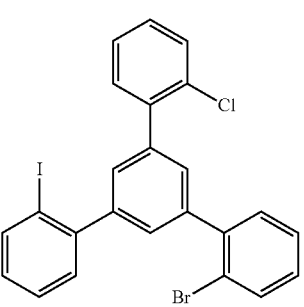 [SMILES: Clc1ccccc1-c1cc(-c2ccccc2Br)cc(-c2ccccc2I)c1]

-continued

| Ex. | Reactants | Products | Yield |
|---|---|---|---|
| P3 | S202 | | 73% |
| P4 | S203 | | 65% |
| P5 | S204 Variant B | | 70% |
| P6 | S205 Variant B | | 72% |
| P7 | S206 Variant B | | 68% |

-continued
| Ex. | Reactants | Products | Yield |
|---|---|---|---|
| P8 | S207 Variant B | 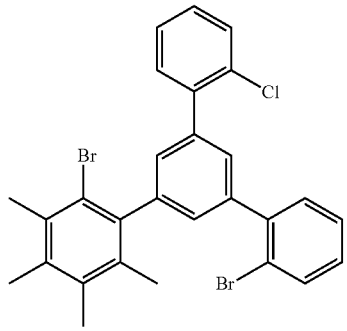 [SMILES: Cc1c(C)c(C)c(-c2cc(-c3ccccc3Cl)cc(-c3ccccc3Br)c2)c(Br)c1C] | 70% |
| P9 | S208 | 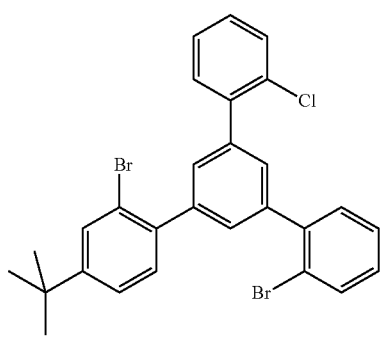 [SMILES: CC(C)(C)c1ccc(-c2cc(-c3ccccc3Cl)cc(-c3ccccc3Br)c2)c(Br)c1] | 69% |
| P10 | S209 | 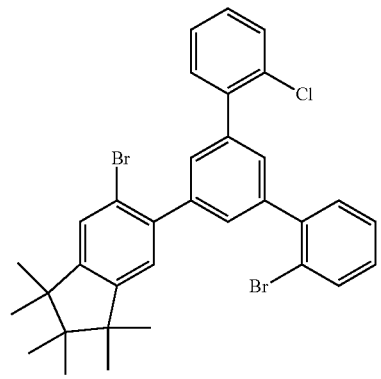 [SMILES: CC1(C)c2cc(Br)c(-c3cc(-c4ccccc4Cl)cc(-c4ccccc4Br)c3)cc2C(C)(C)C1(C)C] | 73% |
| P11 | S210 | 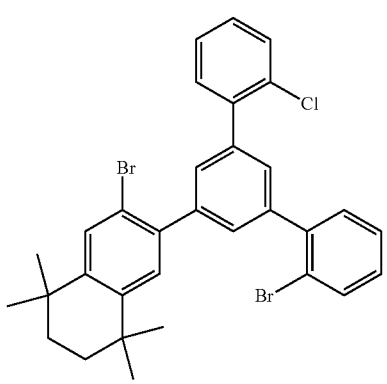 [SMILES: CC1(C)CCC(C)(C)c2cc(-c3cc(-c4ccccc4Cl)cc(-c4ccccc4Br)c3)c(Br)cc21] | 72% |

-continued

| Ex. | Reactants | Products | Yield |
|---|---|---|---|
| P12 | S211 | | 67% |
| P13 | S212 | | 69% |
| P14 | S213 | | 58% |
| P15 | S214 | | 71% |

-continued

| Ex. | Reactants | Products | Yield |
|---|---|---|---|
| P16 | S215 | | 66% |
| P17 | S216 | | 68% |
| P18 | S217 | | 63% |
| P19 | S218 Variant B | | 65% |

-continued
| Ex. | Reactants | Products | Yield |
|---|---|---|---|
| P20 | S219 | 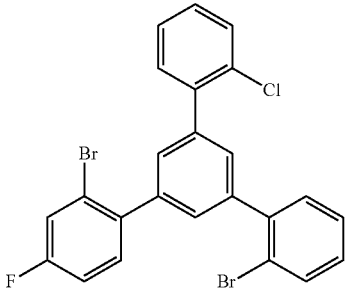 [SMILES: Fc1ccc(-c2cc(-c3ccccc3Cl)cc(-c3ccccc3Br)c2)c(Br)c1] | 74% |
| P21 | S220 | 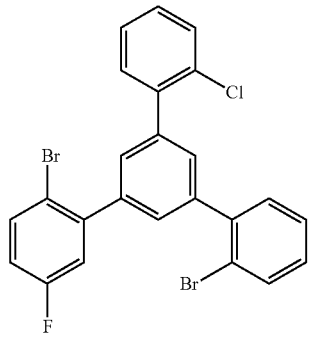 [SMILES: Fc1ccc(Br)c(-c2cc(-c3ccccc3Cl)cc(-c3ccccc3Br)c2)c1] | 75% |
| P22 | S221 | 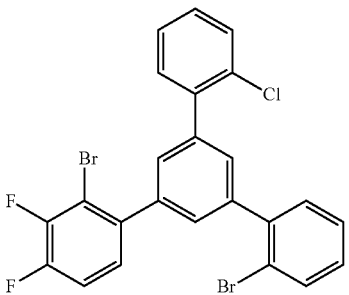 [SMILES: Fc1ccc(-c2cc(-c3ccccc3Cl)cc(-c3ccccc3Br)c2)c(Br)c1F] | 72% |
| P23 | S222 | 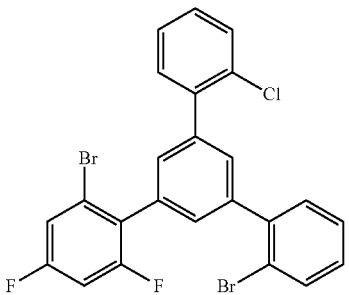 [SMILES: Fc1cc(F)c(-c2cc(-c3ccccc3Cl)cc(-c3ccccc3Br)c2)c(Br)c1] | 70% |
| P24 | S223 Variant B | 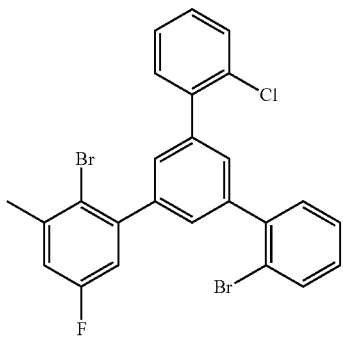 [SMILES: Cc1cc(F)cc(-c2cc(-c3ccccc3Cl)cc(-c3ccccc3Br)c2)c1Br] | 68% |

| Ex. | Reactants | Products | Yield |
|---|---|---|---|
| P25 | S224 | 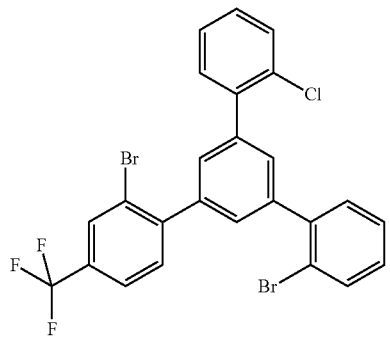 [SMILES: FC(F)(F)c1ccc(-c2cc(-c3ccccc3Cl)cc(-c3ccccc3Br)c2)c(Br)c1] | 63% |
| P26 | S225 | 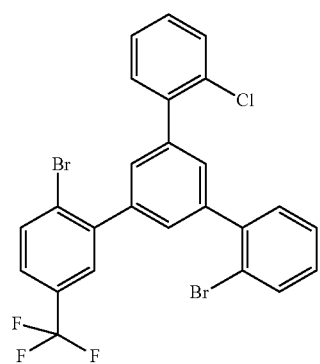 [SMILES: FC(F)(F)c1ccc(Br)c(-c2cc(-c3ccccc3Cl)cc(-c3ccccc3Br)c2)c1] | 58% |
| P27 | S226 | 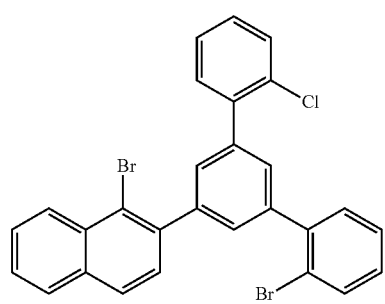 [SMILES: Clc1ccccc1-c1cc(-c2ccccc2Br)cc(-c2ccc3ccccc3c2Br)c1] | 65% |
| P28 | S227 | 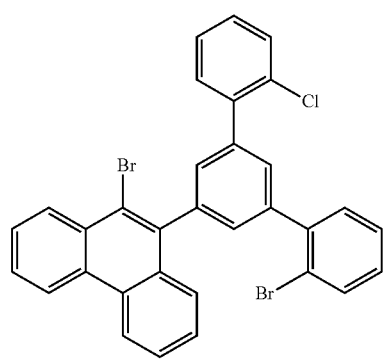 [SMILES: Clc1ccccc1-c1cc(-c2ccccc2Br)cc(-c2c(Br)c3ccccc3c3ccccc23)c1] | 67% |

| Ex. | Reactants | Products | Yield |
|---|---|---|---|
| P29 | S228 | 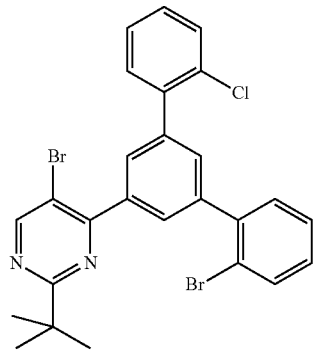 [SMILES: CC(C)(C)c1ncc(Br)c(-c2cc(-c3ccccc3Cl)cc(-c3ccccc3Br)c2)n1] | 54% |
| P30 | S229 Variant B | 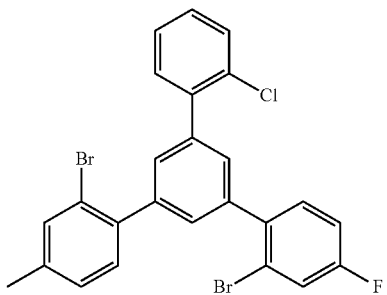 [SMILES: Cc1ccc(-c2cc(-c3ccccc3Cl)cc(-c3ccc(F)cc3Br)c2)c(Br)c1] | 70% |
| P31 | S230 Variant B | 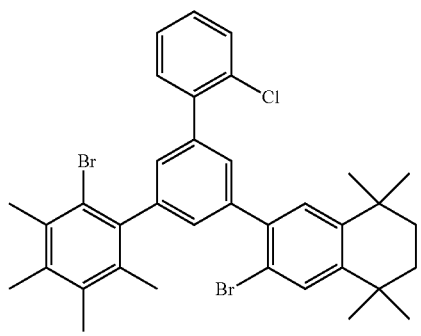 [SMILES: Cc1c(C)c(C)c(-c2cc(-c3ccccc3Cl)cc(-c3cc4c(cc3Br)C(C)(C)CCC4(C)C)c2)c(Br)c1C] | 66% |
| P32 | S231 Variant B | 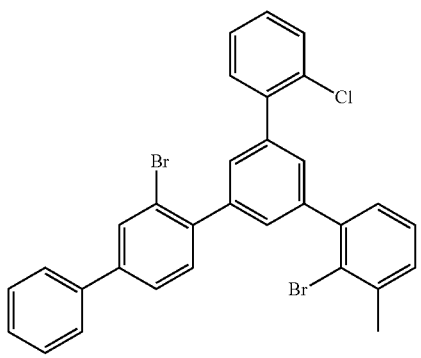 [SMILES: Cc1cccc(-c2cc(-c3ccccc3Cl)cc(-c3ccc(-c4ccccc4)cc3Br)c2)c1Br] | 63% |

-continued

| Ex. | Reactants | Products | Yield |
|---|---|---|---|
| P33 | S232 Variant B | | 69% |
| P34 | S233 Variant B | | 65% |
| P35 | S234 | | 64% |
| P36 | S235 | | 65% |

-continued

| Ex. | Reactants | Products | Yield |
|---|---|---|---|
| P37 | S236 Variant B | | 63% |
| P38 | S237 Variant B | | 68% |
| P39 | S238 Variant B | | 69% |
| P40 | S239 Variant B | | 67% |

-continued
| Ex. | Reactants | Products | Yield |
|---|---|---|---|
| P41 | S240 Variant B | 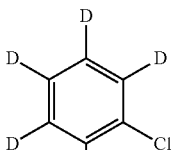 | 65% |
| P42 | S241 Variant B | 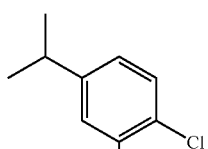 | 69% |
| P43 | S242 Variant B | 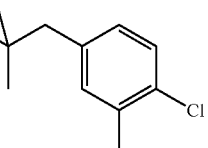 | 65% |
| P44 | S243 Variant B | 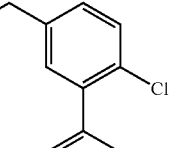 | 68% |

Synthesis of the Ligands

Example Ligand L1

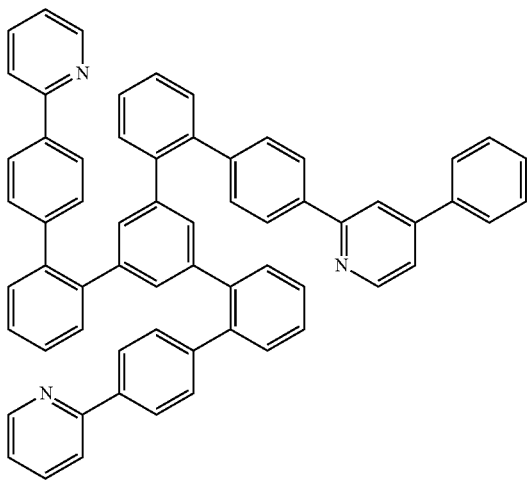 [SMILES: c1ccc(-c2ccnc(-c3ccc(-c4ccccc4-c4cc(-c5ccccc5-c5ccc(-c6ccccn6)cc5)cc(-c5ccccc5-c5ccc(-c6ccccn6)cc5)c4)cc3)c2)cc1]

Step 1, L1 Intermediate

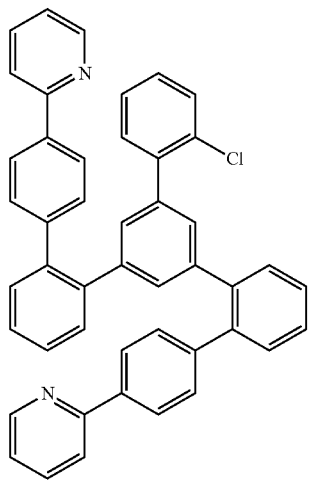 [SMILES: Clc1ccccc1-c1cc(-c2ccccc2-c2ccc(-c3ccccn3)cc2)cc(-c2ccccc2-c2ccc(-c3ccccn3)cc2)c1]

A mixture of 5.0 g (10 mmol) of P1, 5.9 g (21 mmol) of 2-[4-(4,4,5,5-tetramethyl-1,3,2-dioxaborolan-2-yl)phenyl]pyridine [908350-80-1], 6.4 g (60 mmol) of sodium carbonate, 347 mg (0.3 mmol) of tetrakis(triphenylphosphino)palladium(0), 60 ml of toluene, 15 ml of ethanol and 30 ml of water is heated under reflux with good stirring for 18 h. After cooling, the organic phase is extended with 100 ml of ethyl acetate, removed, washed three times with 50 ml each time of water and once with 100 ml of saturated sodium chloride solution, and dried over magnesium sulfate. The mixture is filtered through a silica gel bed in the form of an ethyl acetate slurry, which is washed through with a little ethyl acetate, the solvent is removed under reduced pressure and the oily residue is recrystallized twice from about 30 ml of acetonitrile with addition of a little ethyl acetate. Yield: 5.2 g (8 mmol), 80%. Purity: about 98% by $^1$H NMR.

Step 2, Ligand L1

A mixture of 5.2 g (8 mmol) of L1 intermediate, 2.5 g (9 mmol) of [4-(4-phenyl-2-pyridinyl)phenyl]boronic acid [1714084-80-6], 4.3 g (20 mmol) of tripotassium phosphate, 82 mg (0.2 mmol) of SPhos [657408-07-6], 34 mg (0.15 mmol) of palladium(II) acetate, 50 ml of toluene, 10 ml of dioxane and 40 ml of water is heated under reflux with good stirring for 18 h. After cooling, the organic phase is extended with 100 ml of ethyl acetate, removed, washed three times with 50 ml each time of water and once with 100 ml of saturated sodium chloride solution, and dried over magnesium sulfate. The mixture is filtered through a silica gel bed in the form of an ethyl acetate slurry, which is washed through with a little ethyl acetate, the solvent is removed under reduced pressure and the oily residue is recrystallized twice from about 30 ml of acetonitrile with addition of a little ethyl acetate. Yield: 5.1 g (6 mmol), 75%. Purity: about 98% by $^1$H NMR.

In an analogous manner, the unit shown can be used to prepare the ligands which follow in comparable yields. The intermediates and end products can also be purified by chromatography—preferably using an automatic column system, for example from A. Semrau—or by fractional sublimation:

| Ex. | Triaryl-benzene | Boronic acid/ester 1 Step 1 | Boronic acid/ester 2 Step 2 | Product |
|---|---|---|---|---|
| L2 | P1 | ![structure with pyridine-phenyl-Bpin, 908350-80-1] | ![structure with tert-butyl pyridine-phenyl-Bpin, 1989596-74-8] | ![L2 product structure] |

-continued
| Ex. | Triaryl-benzene | Boronic acid/ester 1 Step 1 | Boronic acid/ester 2 Step 2 | Product |
|---|---|---|---|---|
| L3 | P8 | 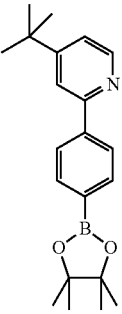<br>1989596-74-8 | 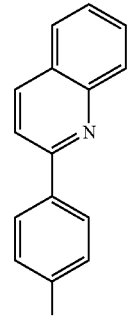<br>1383803-71-1 | 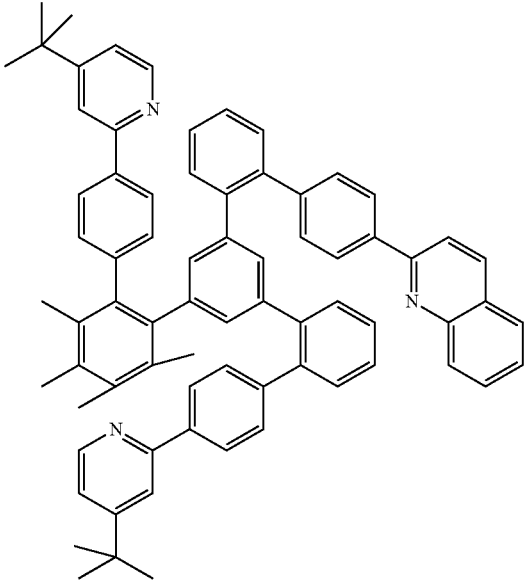 [SMILES: Cc1c(C)c(C)c(-c2cc(-c3ccccc3-c3ccc(-c4cc(C(C)(C)C)ccn4)cc3)cc(-c3ccccc3-c3ccc(-c4ccc5ccccc5n4)cc3)c2)c(-c2ccc(-c3cc(C(C)(C)C)ccn3)cc2)c1C] |
| L4 | P15 | 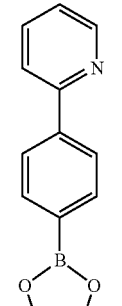<br>908350-80-1 | 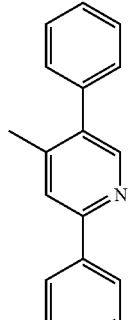<br>1989597-15-0 | 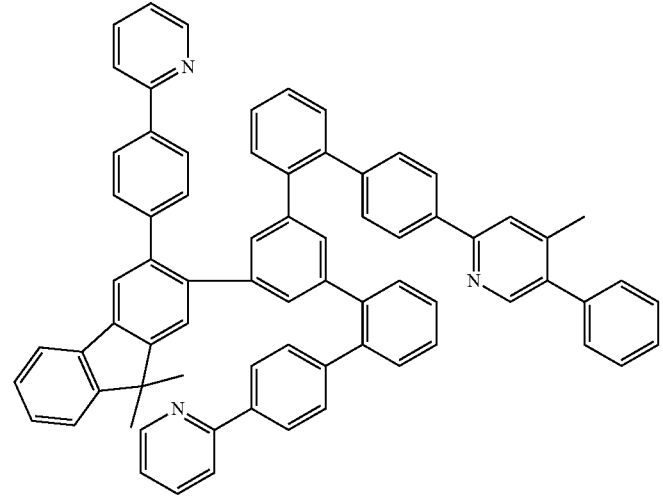 [SMILES: Cc1cc(-c2ccc(-c3ccccc3-c3cc(-c4ccccc4-c4ccc(-c5ccccn5)cc4)cc(-c4cc5c(cc4-c4ccc(-c6ccccn6)cc4)-c4ccccc4C5(C)C)c3)cc2)ncc1-c1ccccc1] |

-continued
| Ex. | Triaryl-benzene | Boronic acid/ester 1 Step 1 | Boronic acid/ester 2 Step 2 | Product |
|---|---|---|---|---|
| L5 | P35 | 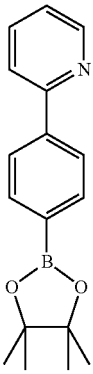 908350-80-1 | 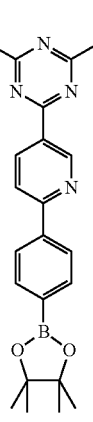 1989603-25-9 | 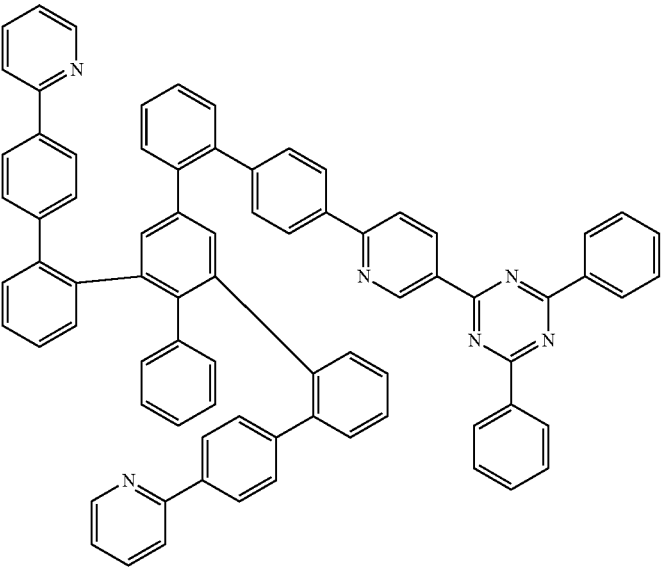 [SMILES: c1ccc(-c2nc(-c3ccccc3)nc(-c3ccc(-c4ccc(-c5ccccc5-c5cc(-c6ccccc6-c6ccc(-c7ccccn7)cc6)c(-c6ccccc6)c(-c6ccccc6-c6ccc(-c7ccccn7)cc6)c5)cc4)nc3)n2)cc1] |
| L6 | P1 | 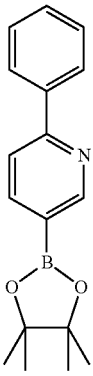 879291-27-7 | 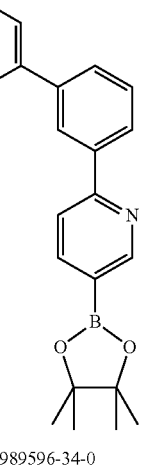 1989596-34-0 | 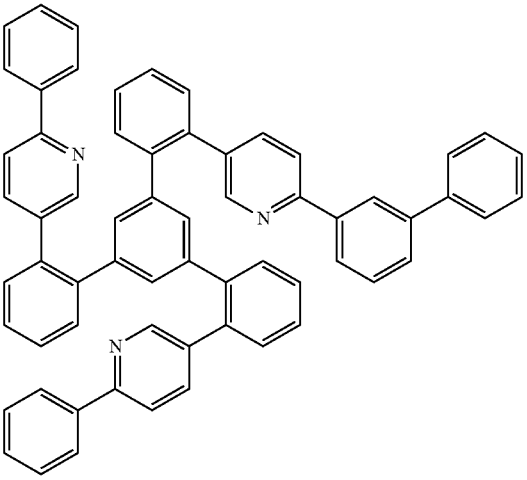 [SMILES: c1ccc(-c2cccc(-c3ccc(-c4ccccc4-c4cc(-c5ccccc5-c5ccc(-c6ccccc6)nc5)cc(-c5ccccc5-c5ccc(-c6ccccc6)nc5)c4)cn3)c2)cc1] |
| L7 | P1 | 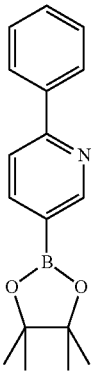 879291-27-7 | 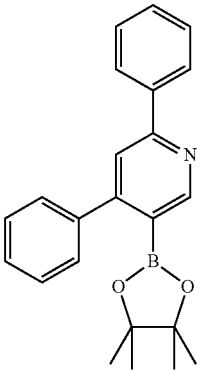 1989596-34-0 | 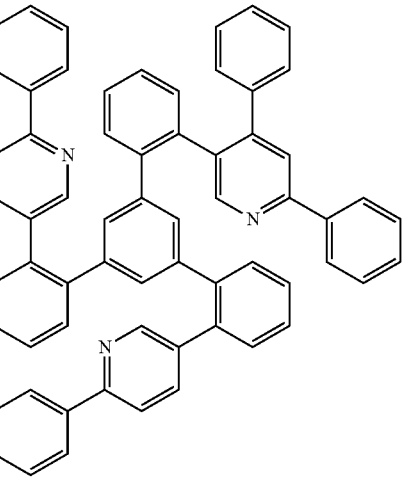 |

| Ex. | Triaryl-benzene | Boronic acid/ester 1 Step 1 | Boronic acid/ester 2 Step 2 | Product |
|---|---|---|---|---|
| L8 | P1 | 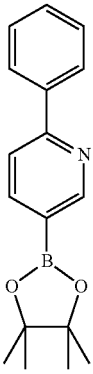<br>879291-27-7 | 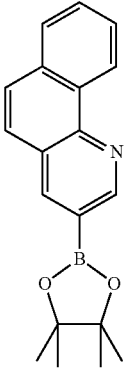<br>189596-48-6 | 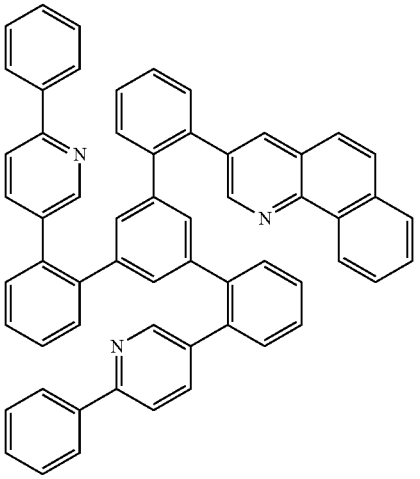 [SMILES: c1ccc(-c2ccc(-c3ccccc3-c3cc(-c4ccccc4-c4ccc(-c5ccccc5)nc4)cc(-c4ccccc4-c4cnc5c(ccc6ccccc65)c4)c3)cn2)cc1] |
| L9 | P1 | 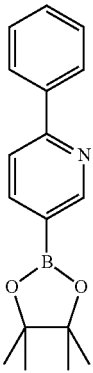<br>879291-27-7 | 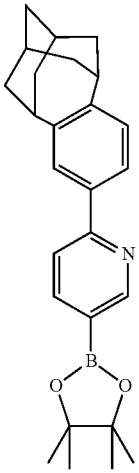<br>1989596-42-0 | 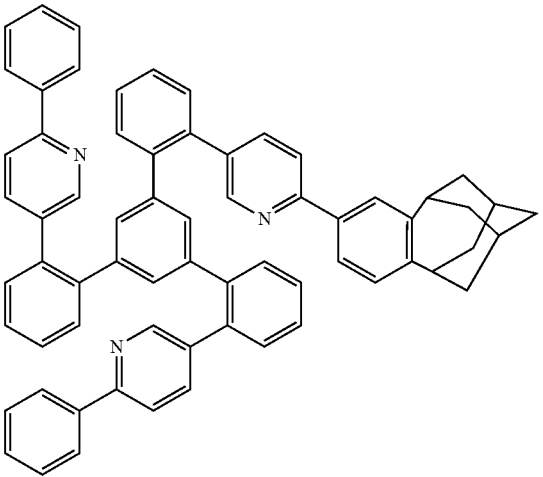 [SMILES: CC1CC2CCCC(C2)c2ccc(-c3ccc(-c4ccccc4-c4cc(-c5ccccc5-c5ccc(-c6ccccc6)nc5)cc(-c5ccccc5-c5ccc(-c6ccccc6)nc5)c4)cn3)cc21] |
| L10 | P1 | 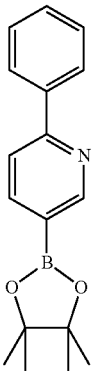<br>879291-27-7 | 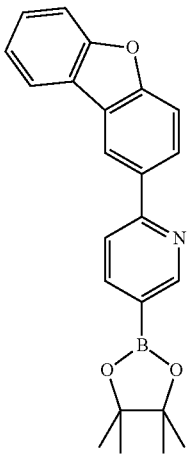<br>1989596-37-3 | 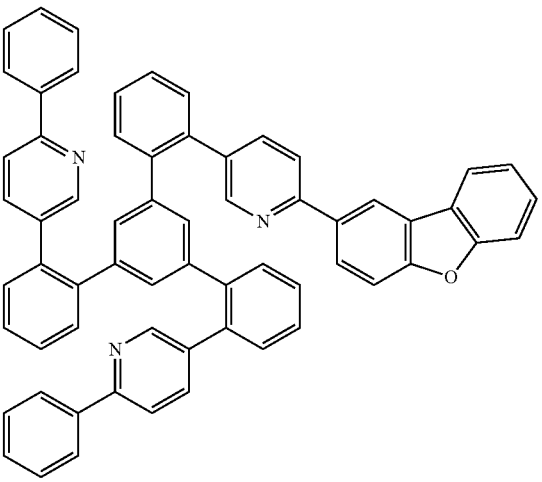 [SMILES: c1ccc(-c2ccc(-c3ccccc3-c3cc(-c4ccccc4-c4ccc(-c5ccccc5)nc4)cc(-c4ccccc4-c4ccc(-c5ccc6oc7ccccc7c6c5)nc4)c3)cn2)cc1] |

-continued

| Ex. | Triarylbenzene | Boronic acid/ester 1 Step 1 | Boronic acid/ester 2 Step 2 | Product |
|---|---|---|---|---|
| L11 | P1 | 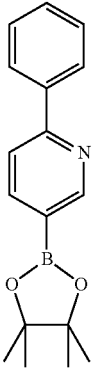 879291-27-7 | 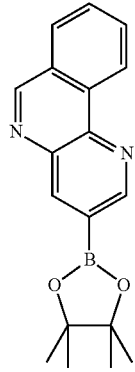 1989596-70-4 | 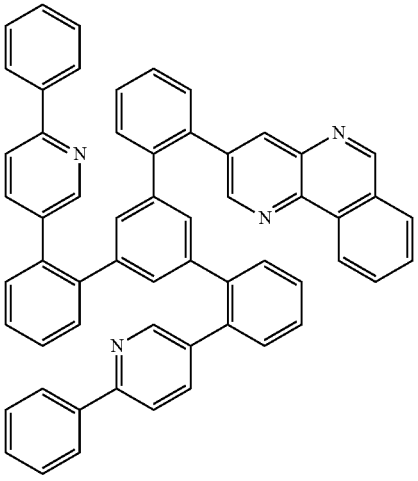 |

Example Ligand L100

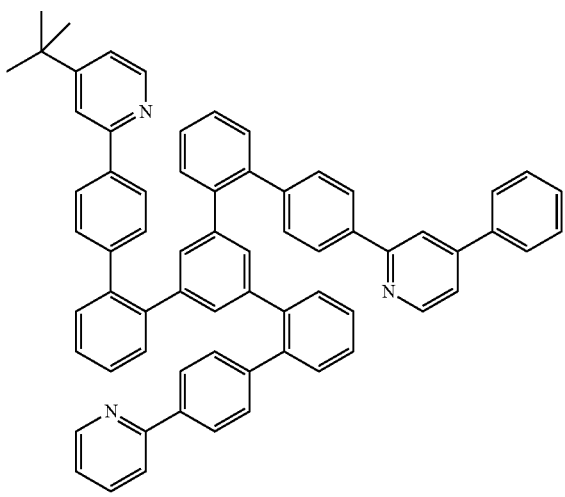 [SMILES: CC(C)(C)c1ccnc(-c2ccc(-c3ccccc3-c3cc(-c4ccccc4-c4ccc(-c5ccccn5)cc4)cc(-c4ccccc4-c4ccc(-c5cc(-c6ccccc6)ccn5)cc4)c3)cc2)c1]

Step 1, L100 Intermediate 1

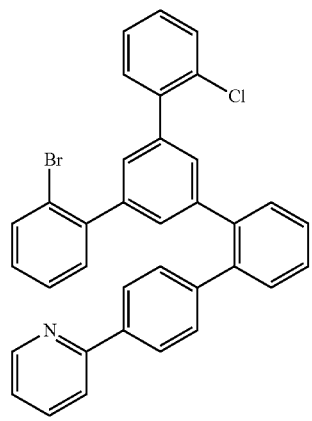 [SMILES: Clc1ccccc1-c1cc(-c2ccccc2Br)cc(-c2ccccc2-c2ccc(-c3ccccn3)cc2)c1]

A mixture of 5.5 g (10 mmol) of P2, 3.1 g (10 mmol) of 2-[4-(4,4,5,5-tetramethyl-1,3,2-dioxaborolan-2-yl)phenyl] pyridine [908350-80-1], 3.2 g (10 mmol) of tetra-n-butylammonium bromide, 2.8 g (20 mmol) of potassium carbonate, 231 mg (0.2 mmol) of tetrakis(triphenylphosphino) palladium(0), 30 ml of toluene and 30 ml of water is heated under reflux with good stirring for 18 h. After cooling, the organic phase is extended with 100 ml of ethyl acetate, removed, washed three times with 50 ml each time of water and once with 100 ml of saturated sodium chloride solution, and dried over magnesium sulfate. The mixture is filtered through a silica gel bed in the form of an ethyl acetate slurry, which is washed through with a little ethyl acetate, the solvent is removed under reduced pressure and the oily residue is recrystallized twice from about 30 ml of acetonitrile with addition of a little ethyl acetate. Yield: 5.2 g (8 mmol), 80%. Purity: about 98% by $^1$H NMR.

Step 2, L100 Intermediate 2

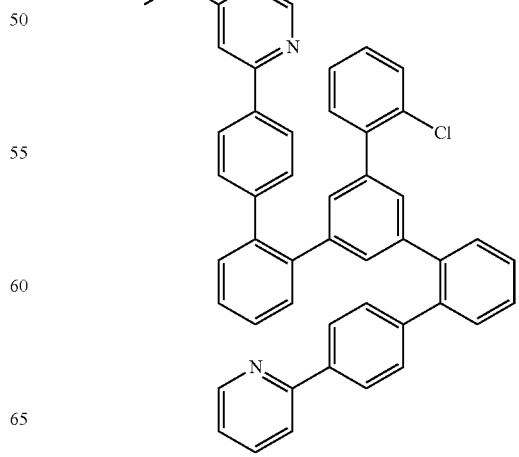

A mixture of 5.2 g (8 mmol) of L100 intermediate 1, 2.7 g (8 mmol) of 4-tert-butyl-2-[4-(4,4,5,5-tetramethyl-1,3,2-dioxaborolan-2-yl)phenyl]pyridine [1989596-74-8], 3.2 g (30 mmol) of sodium carbonate, 173 mg (0.15 mmol) of tetrakis(triphenylphosphino)palladium(0), 60 ml of toluene, 15 ml of ethanol and 30 ml of water is heated under reflux with good stirring for 18 h. After cooling, the organic phase is extended with 100 ml of ethyl acetate, removed, washed three times with 50 ml each time of water and once with 100 ml of saturated sodium chloride solution, and dried over magnesium sulfate. The mixture is filtered through a silica gel bed in the form of an ethyl acetate slurry, which is washed through with a little ethyl acetate, the solvent is removed under reduced pressure and the oily residue is recrystallized twice from about 20 ml of acetonitrile with addition of a little ethyl acetate. Yield: 4.2 g (6 mmol), 75%. Purity: about 98% by $^1$H NMR.

Step 3, Ligand L100

A mixture of 4.2 g (6 mmol) of L100 intermediate 2, 2.0 g (7 mmol) of [4-(4-phenyl-2-pyridinyl)phenyl]boronic acid [1714084-80-6], 3.2 g (15 mmol) of tripotassium phosphate, 82 mg (0.2 mmol) of SPhos [657408-07-6], 34 mg (0.15 mmol) of palladium(II) acetate, 50 ml of toluene, 10 ml of dioxane and 40 ml of water is heated under reflux with good stirring for 18 h. After cooling, the organic phase is extended with 100 ml of ethyl acetate, removed, washed three times with 50 ml each time of water and once with 100 ml of saturated sodium chloride solution, and dried over magnesium sulfate. The mixture is filtered through a silica gel bed in the form of an ethyl acetate slurry, which is washed through with a little ethyl acetate, the solvent is removed under reduced pressure and the oily residue is recrystallized twice from about 25 ml of acetonitrile with addition of a little ethyl acetate. Yield: 4.5 g (5 mmol), 85%. Purity: about 98% by $^1$H NMR.

In an analogous manner, P2 and the units shown can be used to prepare the ligands which follow in comparable yields. The intermediates and end products can also be purified by chromatography—preferably using an automatic column system, for example from A. Semrau—or by fractional sublimation:

| Ex. | Boronic acid/ester 1 Step 1 | Boronic acid/ester 2 Step 2 | Boronic acid/ester 3 Step 3 | Product |
|---|---|---|---|---|
| L101 | 1888454-64-5 | 1989596-74-8 | 1714084-80-6 | |
| L102 | 1103778-52-4 | 1989596-74-8 | 1714084-80-6 | |

-continued

| Ex. | Boronic acid/ester 1 Step 1 | Boronic acid/ester 2 Step 2 | Boronic acid/ester 3 Step 3 | Product |
|---|---|---|---|---|
| L103 | 1116082-29-1 | 1989596-74-8 | 1714084-80-6 | |
| L104 | 1116082-29-1 | 1989596-74-8 | 1365090-47-6 | |
| L105 | 908350-80-1 | 1989596-74-8 | 1989603-32-8 | |

-continued
| Ex. | Boronic acid/ester 1 Step 1 | Boronic acid/ester 2 Step 2 | Boronic acid/ester 3 Step 3 | Product |
|---|---|---|---|---|
| L106 | 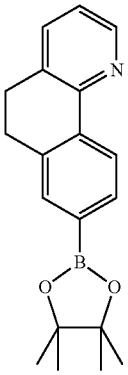 1989597-10-5 | 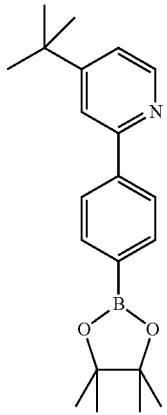 1989596-74-8 | 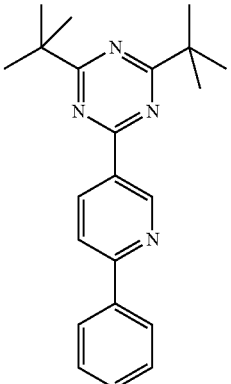 1989603-32-8 | 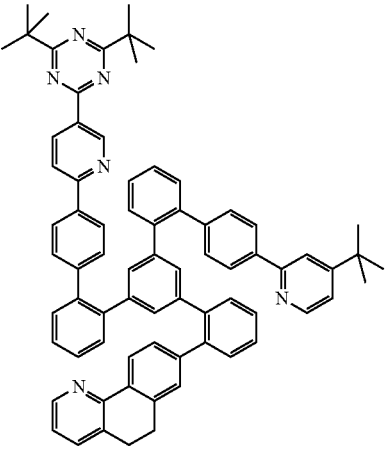 [SMILES: CC(C)(C)c1ccnc(-c2ccc(-c3ccccc3-c3cc(-c4ccccc4-c4ccc(-c5ccc(-c6nc(C(C)(C)C)nc(C(C)(C)C)n6)cn5)cc4)cc(-c4ccccc4-c4ccc5c(c4)CCc4cccnc4-5)c3)cc2)c1] |
| L107 | 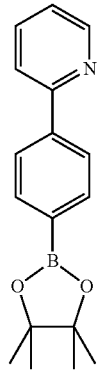 908350-80-1 | 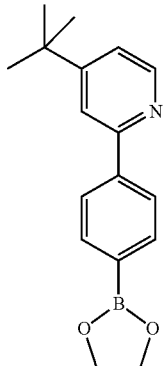 1989596-74-8 | 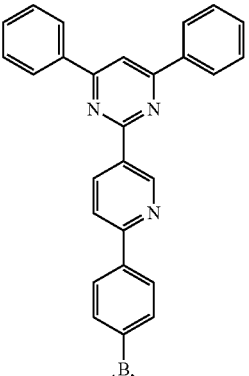 1989603-54-4 | 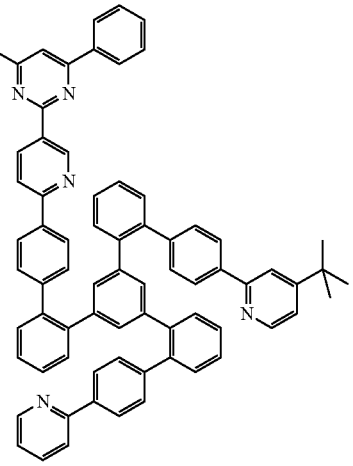 |
| L108 | 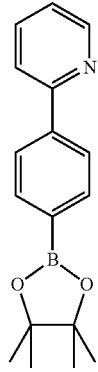 908350-80-1 | 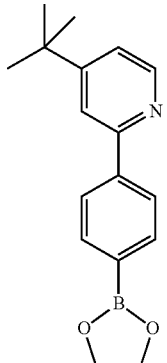 1989596-74-8 | 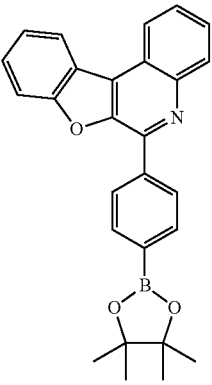 1848992-72-2 | 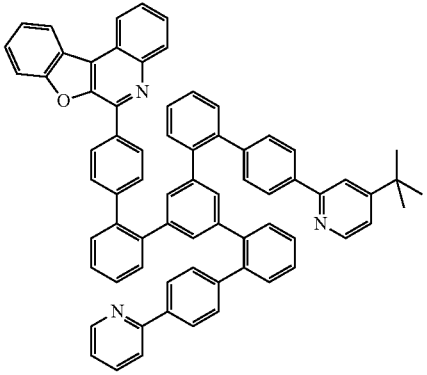 [SMILES: CC(C)(C)c1ccnc(-c2ccc(-c3ccccc3-c3cc(-c4ccccc4-c4ccc(-c5ccccn5)cc4)cc(-c4ccccc4-c4ccc(-c5nc6ccccc6c6c5oc5ccccc56)cc4)c3)cc2)c1] |

-continued

| Ex. | Boronic acid/ester 1 Step 1 | Boronic acid/ester 2 Step 2 | Boronic acid/ester 3 Step 3 | Product |
|---|---|---|---|---|
| L109 | 879291-27-7 | 1989596-37-3 | 1989596-60-2 | |
| L110 | 879291-27-7 | 1989596-42-0 | 1365756-85-9 | |

-continued

| Ex. | Boronic acid/ester 1 Step 1 | Boronic acid/ester 2 Step 2 | Boronic acid/ester 3 Step 3 | Product |
|---|---|---|---|---|
| L111 | 879291-27-7 | 1989596-42-0 | 1989596-54-4 | |

Synthesis of the Metal Complexes

The complexes which follow can be prepared with the ligands obtained in accordance with the invention by the processes described in WO 2016/124304. The yields after purification by repeated hot extraction and fractional sublimation are in the range of 30-70%, with a purity by HPLC of 99.8%

| Ex. | Ligand | Metal complex |
|---|---|---|
| IrL1 | L1 | |

-continued
| Ex. | Ligand | Metal complex |
|---|---|---|
| IrL2 | L2 | 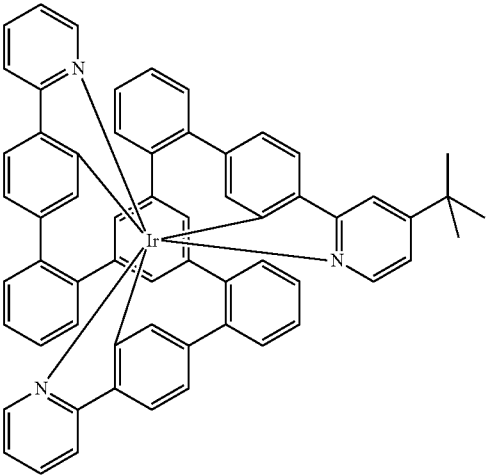 |
| IrL3 | L3 | 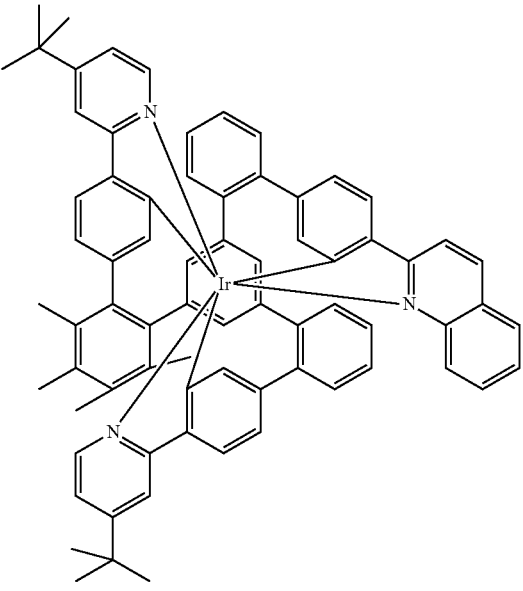 |
| IrL4 | L4 | 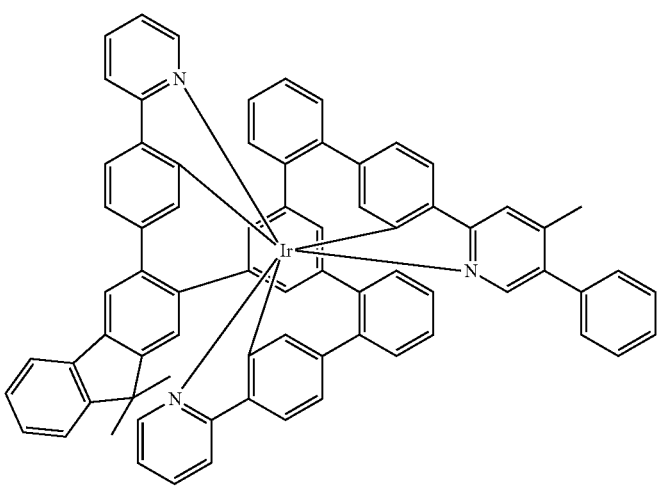 |

| Ex. | Ligand | Metal complex |
|---|---|---|
| IrL5 | L5 | 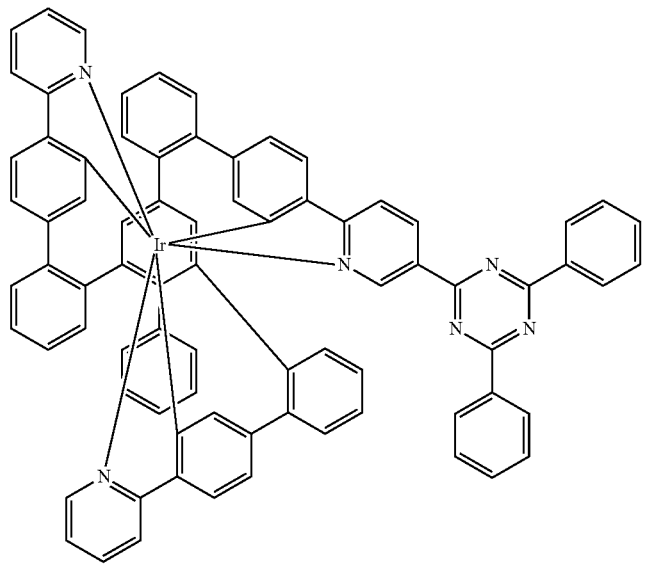 |
| IrL6 | L6 | 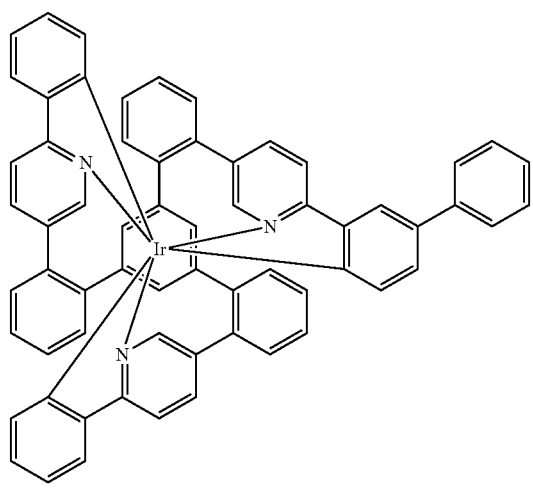 |
| IrL7 | L7 | 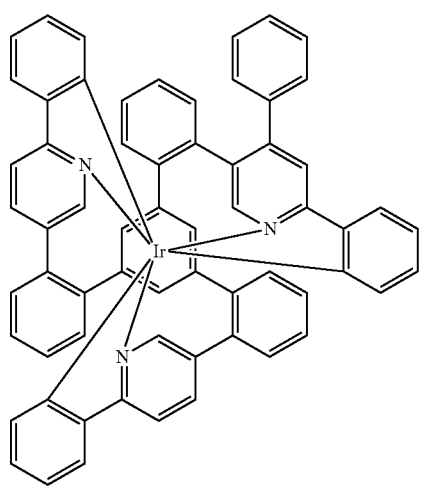 |

-continued
| Ex. | Ligand | Metal complex |
|---|---|---|
| IrL8 | L8 | 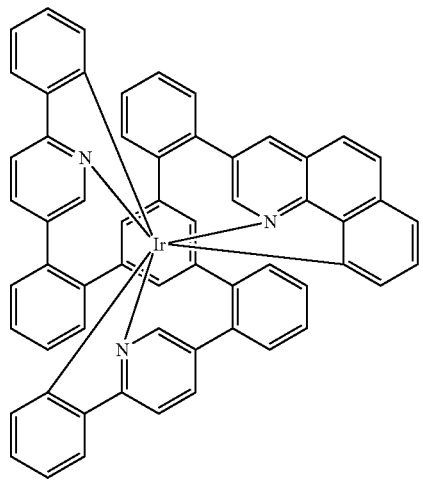 |
| IrL9 | L9 | 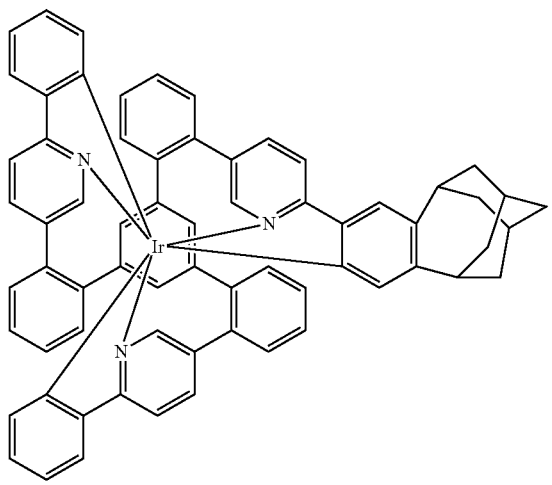 |
| IrL10 | L10 | 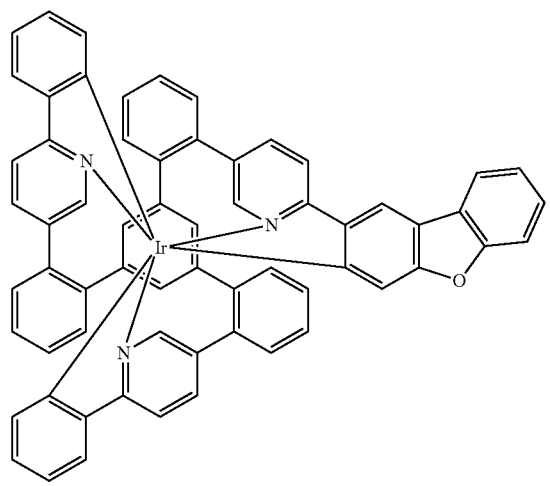 |

-continued
| Ex. | Ligand | Metal complex |
|---|---|---|
| IrL11 | L11 | 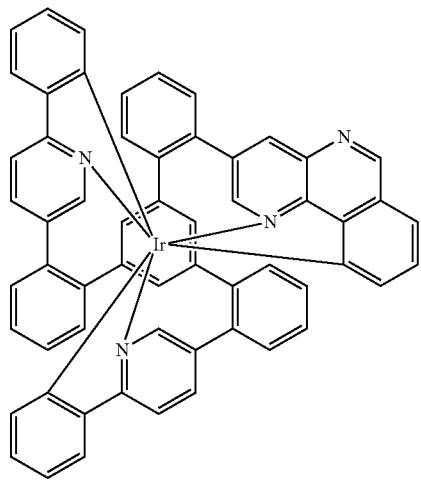 |
| IrL100 | L100 | 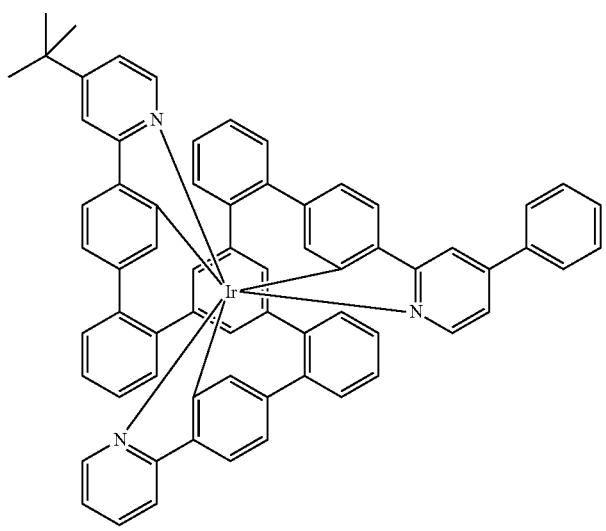 |
| IrL101 | L101 | 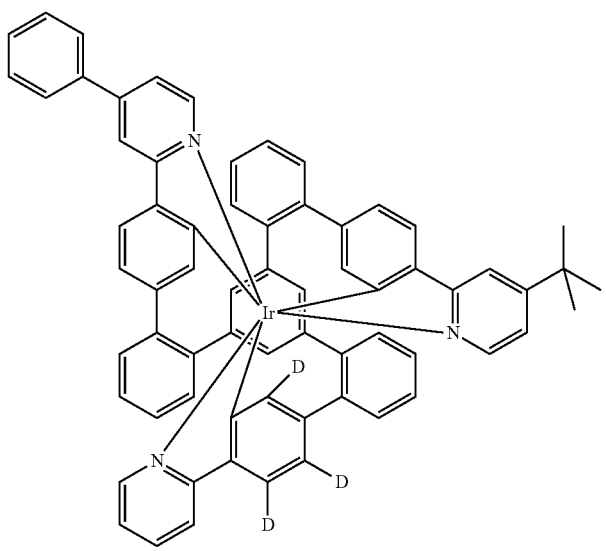 |

| Ex. | Ligand | Metal complex |
|---|---|---|
| IrL102 | L102 | 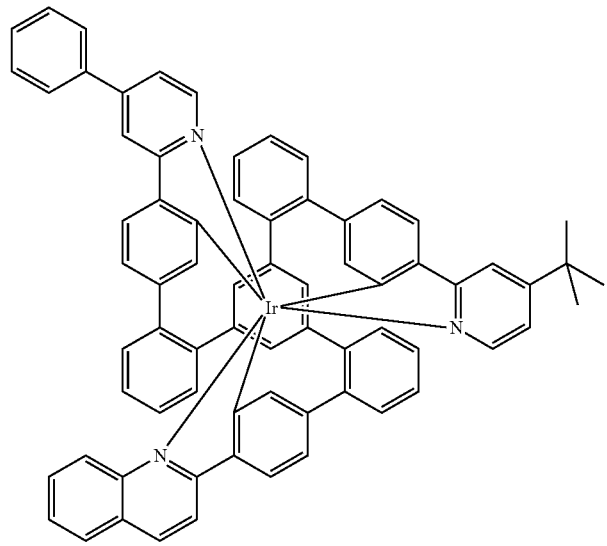 |
| IrL103 | L103 | 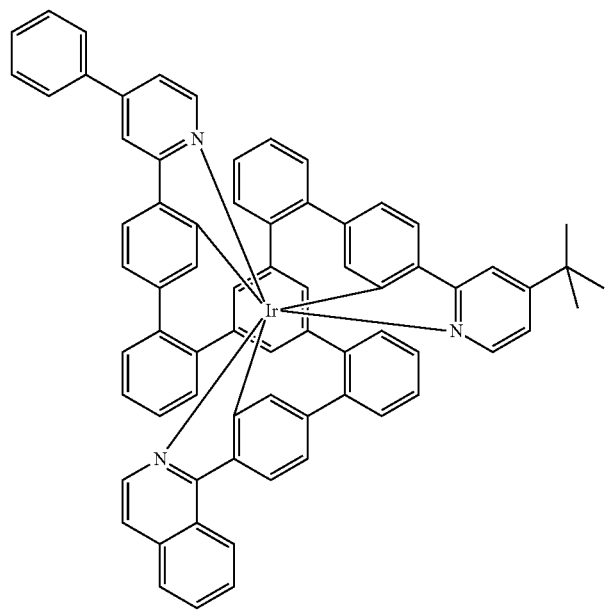 |

| Ex. | Ligand | Metal complex |
|---|---|---|
| IrL104 | L104 | 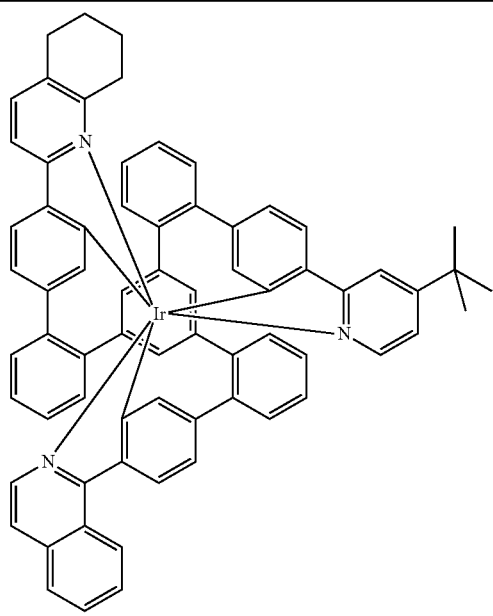 |
| IrL105 | L105 | 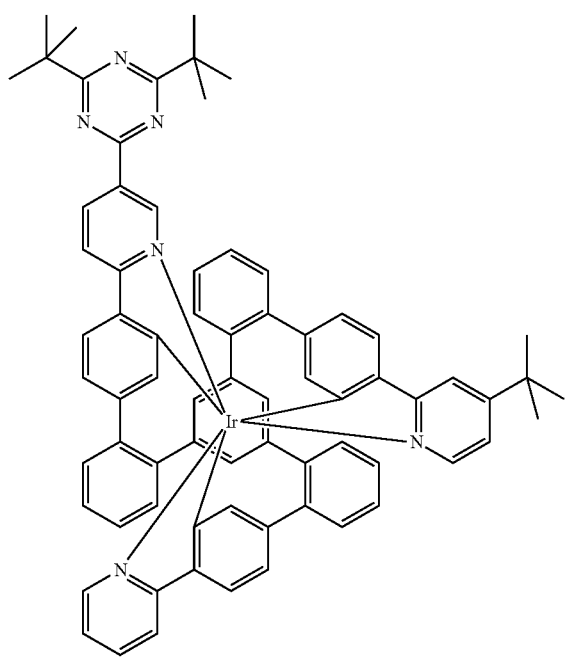 |

-continued
| Ex. | Ligand | Metal complex |
|---|---|---|
| IrL106 | L106 | 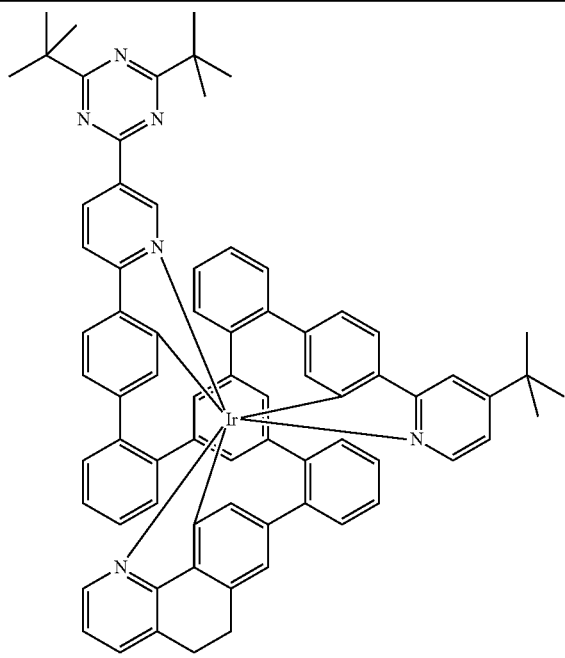 |
| IrL107 | L107 | 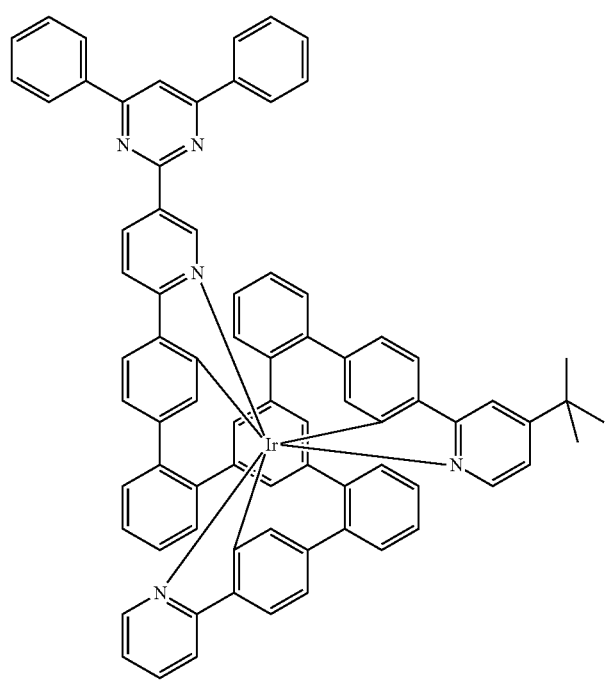 |

-continued
| Ex. | Ligand | Metal complex |
|---|---|---|
| IrL108 | L108 | 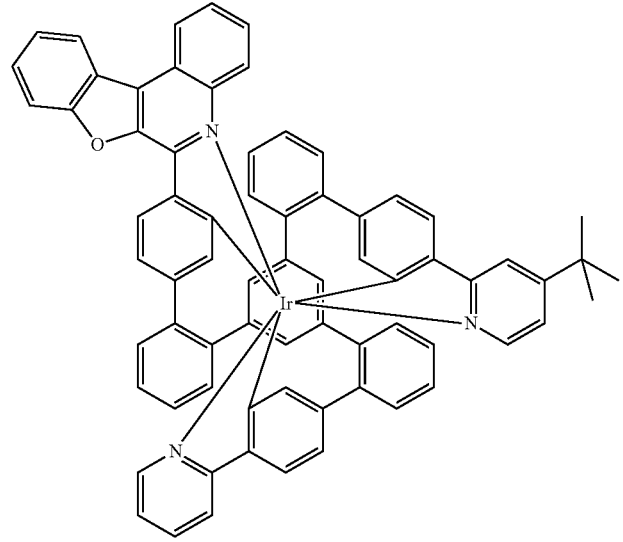 |
| IrL109 | L109 | 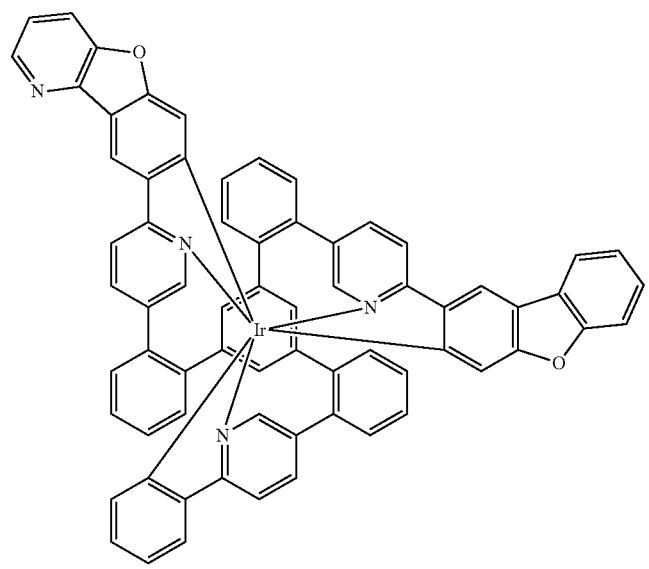 |

| Ex. | Ligand | Metal complex |
|---|---|---|
| IrL110 | L110 | 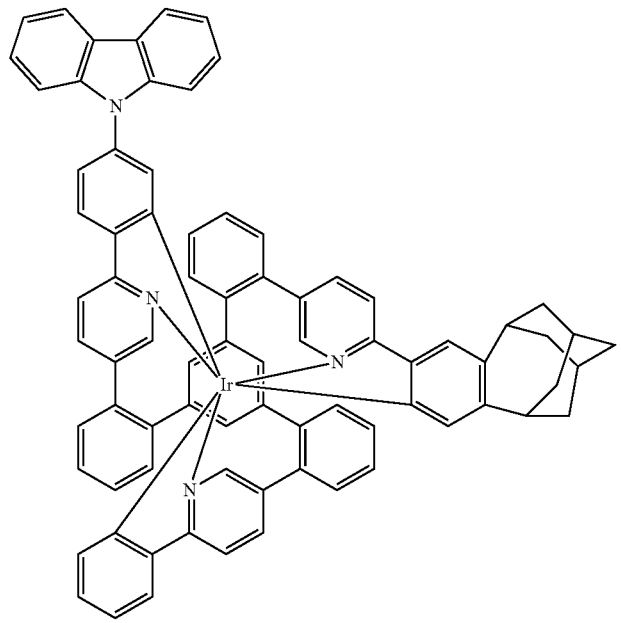 |
| IrL111 | L111 | 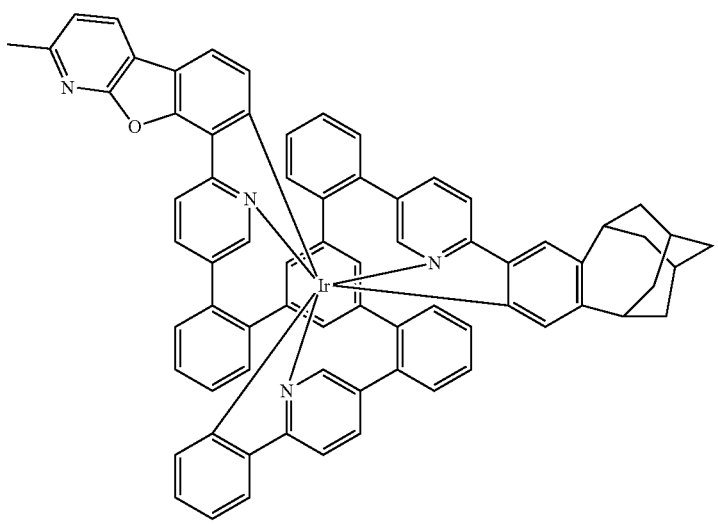 |

In an analogous manner, it is possible to prepare the metal complexes which follow from the corresponding ligands, which can be prepared by the process detailed above:
Ir1
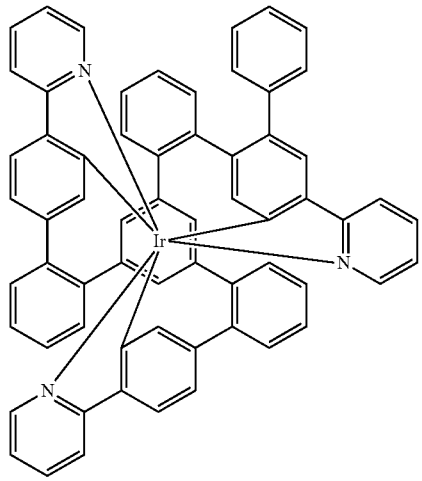
Ir2
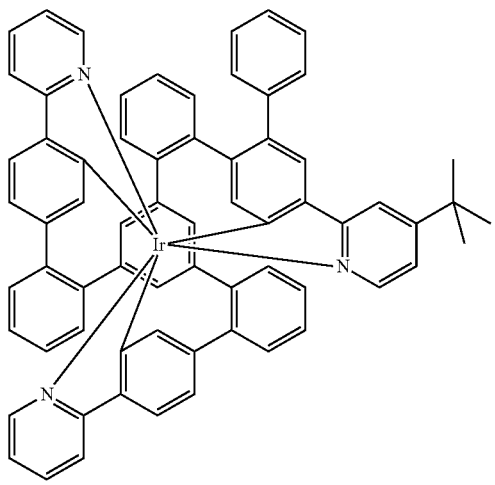
Ir3
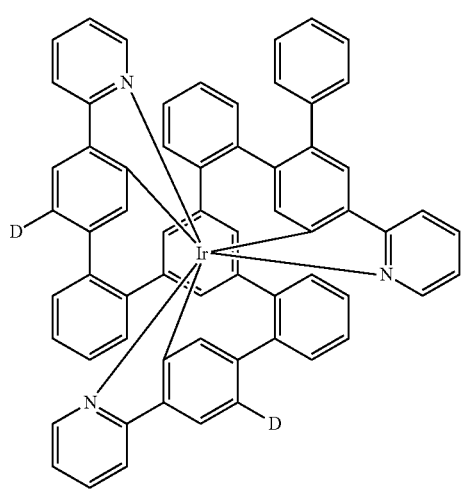
Ir4
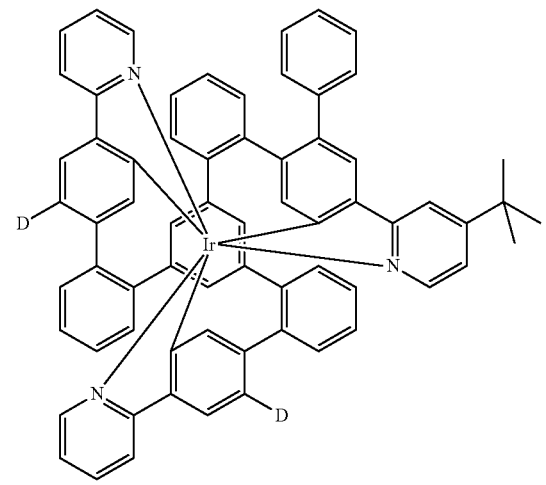
Ir5
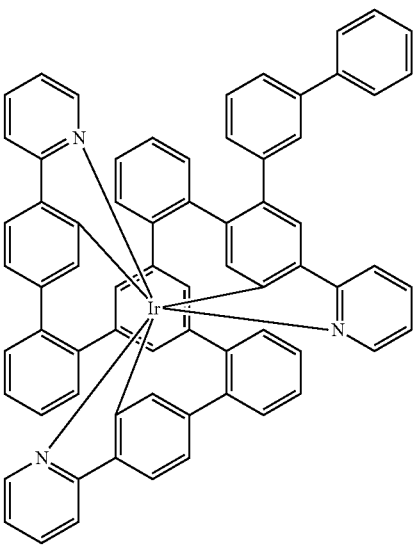
Ir6
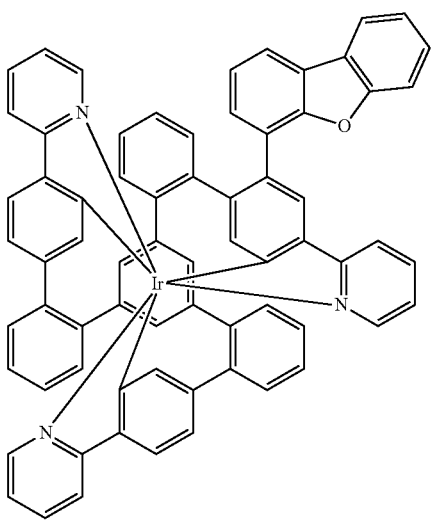

Ir7
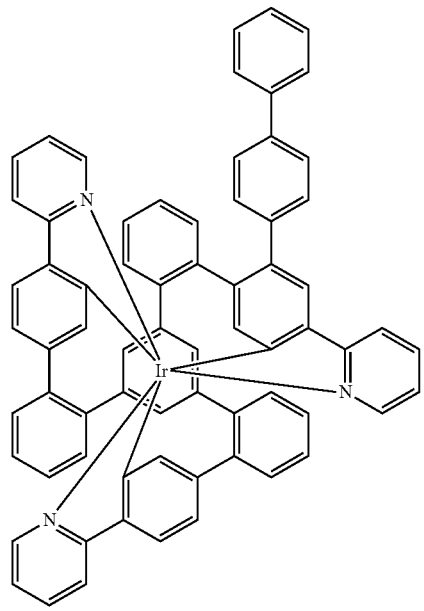
Ir10
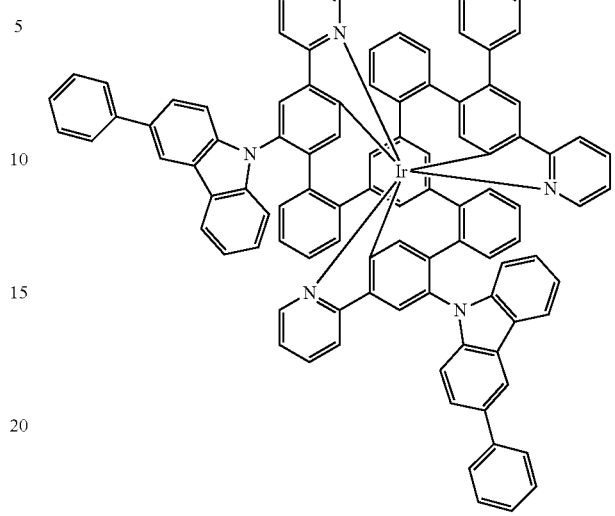
Ir8
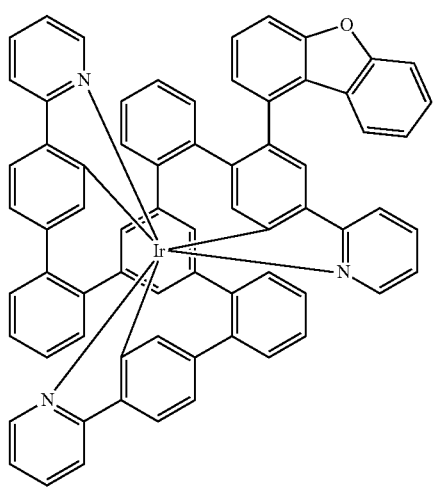
Ir11
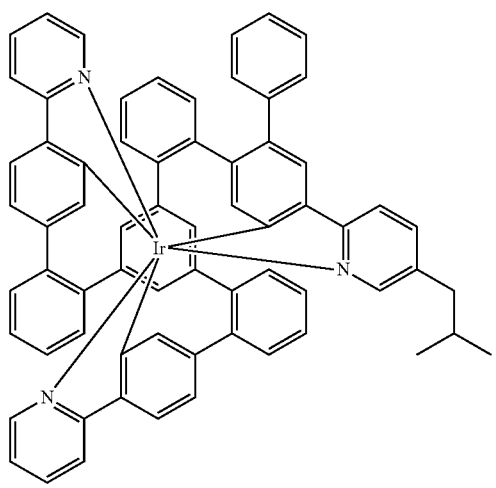
Ir9
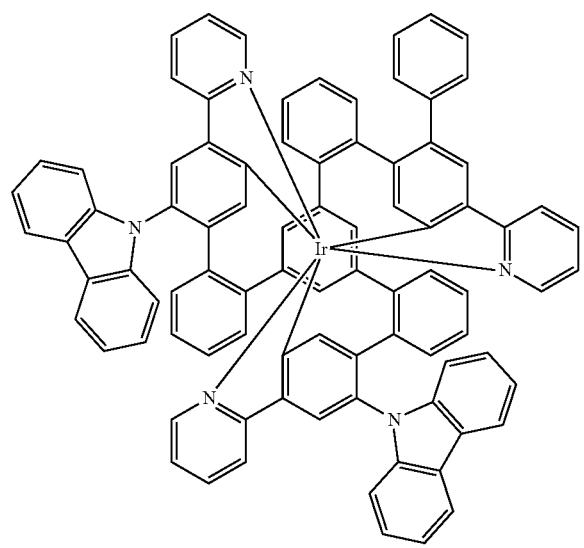
Ir12
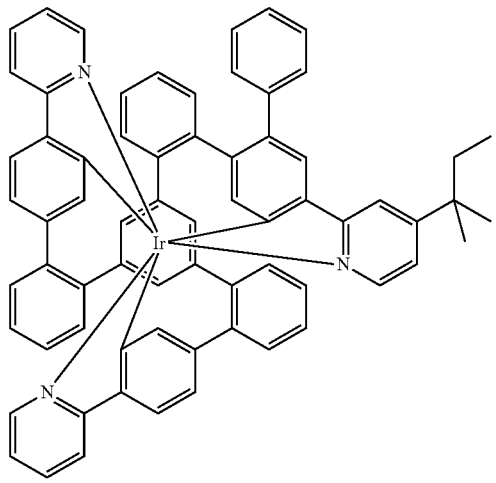

-continued
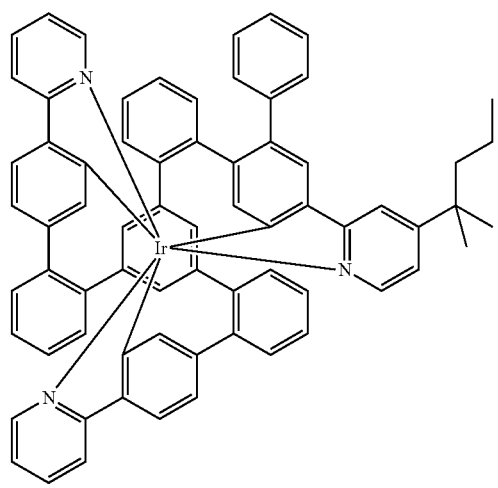
Ir13
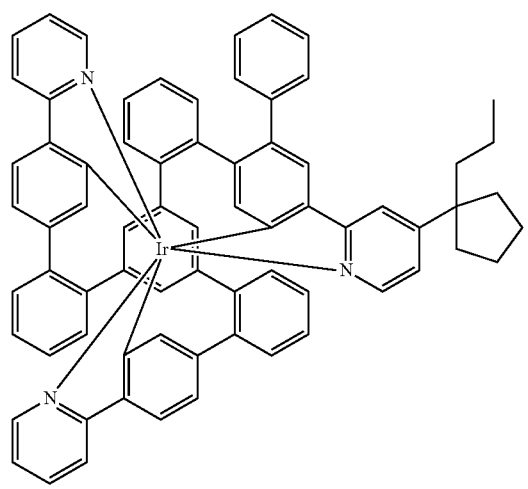
Ir16
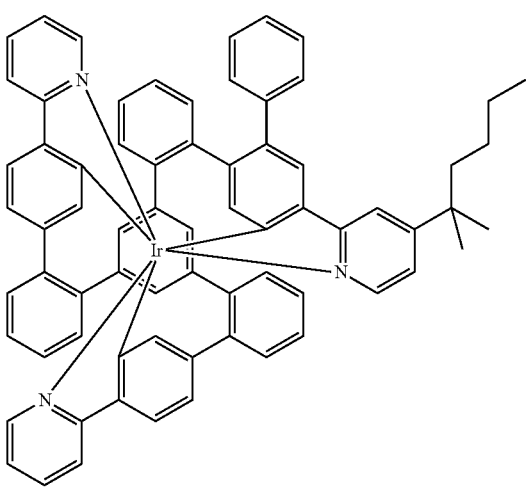
Ir14
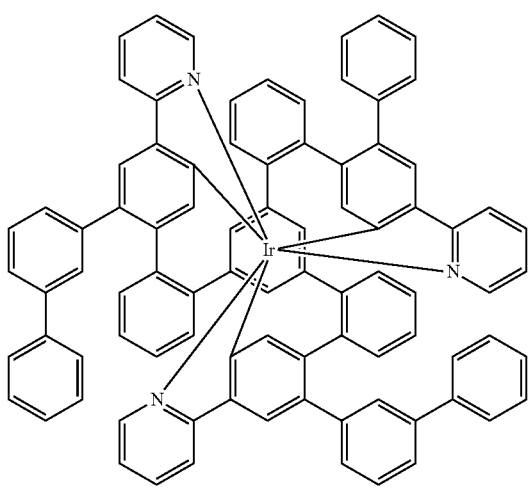
Ir17
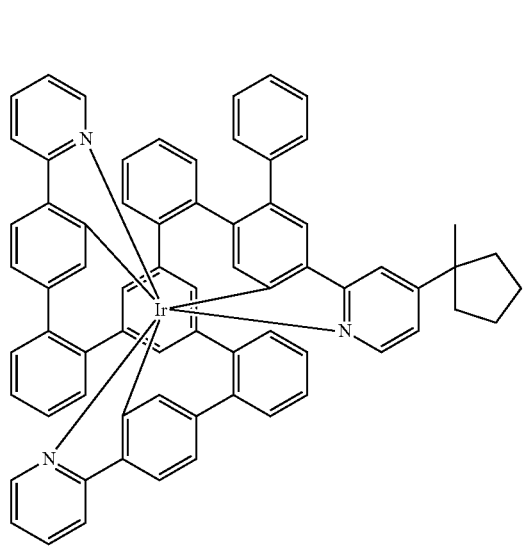
Ir15
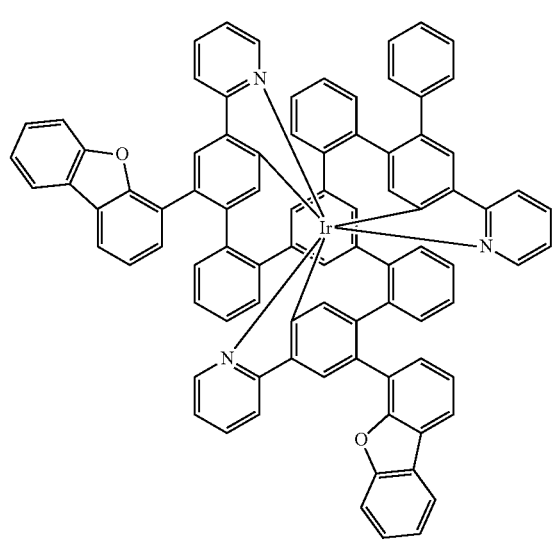
Ir18

167
-continued
Ir19
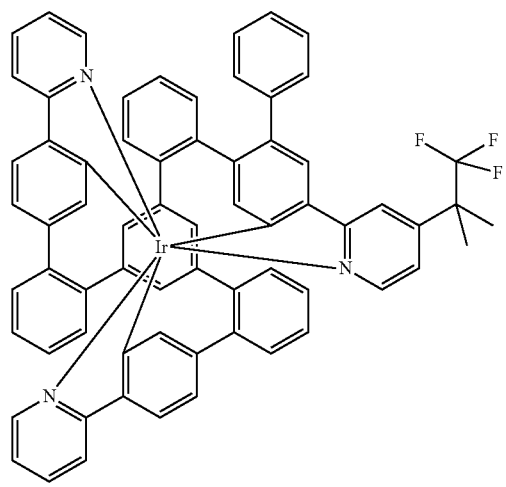
Ir20
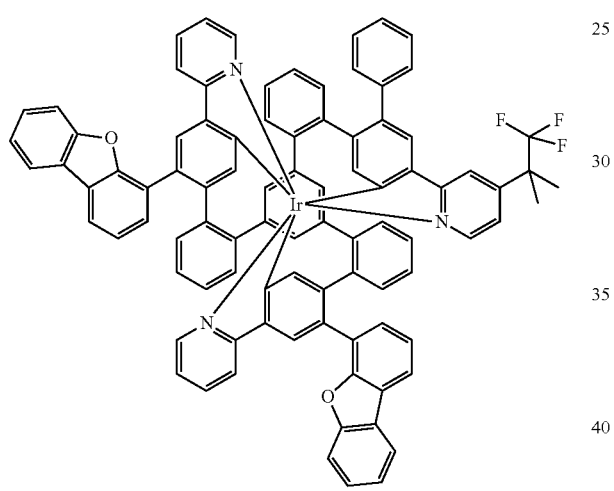
Ir21
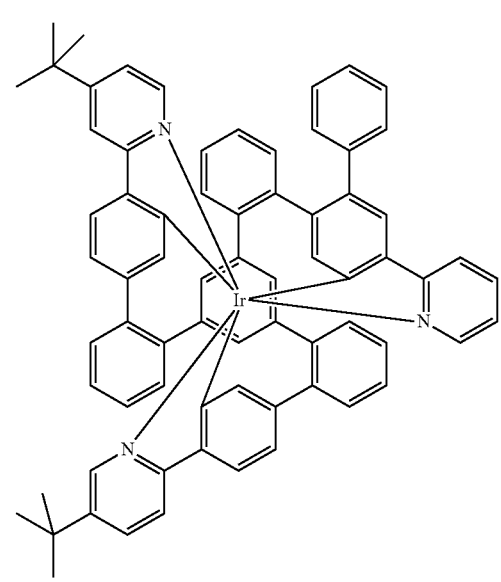
168
-continued
Ir22
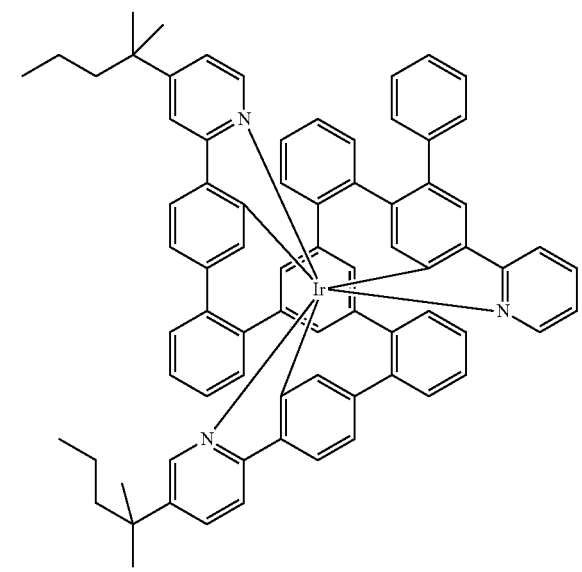
Ir23
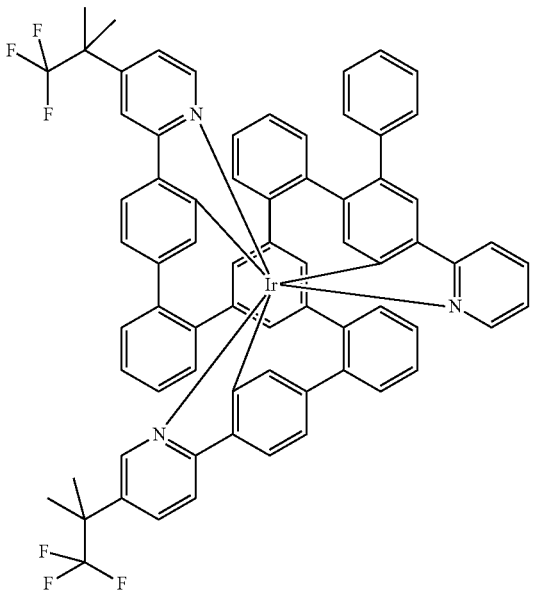

Ir24
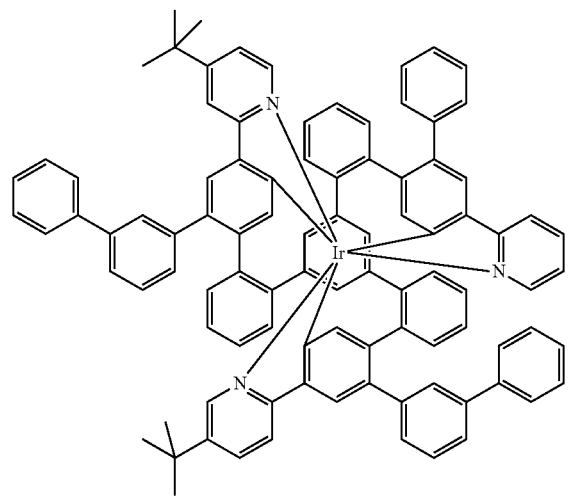
Ir25
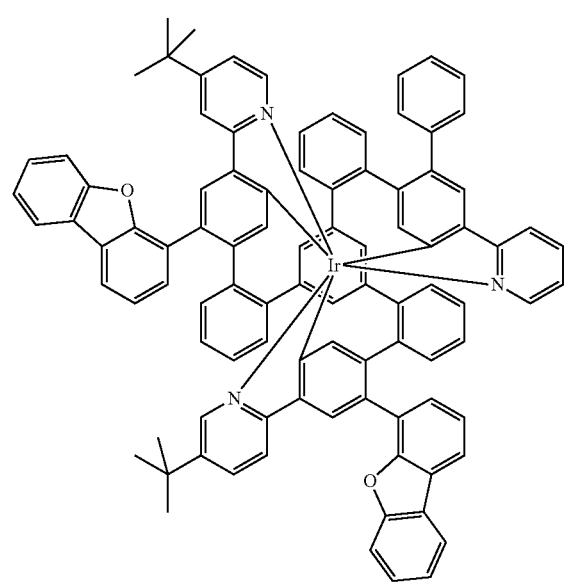
Ir26
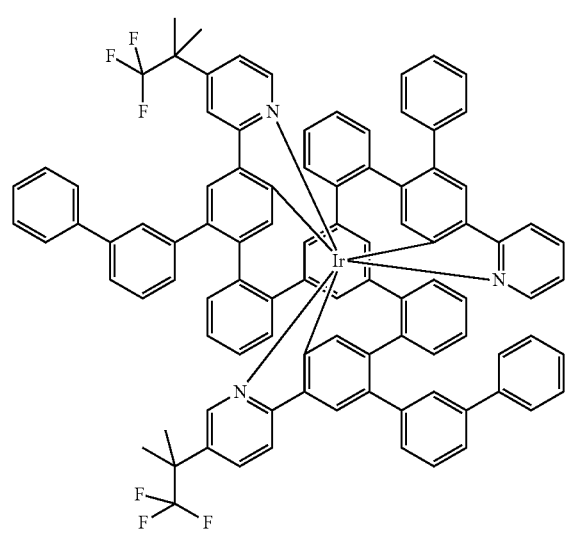
Ir27
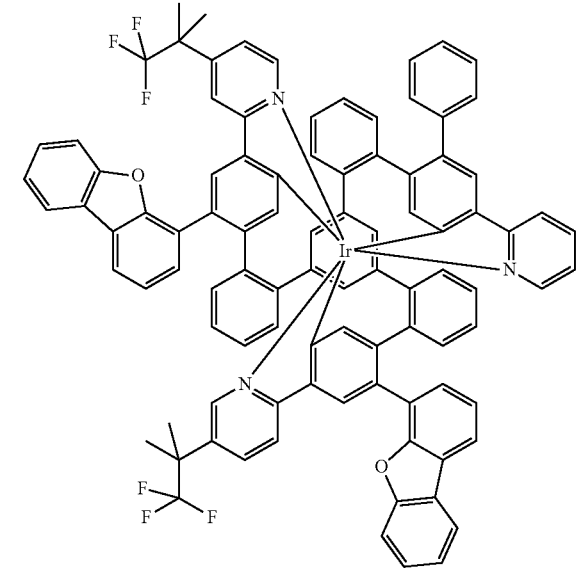
Ir28
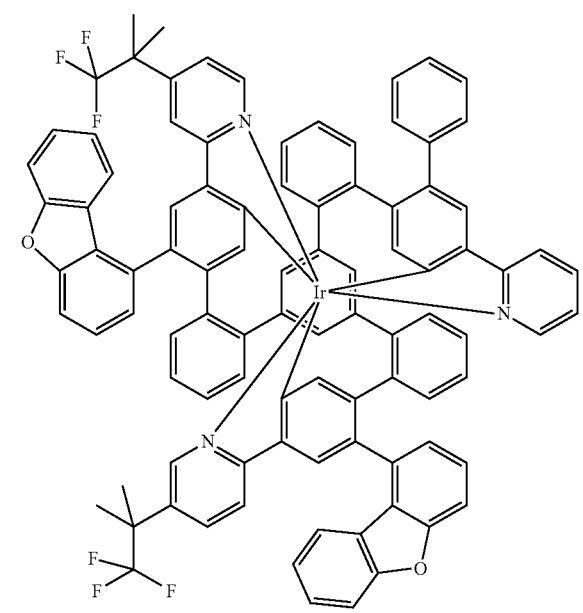

-continued
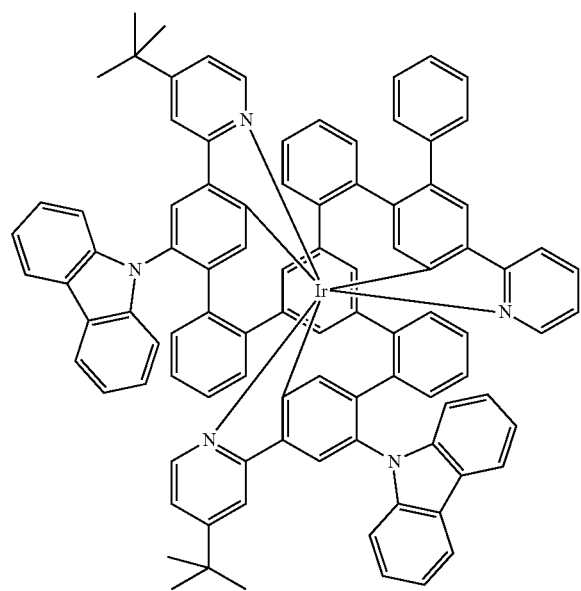
Ir29
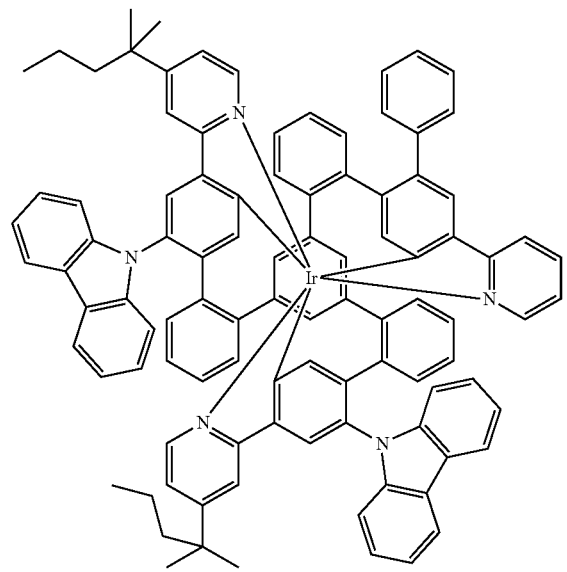
Ir31
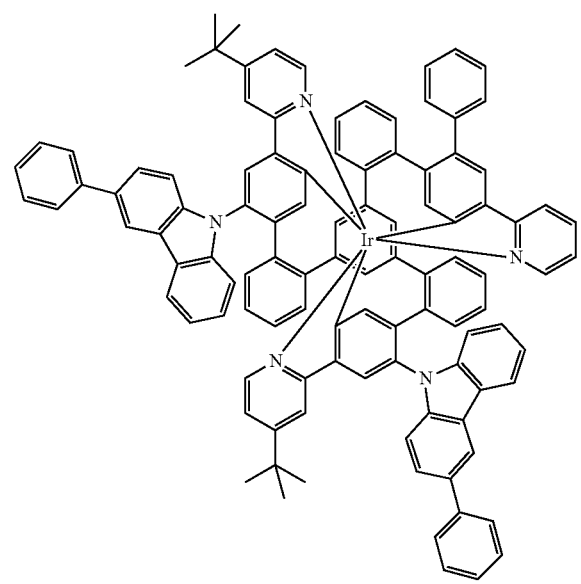
Ir30

-continued
Ir33
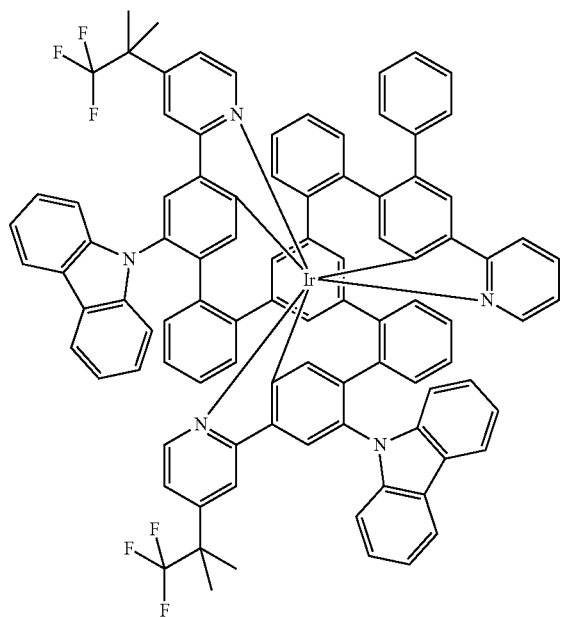
Ir34
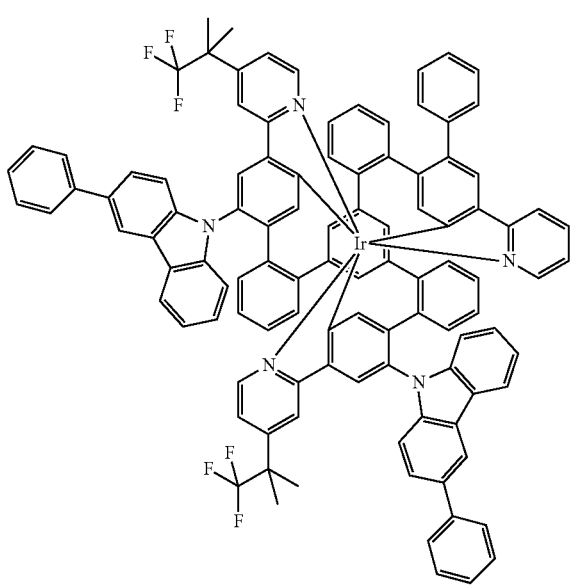
-continued
Ir35
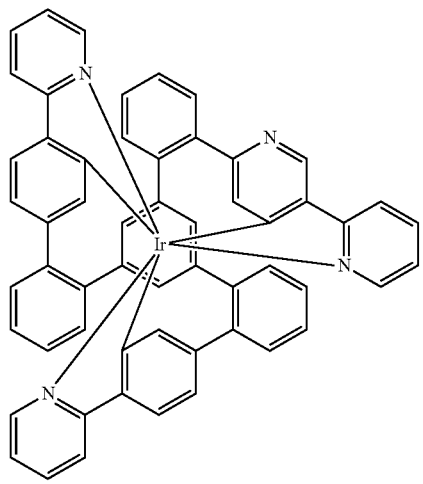
Ir36
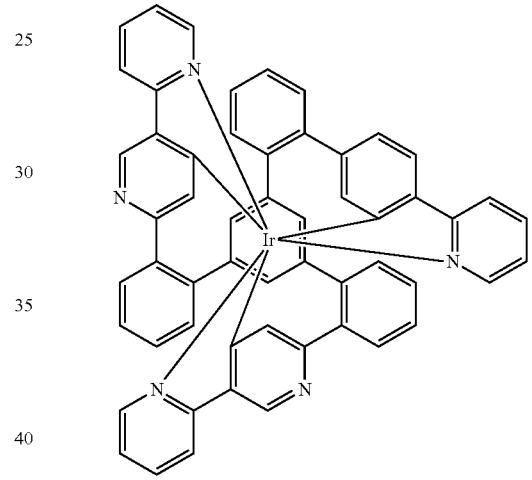
Ir38
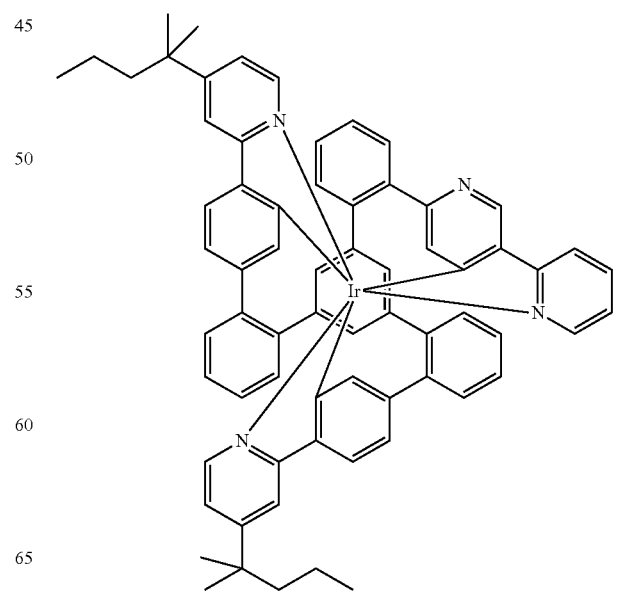

Ir39
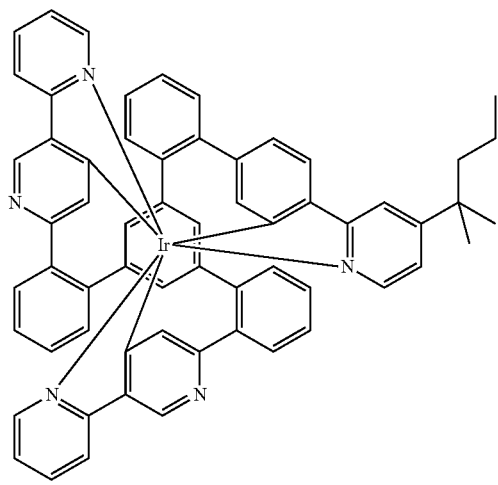
Ir42
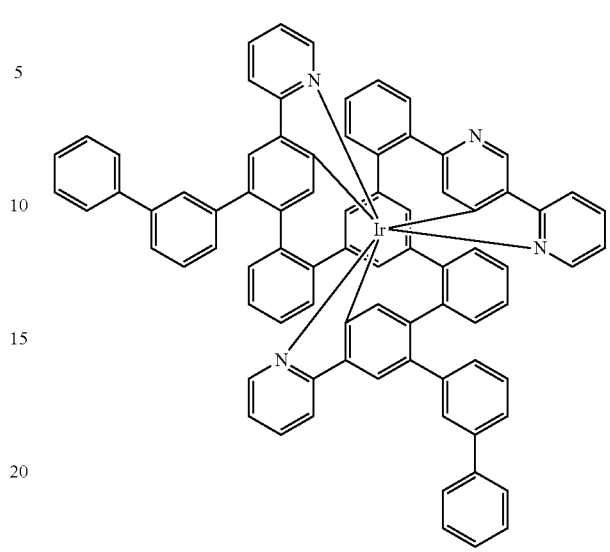
Ir40
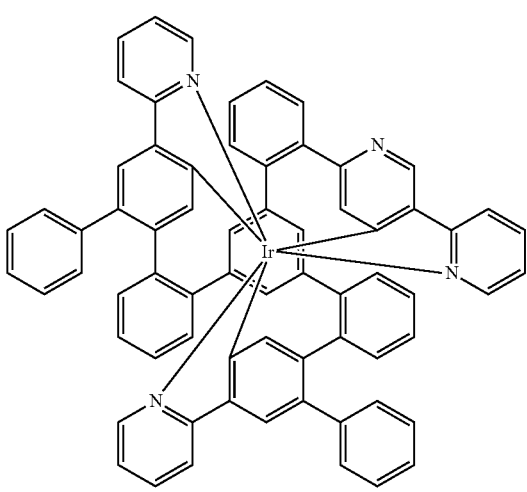
Ir41
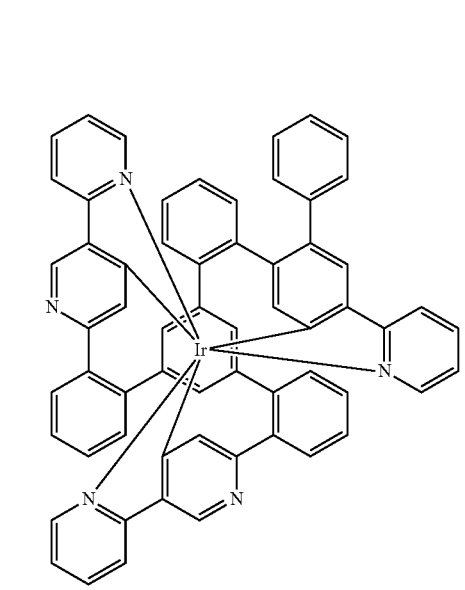
Ir43
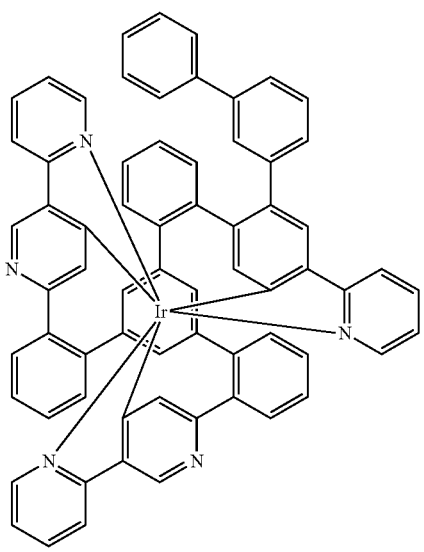

Ir44
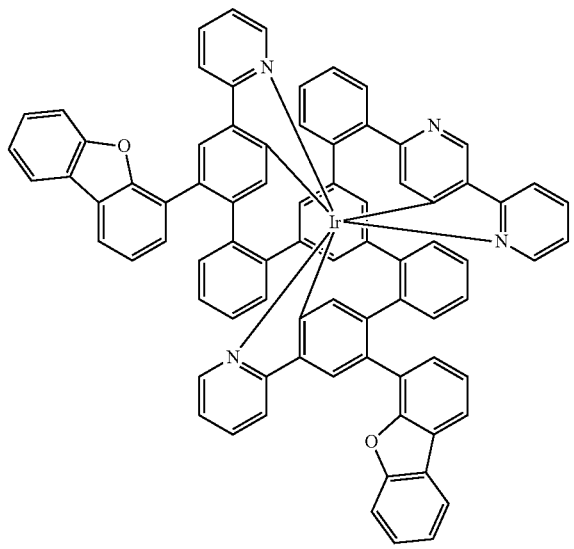
Ir45
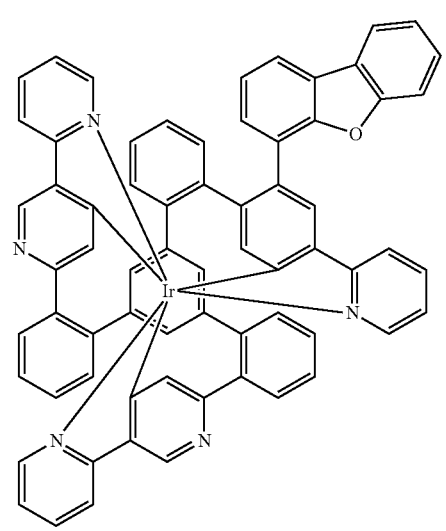
Ir46
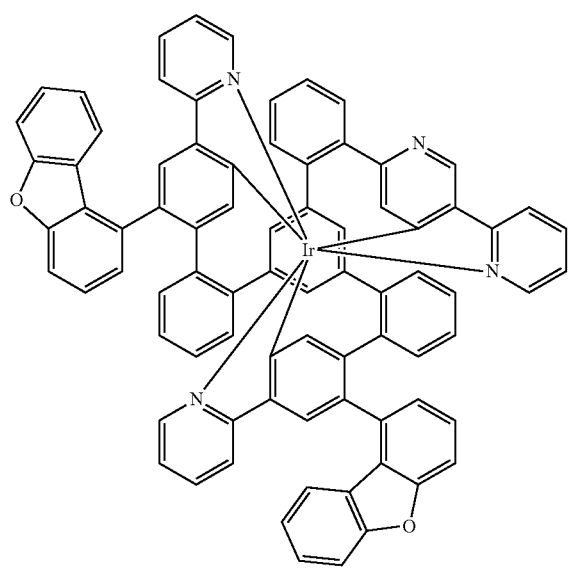
Ir47
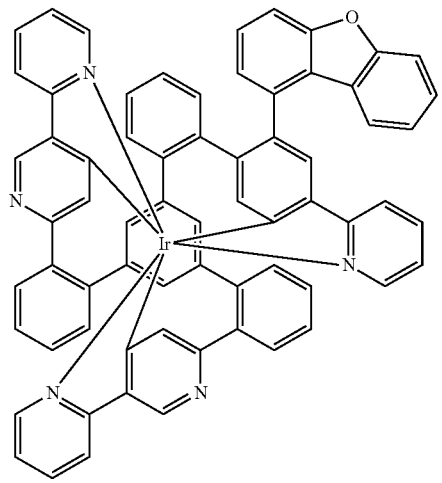
Ir48
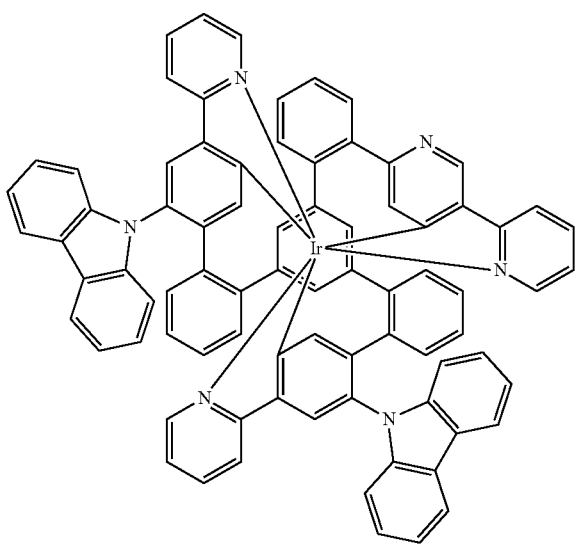
Ir49
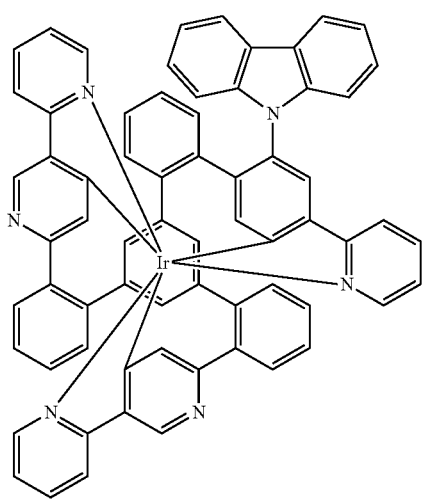

-continued
Ir50
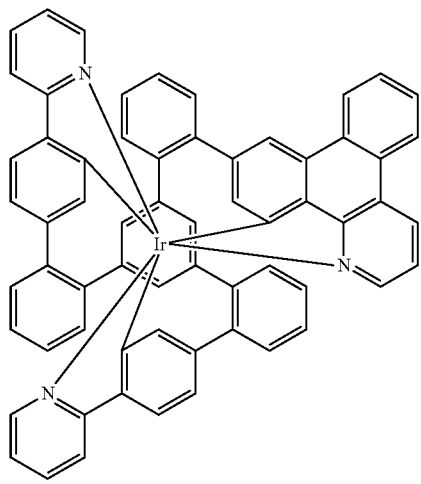
Ir51
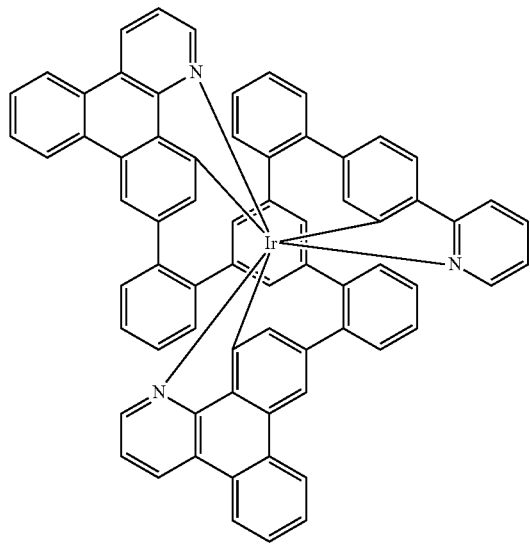
Ir52
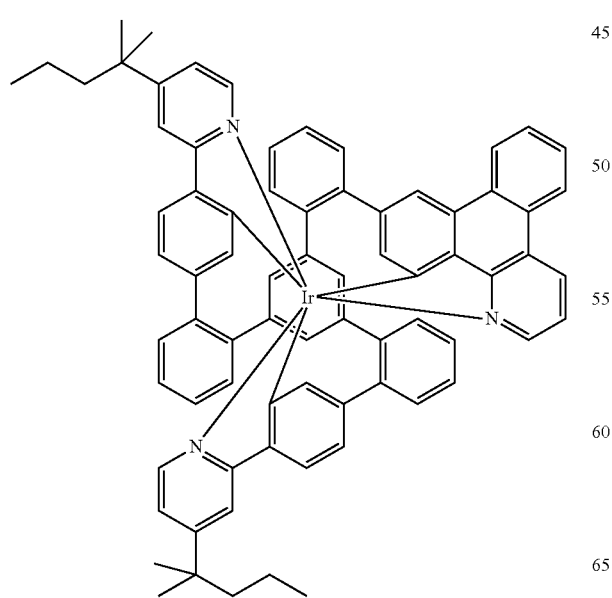
-continued
Ir53
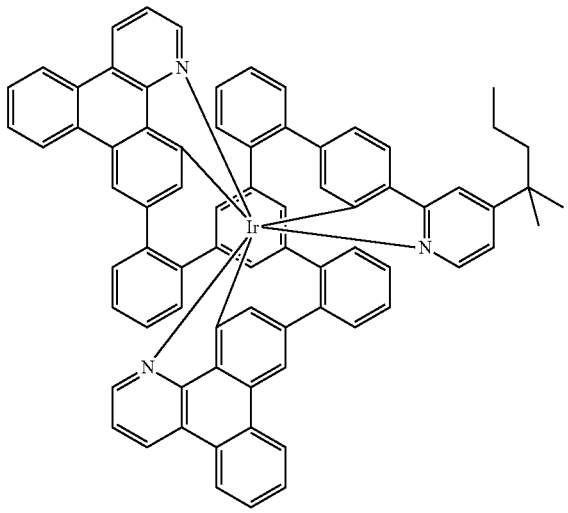
Ir54
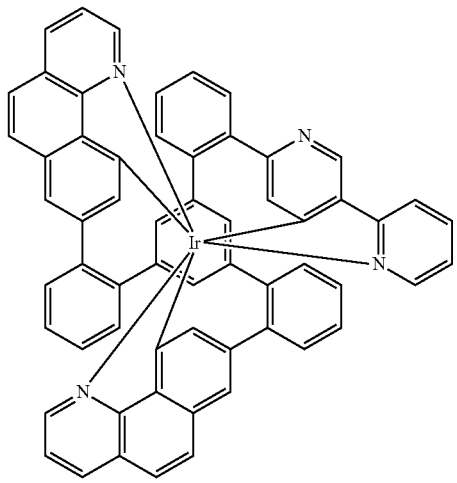
Ir55
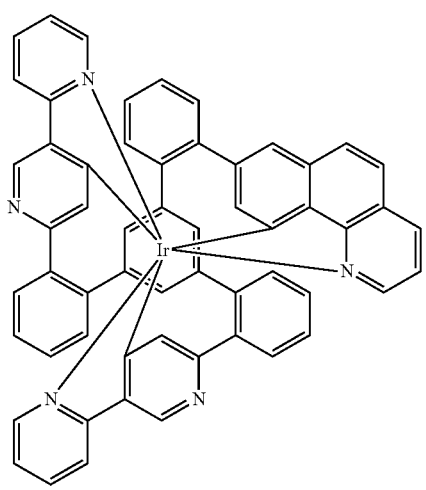

Ir56
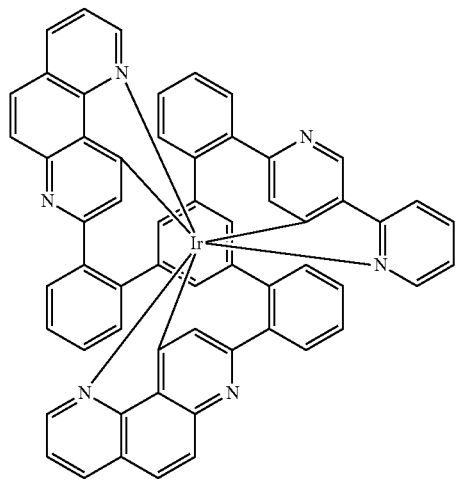
Ir57
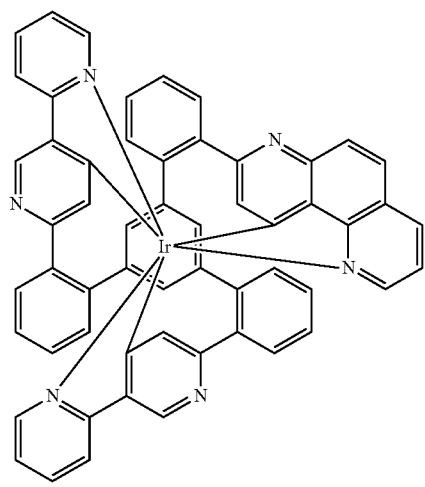
Ir58
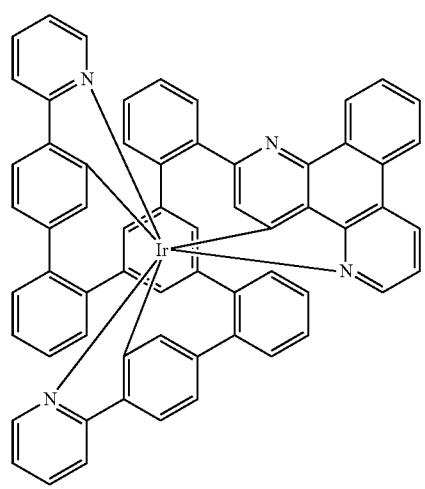
Ir59
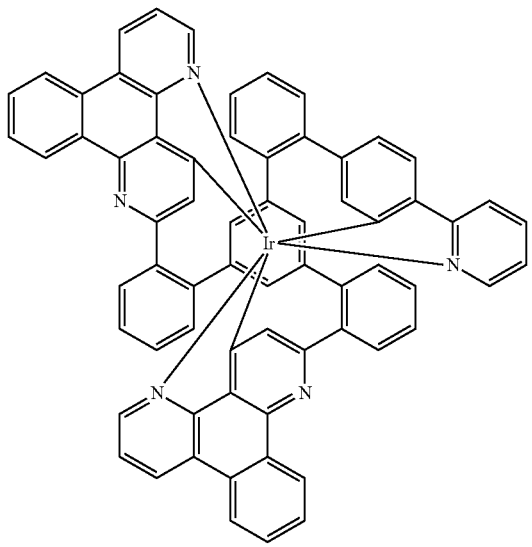
Ir60
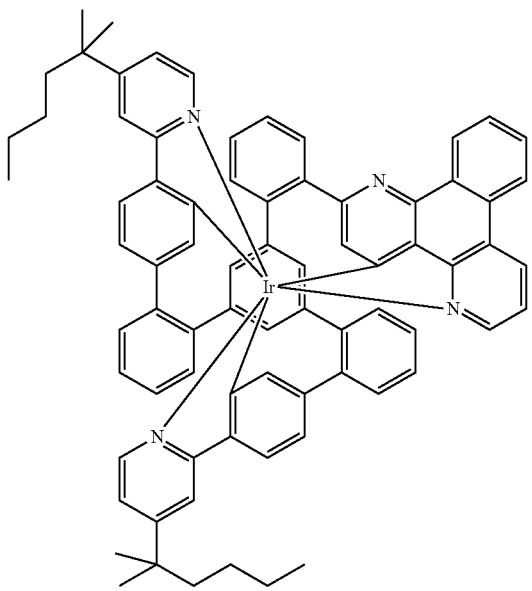

Ir61
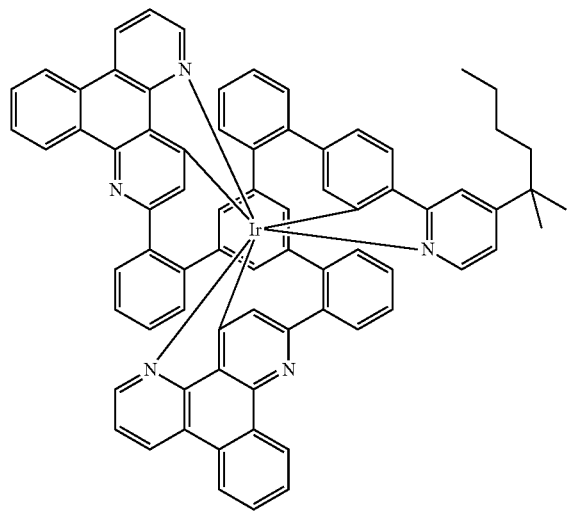
Ir62
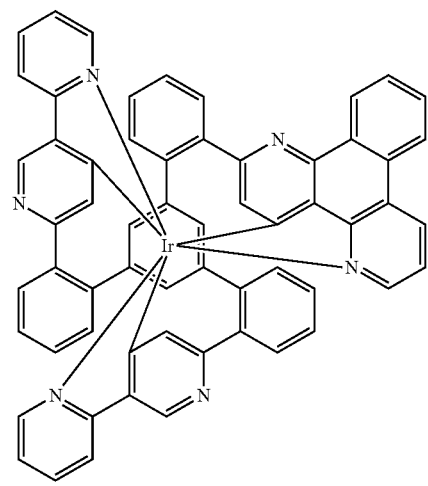
Ir63
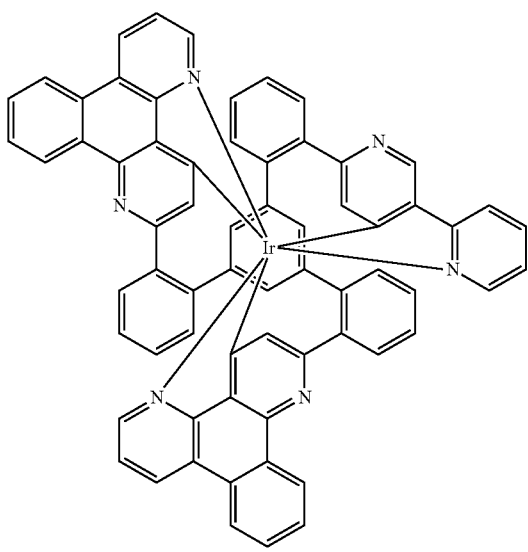
Ir64
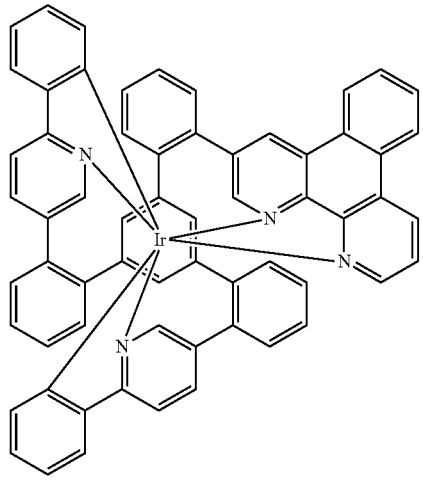
Ir65
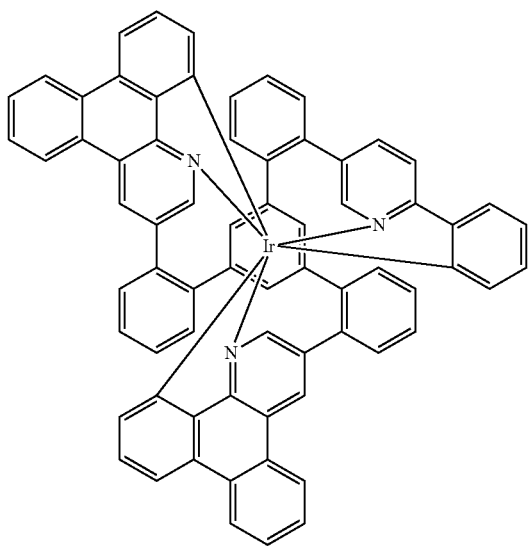
Ir66
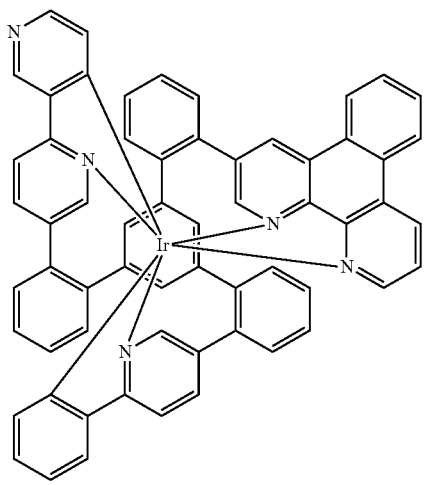

-continued
Ir67
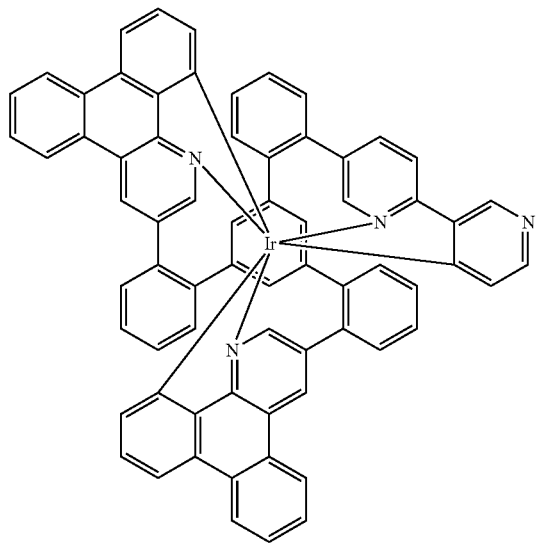
Ir68
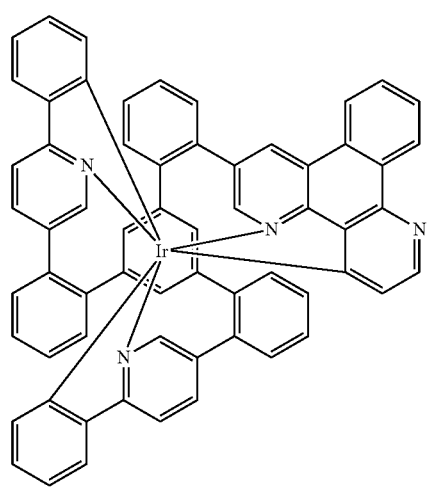
Ir69
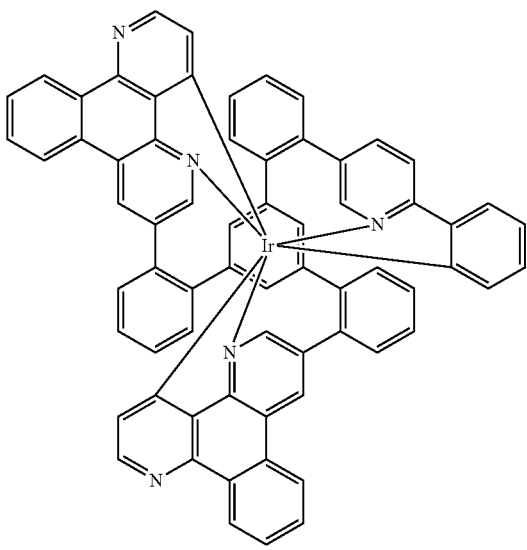
-continued
Ir70
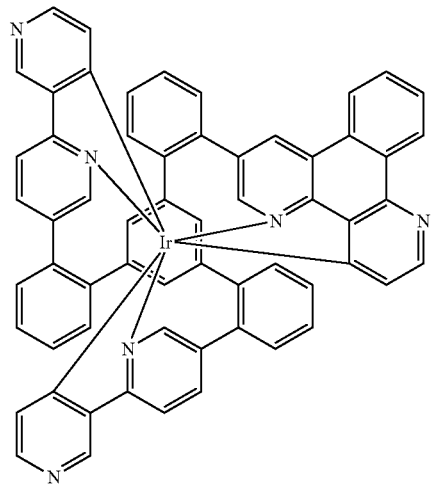
Ir71
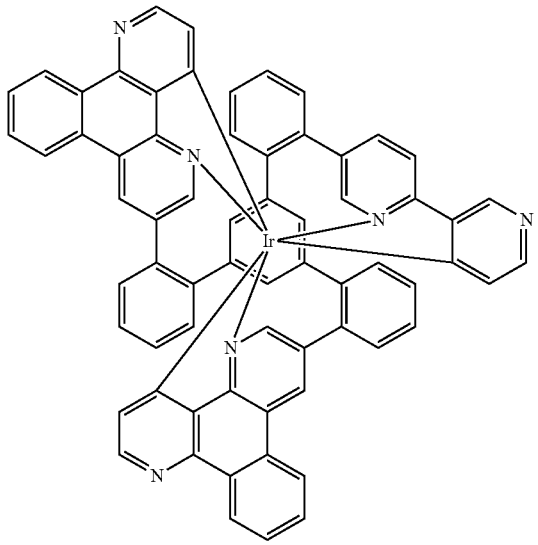
Ir72
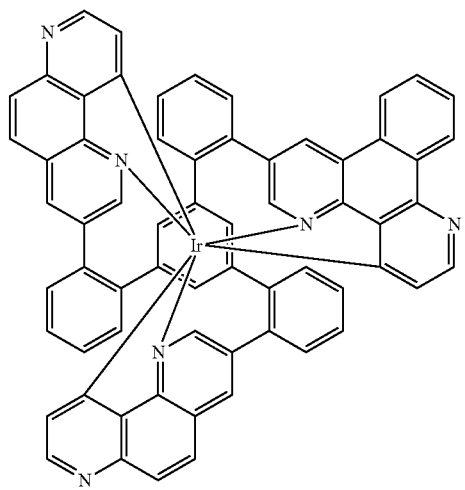

Ir73
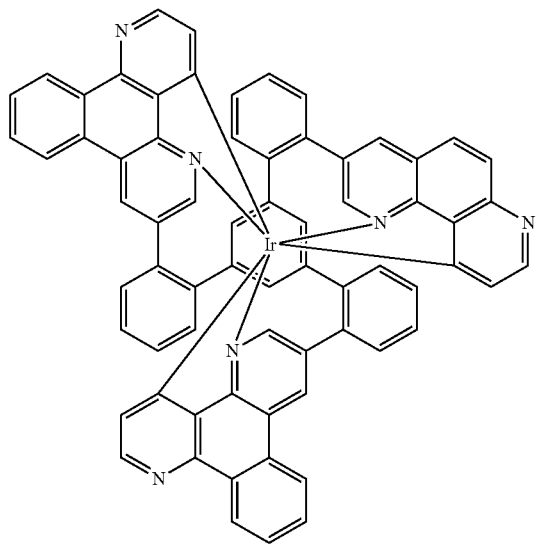
Ir74
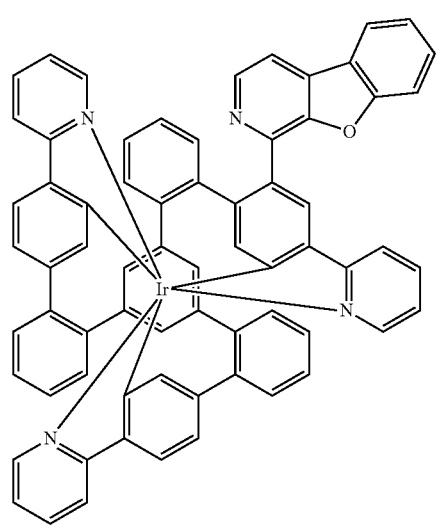
Ir75
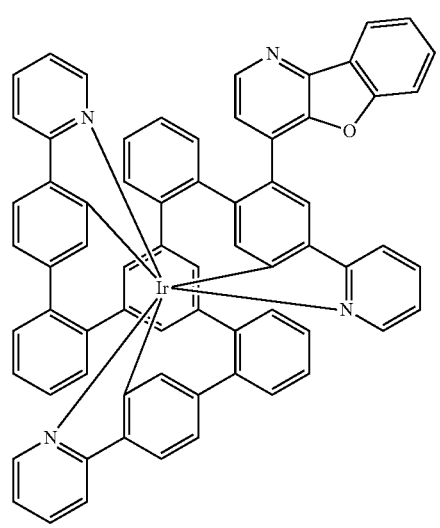
Ir76
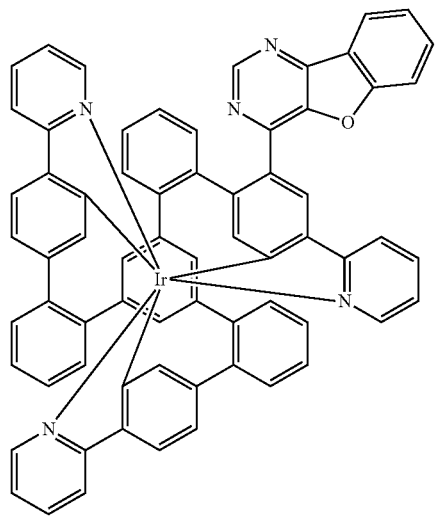
Ir77
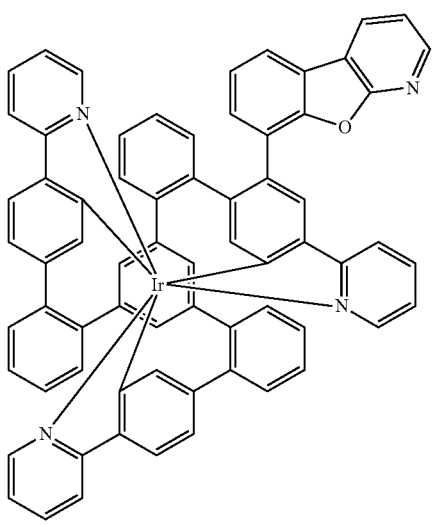
Ir78
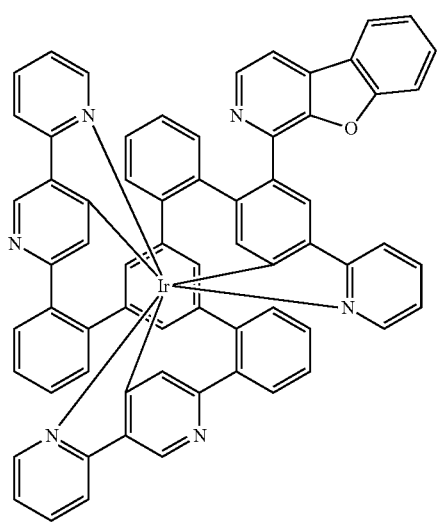

Ir79
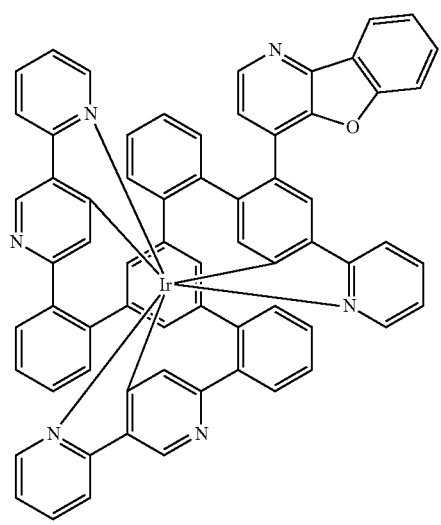
Ir80
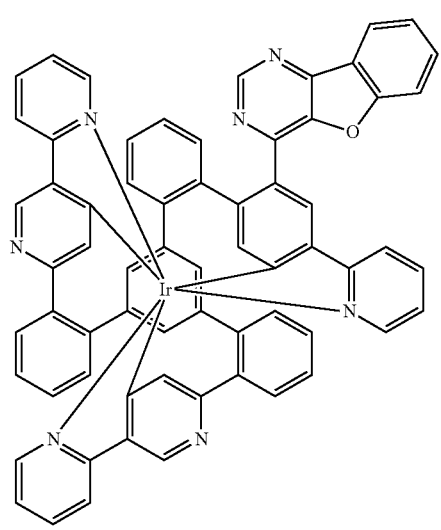
Ir81
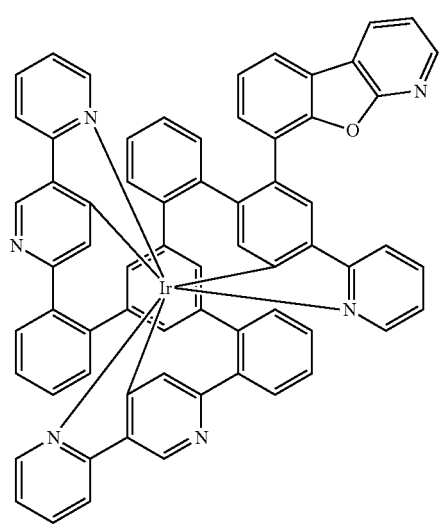
Ir82
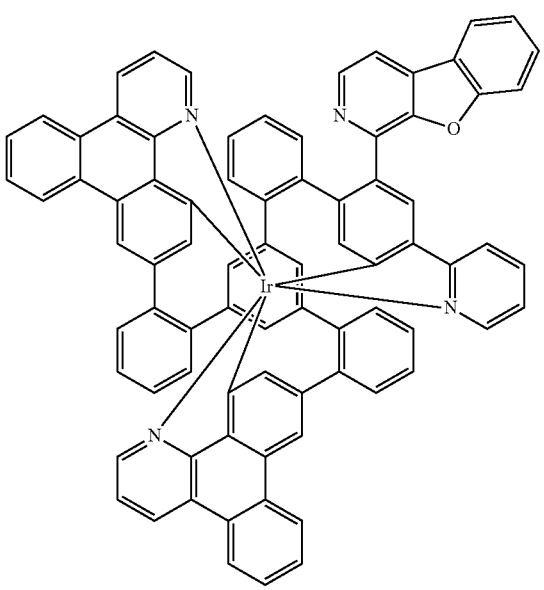
Ir83

Ir84

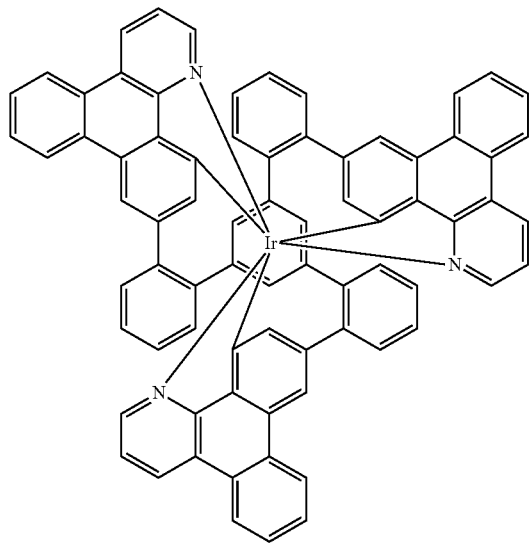

Ir86

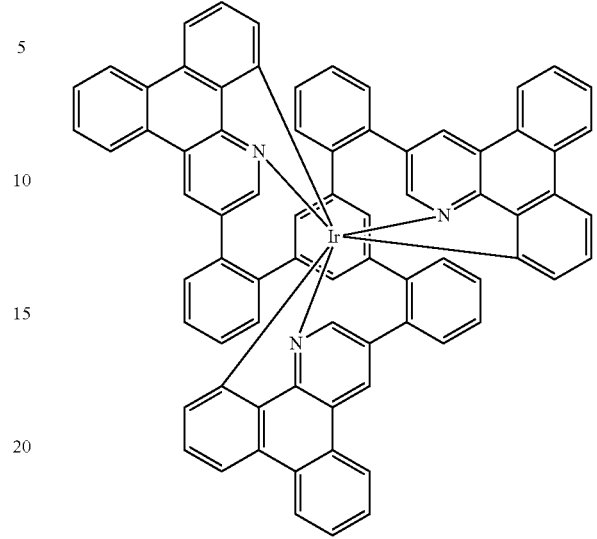

Ir87

Ir85

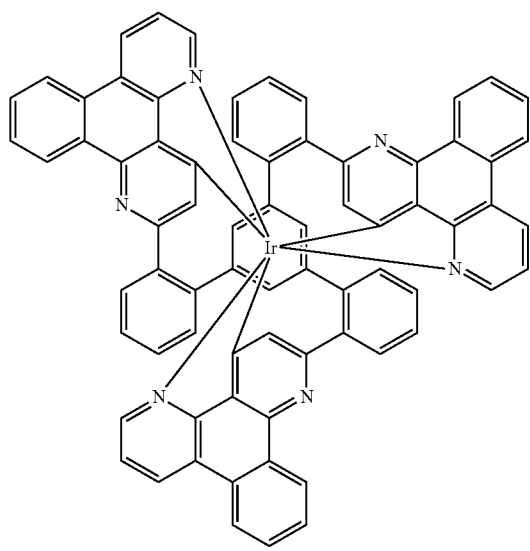

The above-described Ir complexes can be used as triplet emitters (triplet dopants, phosphorescent dopants) in organic electronic devices, especially in organic light-emitting devices (OLEDs). The exact use of the Ir complexes and the exact construction of the OLEDs of this kind is disclosed in WO 2016/124304 using structurally similar compounds. The Ir complexes depicted above emit light in the green, yellow to red spectral region (about 500-650 nm) with good to very good external quantum efficiencies EQE (about 18%-30% EQE) with a long component lifetime LT (LT50@1000 cd/m$^2$ typically >>500 000 h).

The invention claimed is:

1. A compound of formula (II):

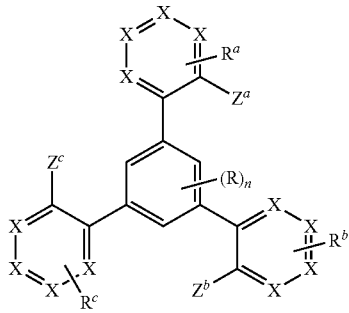

(II)

wherein
$Z^a$, $Z^b$, and $Z^c$
are the same or different and are Cl, Br, I, B(OR)$_2$, OH, or OSO$_2$R;
X is the same or different in each instance and is CR or N, or C if one $R^a$, $R^b$, or $R^c$ radical binds to X, with the proviso that not more than three X symbols per cycle are N;
R, $R^a$, $R^b$, and $R^c$
are the same or different at each instance and are H, D, F, CN, Si(R$^1$)$_3$ a straight-chain alkyl group having 1 to 10 carbon atoms or a branched or cyclic alkyl group having 3 to 10 carbon atoms, where the alkyl group may be substituted by one or more R$^1$ radicals, wherein one or more nonadjacent CH$_2$ groups are optionally replaced by Si(R$^1$)$_2$, or O, or an aromatic or heteroaromatic ring system which has 5 to 24 aromatic ring atoms and is optionally substituted in each case by one or more R$^1$ radicals; and wherein two R radicals together or together with one of the $R^a$, $R^b$, or $R^c$ radicals optionally defines a ring system;
R$^1$ is the same or different in each instance and is H, D, F, CN, Si(R$^2$)$_3$, a straight-chain alkyl group having 1 to 10 carbon atoms or or a branched or cyclic alkyl group having 3 to 10 carbon atoms, where the alkyl group is optionally substituted by one or more R$^2$ radicals, wherein one or more nonadjacent CH$_2$ groups are optionally replaced by Si(R$^2$)$_2$, or O, or an aromatic or heteroaromatic ring system which has 5 to 24 aromatic ring atoms and is optionally substituted in each case by one or more R$^2$ radicals, or an aralkyl or heteroaralkyl group which has 5 to 40 aromatic ring atoms and is optionally substituted by one or more R$^2$ radicals, or a diarylamino group, diheteroarylamino group, or arylheteroarylamino group which has 10 to 40 aromatic ring atoms and is optionally substituted by one or more R$^2$ radicals; and wherein two or more R$^1$ radicals together optionally define a ring system; and
R$^2$ is the same or different in each instance and is H, D, F, or an aliphatic, aromatic, and/or heteroaromatic organic radical having 1 to 20 carbon atoms, wherein one or more hydrogen atoms is optionally replaced by F; and wherein two or more R$^2$ radicals together optionally define a ring system;
n is 0, 1, 2 or 3 and
wherein the compound of formula (I) does not have C$_3$ symmetry and wherein the $Z^a$ group is not the same as the $Z^b$ or $Z^c$ group.

2. The compound of claim 1, wherein the $R^a$ group is not the same as the $R^b$ or $R^c$ group.

3. The compound of claim 1, wherein the compound is a compound of formula (IV):

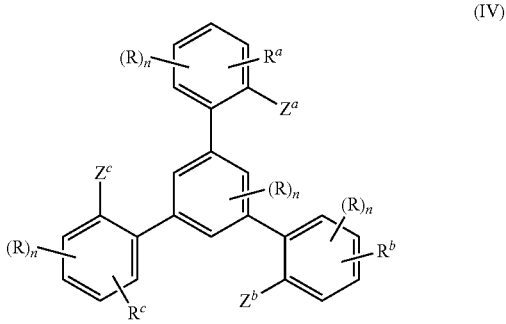

(IV)

wherein n is the same or different in each instance and is 0, 1, 2, or 3.

4. The compound of claim 1, wherein the $Z^a$ is not the same as the $Z^b$ group and the $Z^b$ group is not the same as the $Z^c$ group.

5. The compound of claim 1, wherein the $R^a$ group is not the same as the $R^b$ group and the $R^c$ group, and the $R^b$ group is not the same as the $R^C$ group.

6. The compound of claim 1, wherein at least one of the $R^a$, $R^b$, and $R^c$ groups is selected from a straight-chain alkyl group having 1 to 20 carbon atoms or an alkenyl or alkynyl group having 2 to 20 carbon atoms or a branched or cyclic alkyl group having 3 to 20 carbon atoms, wherein each alkyl alkenyl, or alkynyl group is optionally substituted by one or more R$^1$ radicals, wherein one or more nonadjacent CH$_2$ groups is optionally replaced by R$^1$C=CR$^1$, C≡C, Si(R$^1$)$_2$, C=O, NR$^1$, O, S, or CONR$^1$, or an aromatic or heteroaromatic ring system which has 5 to 40 aromatic ring atoms and is optionally substituted in each case by one or more R$^1$ radicals, or an aryloxy or heteroaryloxy group having 5 to 40 aromatic ring atoms.

7. A process for preparing a polypodal ligand, comprising reacting a compound of claim 1 in a first step with a first reactive ligand in a coupling reaction to form product, reacting the product in a second step with a second reactive ligand in a coupling reaction, wherein the first and second reactive ligands are different, such that a bridge corresponding to the compound of claim 1 without the $Z^a$, $Z^b$, and $Z^c$ groups is formed between a sub-ligand derived from the first reactive ligand and a sub-ligand derived from the second reactive ligand.

8. The process of claim 7, further comprising reacting the product obtained in the second step in a third step with a further reactive ligand in a coupling reaction, wherein the first, second and third reactive ligands are different.

9. The process of claim 7, wherein at least one of the reactive ligands is a bidentate ligand of formula (L-1), (L-2), or (L-3):

(L-1)

-continued

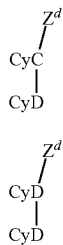

(L-2)

(L-3)

wherein

CyC is the same or different in each instance and is an optionally substituted aryl or heteroaryl group which has 5 to 14 aromatic ring atoms and can coordinate in each case to a metal via a carbon atom and which is bonded in each case to CyD via a covalent bond; the optional substituents are selected from R;

CyD is the same or different in each instance and is an optionally substituted heteroaryl group which has 5 to 14 aromatic ring atoms and can coordinate to a metal via a nitrogen atom or via a carbene carbon atom and which is bonded to CyC via a covalent bond; and $Z^d$ is a reactive group.

10. The compound of claim 1, wherein $R^2$ is a hydrocarbyl radical.

11. The compound of claim 1, wherein n is 0 or 1.

12. The compound of claim 6, wherein at least one of the $R^a$, $R^b$, and $R^c$ groups is selected from a straight-chain alkyl group having 1 to 10 carbon atoms or an alkenyl or alkynyl group having 2 to 10 carbon atoms or a branched or cyclic alkyl group having 3 to 10 carbon atoms, wherein each alkyl, alkenyl, or alkynyl group is optionally substituted by one or more $R^1$ radicals, wherein one or more nonadjacent $CH_2$ groups is optionally replaced by $R^1C=CR^1$, $C\equiv C$, $Si(R^1)_2$, $C=O$, $NR^1$, O, S, or $CONR^1$.

13. The process of claim 7, wherein CyC and CyD are optionally substituted with one or more radicals R.

14. The process of claim 7, wherein $Z^d$ is selected from the group consisting of Cl, Br, I, $B(OR)_2$, OH, $OSO_2R$, or an alkoxy or thioalkoxy group having 1 to 20 carbon atoms.

15. The compound of claim 1, wherein at least one of the $R^a$, $R^b$, and $R^c$ groups is selected from a straight-chain alkyl group having 1 to 8 carbon atoms or a branched or cyclic alkyl group having 3 to 8 carbon atoms, wherein each alkyl group is optionally substituted by one or more $R^1$ radicals.

16. The compound of claim 1, wherein W is identical or different and is H, F, CN, a straight-chain alkyl group having 1 to 5 carbon atoms or a branched or cyclic alkyl group having 3 to 5 carbon atoms, wherein each alkyl group is optionally substituted by one or more $R^2$ radicals or an aromatic or heteroaromatic ring system which has 5 to 13 aromatic ring atoms and is optionally substituted in each case by one or more $R^2$ radicals.

* * * * *